(12) United States Patent
Brown et al.

(10) Patent No.: US 8,808,747 B2
(45) Date of Patent: Aug. 19, 2014

(54) NUCLEIC ACID MICROPARTICLES FOR PULMONARY DELIVERY

(75) Inventors: Larry R. Brown, Newton, MA (US); Kimberly A. Gillis, Beverly, MA (US); Michael V. Gallo, Arlington, MA (US)

(73) Assignees: Baxter International Inc., Deerfield, IL (US); Baxter Healthcare SA, Glattpark (Opifkon) (CH)

( * ) Notice: Subject to any disclaimer, the term of this patent is extended or adjusted under 35 U.S.C. 154(b) by 530 days.

(21) Appl. No.: 12/105,213

(22) Filed: Apr. 17, 2008

(65) Prior Publication Data

US 2009/0017124 A1 Jan. 15, 2009

Related U.S. Application Data

(60) Provisional application No. 60/938,123, filed on May 15, 2007, provisional application No. 60/912,320, filed on Apr. 17, 2007.

(51) Int. Cl.
*A61K 9/50* (2006.01)
*A61K 38/28* (2006.01)

(52) U.S. Cl.
CPC . *A61K 9/50* (2013.01); *A61K 38/28* (2013.01); *A61K 9/5031* (2013.01)
USPC .......................................... 424/489; 424/490

(58) Field of Classification Search
CPC ........................... A61K 9/0075; A61K 9/1688
See application file for complete search history.

(56) References Cited

U.S. PATENT DOCUMENTS

| | | |
|---|---|---|
| 4,179,337 A | 12/1979 | Davis et al. |
| 4,289,872 A | 9/1981 | Denkewalter et al. |
| 4,301,144 A | 11/1981 | Iwashita et al. |
| 4,530,840 A | 7/1985 | Tice et al. |
| 4,584,894 A | 4/1986 | Fogelberg |
| 4,640,835 A | 2/1987 | Shimizu et al. |
| 4,670,417 A | 6/1987 | Iwasaki et al. |
| 4,791,192 A | 12/1988 | Nakagawa et al. |
| 4,853,462 A | 8/1989 | Hostetler et al. |
| 4,897,268 A | 1/1990 | Tice et al. |
| 4,904,479 A | 2/1990 | Illum |
| 4,996,689 A | 2/1991 | Samad |
| 5,075,109 A | 12/1991 | Tice et al. |
| 5,102,872 A | 4/1992 | Singh et al. |
| 5,138,045 A | 8/1992 | Cook et al. |
| 5,149,543 A | 9/1992 | Cohen et al. |
| 5,213,812 A | 5/1993 | Ruiz |
| 5,218,105 A | 6/1993 | Cook et al. |
| 5,229,490 A | 7/1993 | Tam |
| 5,334,711 A | 8/1994 | Sproat et al. |
| 5,360,610 A | 11/1994 | Tice et al. |
| 5,384,133 A | 1/1995 | Boyes et al. |
| 5,417,986 A | 5/1995 | Reid et al. |
| 5,422,120 A | 6/1995 | Kim |
| 5,459,255 A | 10/1995 | Cook et al. |
| 5,482,927 A | 1/1996 | Maniar et al. |
| 5,543,158 A | 8/1996 | Gref et al. |
| 5,578,709 A | 11/1996 | Woiszwillo |
| 5,599,719 A | 2/1997 | Woiszwillo et al. |
| 5,627,053 A | 5/1997 | Usman et al. |
| 5,654,010 A | 8/1997 | Johnson et al. |
| 5,665,428 A | 9/1997 | Cha et al. |
| 5,672,695 A | 9/1997 | Eckstein et al. |
| 5,716,824 A | 2/1998 | Beigelman et al. |
| 5,898,221 A | 4/1999 | Mizuhara et al. |
| 5,958,769 A * | 9/1999 | Roberts et al. ................. 435/375 |
| 5,981,719 A | 11/1999 | Woiszwillo et al. |
| 5,994,314 A | 11/1999 | Eljamal et al. |
| 6,001,311 A | 12/1999 | Brennan |
| 6,042,792 A | 3/2000 | Shefer et al. |
| 6,077,833 A | 6/2000 | Bennett et al. |
| 6,090,925 A | 7/2000 | Woiszwillo et al. |
| 6,107,094 A | 8/2000 | Crooke |
| 6,197,584 B1 | 3/2001 | Bennett et al. |
| 6,252,055 B1 | 6/2001 | Relton et al. |
| 6,267,958 B1 | 7/2001 | Andya et al. |
| 6,268,053 B1 | 7/2001 | Woiszwillo et al. |
| 6,290,991 B1 | 9/2001 | Roser et al. |
| 6,303,582 B1 | 10/2001 | Eljamal et al. |
| 6,319,906 B1 | 11/2001 | Bennett et al. |
| 6,458,387 B1 | 10/2002 | Scott et al. |
| 6,506,559 B1 | 1/2003 | Fire et al. |
| 6,573,099 B2 | 1/2003 | Graham |

(Continued)

FOREIGN PATENT DOCUMENTS

| | | |
|---|---|---|
| CA | 2482448 A1 | 10/2003 |
| EP | 248531 | 12/1987 |

(Continued)

OTHER PUBLICATIONS

Kingston, et al. (1999) Transfection and Expression of Cloned DNA. Curr. Prot. Immun., Unit 10.13:1-9.*
Jiang, et al. (2000) The Role of Cell Surface Receptors in the Activation of Human B Cells by Phosphorothioate Oligonucleotides, The Journal of Immunology, v.165:1438-45.*
Guo et al., Transgenic Research, 16:829-834 (2007).
International Search Report and Written Opinion from PCT/US2008/060669 dated Mar. 23, 2009.
Li et al., "Stability and release characteristics of poly(D,L-lactide-co-glycolide) encapsulated CaPi-DNA coprecipitation," International Journal of Pharmaceutics 269:61-70 (2004).

(Continued)

*Primary Examiner* — Jennifer McDonald
(74) *Attorney, Agent, or Firm* — Marshall, Gerstein & Borun LLP

(57) ABSTRACT

The present disclosure is related to microparticle compositions, in which the microparticles are made of nucleic acids and non-polymeric cations, which are suitable for administration to moist or aqueous target locations (e.g., the lung tissue), where the substantially spherical nucleic acid microparticles release the nucleic acids through dissolution, allowing the released nucleic acids to freely interact with the target cells.

13 Claims, 15 Drawing Sheets

(56) References Cited

U.S. PATENT DOCUMENTS

| | | |
|---|---|---|
| 6,616,949 B2 | 9/2003 | Jonsson et al. |
| 6,630,169 B1 | 10/2003 | Bot et al. |
| 6,645,525 B1 | 11/2003 | Woiszwillo et al. |
| 6,849,259 B2 | 2/2005 | Haurum et al. |
| 6,875,432 B2 | 4/2005 | Liu et al. |
| 7,056,704 B2 | 6/2006 | Tuschl et al. |
| 7,078,196 B2 | 7/2006 | Tuschl et al. |
| 7,132,100 B2 | 11/2006 | Oliver et al. |
| 8,075,919 B2 | 12/2011 | Brown et al. |
| 2001/0002261 A1 | 5/2001 | Morrison et al. |
| 2002/0009453 A1 | 1/2002 | Haurum et al. |
| 2002/0045571 A1 | 4/2002 | Liu et al. |
| 2002/0136719 A1 | 9/2002 | Shenoy et al. |
| 2003/0059474 A1 | 3/2003 | Scott et al. |
| 2004/0022081 A1 | 2/2004 | Erickson et al. |
| 2004/0043076 A1 | 3/2004 | Dulieu et al. |
| 2004/0110296 A1 | 6/2004 | Vargeese et al. |
| 2004/0171033 A1 | 9/2004 | Baker et al. |
| 2004/0185091 A1 | 9/2004 | Truong et al. |
| 2004/0186071 A1 | 9/2004 | Bennett et al. |
| 2004/0197324 A1 | 10/2004 | Liu et al. |
| 2004/0198640 A1 | 10/2004 | Leake et al. |
| 2004/0219224 A1 | 11/2004 | Yakovlevsky et al. |
| 2004/0249178 A1 | 12/2004 | Vargeese et al. |
| 2005/0053666 A1 | 3/2005 | Tzannis et al. |
| 2005/0058982 A1 | 3/2005 | Han et al. |
| 2005/0107325 A1 | 5/2005 | Manoharan et al. |
| 2005/0119214 A1 | 6/2005 | Manoharan et al. |
| 2005/0119470 A1 | 6/2005 | Manoharan et al. |
| 2005/0142206 A1* | 6/2005 | Brown et al. ............ 424/490 |
| 2005/0158303 A1 | 7/2005 | Liu et al. |
| 2005/0175603 A1 | 8/2005 | Liu et al. |
| 2005/0180967 A1 | 8/2005 | Haurum et al. |
| 2005/0186591 A1 | 8/2005 | Bumcrot et al. |
| 2005/0202072 A1 | 9/2005 | Ruch-Rasmussen et al. |
| 2005/0288244 A1 | 12/2005 | Manoharan et al. |
| 2006/0000882 A1 | 1/2006 | Darzinskas |
| 2006/0002862 A1 | 1/2006 | Truong-Le et al. |
| 2006/0008822 A1 | 1/2006 | Manoharan et al. |
| 2006/0018971 A1 | 1/2006 | Scott et al. |
| 2006/0035254 A1 | 2/2006 | Manoharan et al. |
| 2006/0127395 A1 | 6/2006 | Arvinte et al. |
| 2006/0182740 A1 | 8/2006 | Yang et al. |
| 2006/0234973 A1 | 10/2006 | Fitzgerald et al. |
| 2006/0240556 A1 | 10/2006 | Cibelli |
| 2006/0264396 A1 | 11/2006 | Min et al. |
| 2006/0276425 A1 | 12/2006 | Mourich et al. |
| 2007/0004667 A1 | 1/2007 | McSwiggen et al. |
| 2007/0023776 A1 | 2/2007 | Zakgeym et al. |
| 2007/0026079 A1 | 2/2007 | Herlands et al. |
| 2007/0065440 A1 | 3/2007 | Tomlinson et al. |
| 2007/0072904 A1 | 3/2007 | Lin et al. |
| 2007/0082845 A1 | 4/2007 | Connor et al. |
| 2007/0122411 A1 | 5/2007 | Matheus et al. |
| 2007/0161589 A1 | 7/2007 | Bennett et al. |
| 2007/0161595 A1 | 7/2007 | Bumcrot et al. |
| 2007/0172475 A1 | 7/2007 | Matheus et al. |
| 2007/0172479 A1 | 7/2007 | Warne et al. |
| 2007/0173476 A1 | 7/2007 | Leake et al. |
| 2007/0213292 A1 | 9/2007 | Stoffel et al. |
| 2007/0275465 A1 | 11/2007 | Woppmann et al. |
| 2007/0275914 A1 | 11/2007 | Manoharan et al. |
| 2007/0298445 A1 | 12/2007 | Boyd et al. |
| 2008/0026068 A1 | 1/2008 | Brown et al. |
| 2008/0039414 A1 | 2/2008 | McSwiggen et al. |
| 2008/0039415 A1 | 2/2008 | Stewart et al. |
| 2010/0310670 A1 | 12/2010 | Okada et al. |

FOREIGN PATENT DOCUMENTS

| | | |
|---|---|---|
| EP | 0564061 B1 | 10/1993 |
| EP | 0936902 | 8/1999 |
| EP | 0957926 | 11/1999 |
| EP | 1144623 | 10/2001 |
| EP | 1173151 B1 | 1/2002 |
| EP | 1173550 | 1/2002 |
| EP | 0975334 | 2/2002 |
| EP | 1283720 B1 | 2/2003 |
| EP | 1431347 A1 | 6/2004 |
| EP | 1801123 A2 | 6/2004 |
| EP | 1471034 A2 | 10/2004 |
| EP | 1614751 | 1/2006 |
| EP | 0907378 B1 | 2/2006 |
| FR | 2803206 | 7/2001 |
| JP | 2006219455 | 8/2006 |
| WO | WO-89/04239 | 5/1989 |
| WO | WO-91/03162 | 3/1991 |
| WO | WO-92/07065 | 4/1992 |
| WO | WO-93/15187 | 8/1993 |
| WO | WO-93/21259 | 10/1993 |
| WO | WO-93/23569 | 11/1993 |
| WO | WO-94/24263 | 10/1994 |
| WO | WO-95/06731 | 3/1995 |
| WO | WO-95/11910 | 5/1995 |
| WO | WO-96/03978 | 2/1996 |
| WO | WO-96/08289 | 3/1996 |
| WO | WO-97/26270 | 7/1997 |
| WO | WO-97/45140 | 12/1997 |
| WO | WO-98/13526 | 4/1998 |
| WO | WO-98/28317 | 7/1998 |
| WO | WO-99/54459 | 10/1999 |
| WO | WO-00/62759 | 10/2000 |
| WO | WO-01/28524 | 4/2001 |
| WO | WO-01/89563 | 11/2001 |
| WO | WO-02/28370 A1 | 4/2002 |
| WO | WO-02/39985 A1 | 5/2002 |
| WO | WO-02/072636 | 9/2002 |
| WO | WO-02/096457 | 12/2002 |
| WO | WO-03/000014 | 1/2003 |
| WO | WO-03/099228 | 12/2003 |
| WO | WO-2004/001007 | 12/2003 |
| WO | WO-2004/058156 | 7/2004 |
| WO | WO-2004/060343 | 7/2004 |
| WO | WO-2005/051355 | 6/2005 |
| WO | WO-2005/077414 | 8/2005 |
| WO | WO-2005/008443 | 9/2005 |
| WO | WO-2005/112894 | 12/2005 |
| WO | WO-2005/123131 | 12/2005 |
| WO | WO-2006/031560 | 3/2006 |
| WO | WO-2006/065746 | 6/2006 |
| WO | WO-2006/072527 | 7/2006 |
| WO | WO-2006/105361 | 10/2006 |
| WO | WO-2006/110688 | 10/2006 |
| WO | WO-2006/110813 | 10/2006 |
| WO | WO-2006/112838 | 10/2006 |
| WO | WO-2006/123800 | 11/2006 |
| WO | WO-2006/126600 | 11/2006 |
| WO | WO-2006/128141 | 11/2006 |
| WO | WO-2006/128739 | 12/2006 |
| WO | WO-2007/029361 A1 | 3/2007 |
| WO | WO-2007/076062 | 7/2007 |

OTHER PUBLICATIONS

M. Manoharan Antisense & Nucleic Acid Drug Development 12:103-128 (2002).

Pallisner, et al., Nature 439:89-94 (2006).

Skobridis et al., ARKIVOC (vi) 459-469 (2005).

Swenson, et al., Stem Cells, 25:2593-2600 (2007).

Wolfram, et al., Nature Biotechnology 25:1149-1157 (2007).

Khan et al., Sustained polymeric delivery of gene silencing antisense ODNs, siRNA, DNAzymes and Ribozymes: In vitro and in vivo studies. *J. Drug Targeting*, 12(6): 393-404 (2004).

Diehl et al., A good practice guide to the administration of substances and removal of blood, including routes and volumes, *J. Appl. Toxicol.*, 21: 15-33 (2001).

Falkenberg et al., Polyclonal and monoclonal antibodies as reagents in biochemical and in clinical-chemical analysis, *J. Clin. Chem. Biochem.*, 22: 867-82 (1984).

Huber et al., Spatial structure of immunoglobulin molecules. *Klin. Wochenscher.*, 58: 1217-31 (1998).

(56) References Cited

OTHER PUBLICATIONS

Moghimi et al., Chemical camouflage of nanospheres with a poorly reactive surface: towards development of stealth and target-specific nanocarriers, *Biochim. Biophys. Acta*, 1590: 131-9 (2002).
Morita et al., Formation and isolation of spherical fine protein microparticles through lyophilization of protein-poly(ethylene glycol) aqueous mixture, *Pharma. Res.*, 17(11): 1367-63 (2000).
Sinha et al., Biodegradable microspheres for protein delivery, *J. Controlled Release*, 90(3): 261-80 (2003).
Non-Final Office Action issued in connection with U.S. Appl. No. 10/894,430, dated Feb. 27, 2008.
Final Office Action issued in connection with U.S. Appl. No. 10/894,430, dated Aug. 18, 2009.
Non-Final Office Action issued in connection with U.S. Appl. No. 10/894,430, dated Dec. 19, 2010.
Notice of Allowance issued in connection with U.S. Appl. No. 10/894,430, dated Sep. 13, 2011.
Non-Final Office Action issued in connection with U.S. Appl. No. 11/127,704, dated Jul. 17, 2006.
Non-Final Office Action issued in connection with U.S. Appl. No. 11/127,704, dated Dec. 12, 2007.
Non-Final Office Action issued in connection with U.S. Appl. No. 11/127,704, dated Jun. 2, 2009.
Final Office Action issued in connection with U.S. Appl. No. 11/127,704, dated Jun. 14, 2012.
Notice of Allowance issued in connection with U.S. Appl. No. 11/127,704, dated Aug. 14, 2012.
International Search Report issued in connection with International Application No. PCT/US2005/016651, dated Sep. 5, 2005.
US 5,849,884, 12/1998, Woiszwillo et al. (withdrawn)

* cited by examiner

95% < 3 microns
by number

Aerodynamic Diameter (micron)

FIG. 3A

95% < 3 microns
by volume

Aerodynamic Diameter (micron)

FIG. 16

NUCLEIC ACID MICROPARTICLES FOR PULMONARY DELIVERY

This application claims priority of U.S. Provisional Patent Application No. 60/938,123 filed May 15, 2007 and U.S. Provisional Patent Application No. 60/912,320 filed Apr. 17, 2007, the disclosures of which are incorporated herein by reference in their entireties.

FIELD OF THE DISCLOSURE

The present disclosure generally relates to preparation of nucleic acid microparticles. More particularly, the disclosure relates to pulmonary delivery of spherical nucleic acid-based microparticles that have been prepared using aqueous conditions without the use of a polymeric cation.

BACKGROUND ART

Microparticles are solid or semi-solid particles having a diameter of less than one millimeter, more preferably less than 100 microns, which can be formed of a variety of materials, including synthetic polymers, proteins, and polysaccharides.

Exemplary polymers used for the formation of microspheres include homopolymers and copolymers of lactic acid and glycolic acid (PLGA) as described in U.S. Pat. No. 5,213,812 to Ruiz, U.S. Pat. No. 5,417,986 to Reid et al., U.S. Pat. No. 4,530,840 to Tice et al., U.S. Pat. No. 4,897,268 to Tice et al., U.S. Pat. No. 5,075,109 to Tice et al., U.S. Pat. No. 5,102,872 to Singh et al., U.S. Pat. No. 5,384,133 to Boyes et al., U.S. Pat. No. 5,360,610 to Tice et al., and European Patent Application Publication Number 248,531 to Southern Research Institute; block copolymers such as tetronic 908 and poloxamer 407 as described in U.S. Pat. No. 4,904,479 to Illum; and polyphosphazenes as described in U.S. Pat. No. 5,149,543 to Cohen et al. Microparticles produced using polymers such as these exhibit a poor loading efficiency and are often only able to incorporate a small percentage (typically less than 10%) of the drug of interest into the polymer structure.

These microparticles have a wide particle size distribution, often lack uniformity, and may not exhibit desired release kinetics. Furthermore, the polymers used are dissolved in organic solvents in order to foil these microparticles. They must therefore be produced in special facilities designed to handle organic solvents. These organic solvents could adversely affect the drug contained in the microparticles. Residual organic solvents could be toxic when administered to humans or animals.

In addition, the available microparticles are rarely of a size sufficiently small to be useful for administration by inhalation. For example, microparticles prepared using polylactic glycolic acid (PLGA) are large and have a tendency to aggregate. A size selection step, resulting in product loss and cost increase, is necessary.

Microparticles prepared using lipids to encapsulate target drugs are known. For example, lipids arranged in bilayer membranes surrounding multiple aqueous compartments to form particles may be used to encapsulate water soluble drugs for subsequent delivery, as described in U.S. Pat. No. 5,422,120 to Sinil Kim. These particles are generally greater than 10 microns in size and are designed for intra-articular, intrathecal, subcutaneous and epidural administration. Alternatively, liposomes have been used for intravenous delivery of small molecules. Liposome technology has been hindered by problems including purity of lipid components, possible toxicity, vesicle heterogeneity and stability, excessive uptake and manufacturing or shelf-life difficulties.

An objective for the medical community is the delivery of nucleic acids to the cells of a subject, including but not limited to an animal or a mammal, for treatment. For example, nucleic acids can be delivered to cells in culture (in vitro) relatively efficiently, but nucleases result in a high rate of nucleic acid degradation when nucleic acids are delivered to animals (in vivo).

In addition to protecting nucleic acid from nuclease digestion, a desirable nucleic acid delivery vehicle would exhibit low toxicity, be efficiently taken up by cells and have a well-defined, readily manufactured formulation. As shown in clinical trials, viral vectors for nucleic acid delivery can result in a severely adverse, even fatal, immune response in vivo. In addition, this method has the potential to have mutagenic effects in vivo. Delivery by enclosing nucleic acid in lipid complexes (such as liposomes or cationic lipid complexes) has been generally ineffective in vivo and can have toxic effects. Complexes of nucleic acids with various polymers or with peptides have shown inconsistent results and the toxicity of these formulations has not yet been resolved. Nucleic acids have also been encapsulated in polymer matrices for delivery but in these cases the particles have a wide size range and the effectiveness for therapeutic applications has not been demonstrated.

Therefore, there is a need for addressing nucleic acid delivery issues, and providing effective nucleic acid formulations. Also, there is an ongoing need for development of microparticles and to new methods for making microparticles. Microparticles and their preparation have been described in U.S. Pat. No. 6,458,387 to Scott et al., U.S. Pat. No. 6,268,053, U.S. Pat. No. 6,090,925, U.S. Pat. No. 5,981,719 and No. 5,599,719 to Woiszwillo et al., and U.S. Pat. No. 5,578,709 to Woiszwillo, as well as U.S. Publication No. 20050142206 and U.S. Publication No. 20060018971. Each of the foregoing references and all other references identified therein and herein are incorporated herein by reference. It is noted, however, that these microparticles previously described typically were prepared using a polymeric cation such as, for example, poly-L-lysine or poly L-ornithine. While the use of such polymeric cations produces excellent results with microparticles having nucleic acid loading of 20 weight percent to 100 weight percent, and having an average particle size of not greater than about 50 microns, typically, the polymeric cations render these microparticles relatively insoluble in water. Therefore, these microparticles of polymeric cations and nucleic acids are not suitable for releasing nucleic acids at target locations. While such microparticles may be taken up wholly by certain target cells and/or other cells (e.g., macrophages) through endocytosis, these microparticles do not dissolve at a target site that has an aqueous environment and hence the nucleic acids in these microparticles cannot interact freely with such target cells.

As such, there remains a need for microparticle preparations that readily dissolve at target locations that are in a moist or aqueous environment such as, for example, the lungs, nasal membranes, mouth, throat, stomach, intestines, vagina, any parts of the respiratory system, open wounds (e.g., lesions, lacerations, surgical wounds, burn wounds), any mucosal membranes, any epithelial cells, any vasculature, and the like to release nucleic acids that can freely interact with the target cells.

SUMMARY OF THE DISCLOSURE

The present disclosure is related to compositions in which microparticles are made of nucleic acids and non-polymeric cations, which are suitable for administration to moist or aqueous target locations (e.g., lung tissue). The microparticles are substantially spherical nucleic acid microparticles that release the nucleic acids through dissolution at the target location, allowing the released nucleic acids to freely interact with the target cells.

In one example there is provided a composition comprising a plurality of nucleic acid microparticles comprising one or more nucleic acids and one or more non-polymeric cations wherein the microparticles are substantially spherical, water-soluble at ambient temperature and have an average particle size of 0.5 microns to 5 microns, wherein the microparticles are free of polymeric polycations and free of non-nucleic acid matrices, cores, or envelopes.

For example, the microparticles comprise between about 4 weight % to about 10 weight % of the one or more non-polymeric cations. Alternatively, the microparticles comprise about 2 weight %, about 3 weight %, about 4 weight %, about 5 weight %, about 6 weight %, about 7 weight %, about 8 weight %, about 9 weight %, about 10 weight %, about 11 weight %, about 12 weight %, about 13 weight %, about 14 weight %, or about 15 weight %.

The inorganic cation may be selected from the group consisting of $Ca^{2+}$, $Zn^{2+}$, $Mn^{2+}$, $Na^+$, $Ba^{2+}$, $K^+$, $Mg^{2+}$, $Co^{2+}$, $Cu^{2+}$, $Fe^{2+}$, $Fe^{3+}$, $Al^{3+}$, and $Li^+$, or a combination of two or more thereof.

In some examples, the nucleic acid may be an antisense oligonucleotide or it may be an siRNA.

In some examples, the microparticles in the composition do not aggregate with each other.

In some examples, a majority (e.g., 75% or more, 80% or more, 85% or more, 90% or more, 95% or more, as measured by number and/or volume) of the nucleic acid microparticles has an aerodynamic diameter of 3 microns or less.

In some examples, a majority (e.g., 50% or more, 55% or more, 60% or more, 65% or more, 70% or more, 75% or more, 80% or more, 85% or more, 90% or more, 95% or more, as measured by weight) of the solid content of the nucleic acid microparticle compositions disclosed herein is nucleic acid.

Another exemplary composition comprises a plurality of nucleic acid microparticles comprising one or more nucleic acids and one or more non-polymeric cations wherein the microparticles are substantially spherical, water-soluble at ambient temperature and have an average particle size of 0.5 microns to 5 microns, wherein said microparticles comprise less than 6 weight % of the one or more non-polymeric cations and greater than 60 weight % of the one or more nucleic acids.

Also provided herein are methods of making nucleic acid microparticles comprising forming reaction mixture (e.g., a solution or a dispersion) comprising one or more nucleic acids and one or more non-polymeric cations, and cooling the solution or dispersion to form a plurality of nucleic acid microparticles. The reaction mixture can be formed by mixing a nucleic acid solution with a non-polymeric cation solution. Exemplary non-polymeric cation solutions include $CaCl_2$, NaCl, $MgCl_2$, $MnCl_2$, $ZnCl_2$, and LiCl at a concentration of 0.01M to 5M. The reaction mixture may be incubated for a sufficient time, optionally with heating and/or cooling, to allow a clear solution to form prior to the formation of the nucleic acid microparticles. In one aspect, the cooling process does not freeze the reaction mixture, but typically cool the solution or dispersion to a temperature of from about 1 to about 10° C., until a population of substantially spherical microparticles containing nucleic acid and non-polymeric cation is formed. The methods are efficient in that they allow the majority (e.g., 60% or more, 65% or more, 70% or more, 75% or more) of the nucleic acid in the reaction mixture to be incorporated in the nucleic acid microparticles.

In certain aspects, the method may further comprise the step of adding to the reaction mixture, prior to the formation of the nucleic acid microparticles, a non-ionic polymer in the form of a solid or a solution. Exemplary polymers include PEG, PVP, and mixtures thereof (e.g., without limitation, a 1:1 ratio of PEG:PVP).

In the method, the incubation temperature may be from about 25° C. to about 90° C., and as high as about 100° C.

In the method, the incubation time may be from about 1 minute to about 1 hour.

The method may further comprise isolating and/or washing the nucleic acid microparticles. The microparticles may be isolated by sedimentation using centrifugation. The washing may be carried out using a non-solvent for the nucleic acid microparticles. The non-solvent can be aqueous, but not water alone.

In additional aspects, the method involves lyophilizing the nucleic acid microparticles to produce a dry nucleic acid powder.

Preferably, the method produces a microsphere population that contains microparticles that are substantially spherical.

In other embodiments, the method produces a microsphere population that is substantially water-soluble at ambient temperature.

In still other embodiments, the method produces a population of microparticles that have an average particle size of about between about 0.5 microns to about 3 microns.

In some examples, the method produces microparticles that comprise at least 50 weight % nucleic acid.

In still other examples, the method produces microparticles that comprise between about 55 weight % to about 95 weight % nucleic acid, such as about 65 weight % to about 85 weight %, or about 70 weight % to about 80 weight %.

In some examples the microparticles produced comprise between about 3 weight % to about 10 weight % non-polymeric cation.

In certain aspects the method is performed such that the pH range of the reaction mixture for forming the microparticles is between about 3 to about 10.

In specific examples, the non-polymeric cation solution is a $CaCl_2$ solution.

In other examples, the non-polymeric cation solution is a $ZnCl_2$ solution.

In still other examples, the non-polymeric cation solution is a $MgCl_2$ solution.

In still other examples, the non-polymeric cation solution is a NaCl solution.

Where the cation solution is $CaCl_2$, in some specific examples it may be provided at a concentration of 1.25M, the incubation temperature is 75° C. and the microparticles produced have a size of between 1-2 microns. In other examples, the $CaCl_2$ is provided at a concentration of 1M, the incubation temperature is 75° C. and the microparticles produced have a size of between 1.3-2.3 microns.

In these methods, one exemplary incubation temperature is 70° C. In such an example, microparticles formed have a size of between about 2 to 2.6 microns when the $CaCl_2$ concentration is about 0.67M.

In preferred examples, the method produces microparticles that have a size of between about 2 to 2.6 microns when the $CaCl_2$ concentration is between about 0.15M and 0.75M.

Also described is a microparticle composition prepared according to the methods discussed above.

Another example describes an aerosol composition that comprises the compositions described herein.

Methods of treatment are described, including for example, a method of treating a subject in need thereof comprising administering to said subject an aerosol composition as described herein.

Also described is a nucleic acid microparticle comprising one or more nucleic acids and one or more non-polymeric cations, wherein the microparticle is free of polymeric polycations and free of non-nucleic acid matrices, cores, or envelopes.

Also provided are methods of making nucleic acid microparticles comprising forming a solution or a dispersion comprising one or more nucleic acids, one or more non-polymeric cations, and one or more non-ionic polymers; and cooling the solution or dispersion to form a plurality of substantially spherical nucleic acid microparticles, wherein the microparticles are free of polymeric polycations and free of non-nucleic acid matrices, cores, or envelopes. In one aspect methods utilize one or more nucleic acids is modified to include a hydrophobic moiety, and in specific aspect, the hydrophobic moiety is cholesterol.

In still another aspect, the methods include a molar ratio of the one or more non-polymeric cations to the one or more nucleic acids is 50,000:1 or less.

In yet another aspect, the cooling step is carried out at a rate of 0.5° C./min, a rate of 0.75° C./min, and a rate of 0.8° C./min. In certain aspects, the cooling step ends at about 4° C., at about 0° C., or at about −5° C.

The invention also provides methods of making nucleic acid microparticles comprising incubating a mixture of cholesterol-modified nucleic acid, water soluble polymer and polyvalent cation, and cooling the mixture over time at a rate sufficient to form microparticles. In various aspects, the cooling step is carried out at a rate of 0.5° C./min, at a rate of 0.75° C./min or at a rate of 0.8° C./min, and in other aspects, the cooling step ends at about 4° C., at about 0° C., or at about −5° C.

In one aspect, of methods disclosed, the nucleic acid is an inhibitory RNA molecule, and in one aspect, the nucleic acid is siRNA.

In other aspects, of the methods, the polyvalent cation is any polyvalent cation as described herein, and in specific aspects, the polyvalent cation is $Mg^{++}$ or $Ca^{++}$.

In yet other aspects, of the methods, the water soluble polymer is polyethylene glycol, or the water soluble polymer is a mixture of polyethylene glycol (PEG) and polyvinylpyrrolidone (PVP).

In certain methods, the mixture is incubated at room temperature, at 37° C., or at 65° C., and in other aspects, the incubating step is carried out from about 5 minutes to about 10 minutes.

In still another aspect, of the methods, the water soluble polymer is present in the mixture from about 12.5% (w/v) to about 25% (w/v), and in a specific aspect, the water soluble polymer is present in the mixture at about 12.5% (w/v), at about 16.7% (w/v), or at about 20% (w/v).

In yet other aspects, the polyvalent cation is present in the mixture at about 7.5 mM to greater than 1 M, and in specific aspects, the polyvalent cation is present in the mixture at about 10 mM to about 20 mM, to about 25 mM, or to about 35 mM, and in still another specific aspect, the polyvalent cation is present in the mixture at about 25 mM.

The invention further provides microparticles produced by any of the method disclosed herein.

In another embodiment, the invention provides methods for delivering a microparticle to target mucosa comprising the step of contacting target mucosa with a microparticle as described herein an amount effective to penetrate and act on or within said target mucosa. In various aspects, the target mucosa is selected from the group consisting of buccal mucosa, esophageal mucosa, gastric mucosa, intestinal mucosa, olfactory mucosa, oral mucosa, bronchial mucosa, uterine mucosa, and endometrium.

BRIEF DESCRIPTION OF THE DRAWINGS

The following drawings form part of the present specification and are included to further illustrate aspects of the present disclosure. The disclosure may be better understood by reference to the drawings in combination with the detailed description of the specific examples presented herein.

FIGS. 3A-B show that the aerodynamic diameter distribution of the nucleic acid (e.g., antisense oligonucleotides) microparticles as measured by number (FIG. 3A) is consistent with, but not identical to, that measured by volume (FIG. 3B). Both measurements show that at least 95% of the microparticles have an aerodynamic diameter of less than 3 microns.

FIG. 4A shows nucleic acid microparticles with a mass medium aerodynamic diameter (MMAD) of 2.9 microns, a geometric standard deviation (GSD) of 1.5, an emitted dose of 73%, and a fine particle fraction FPF (<8 micron or <5 microns) of 82% or greater of the emitted dose. FIG. 4B shows nucleic acid microparticles with an MMAD of 2.9 microns, an emitted dose of 85%, and a FPF (<8 micron or <5 microns) of 79% or greater.

FIG. 15 shows the aerodynamic diameter distribution of the nucleic acid (e.g., siRNA) microparticles as measured by number and volume. Both measurements show that at least 95% of the microparticles have an aerodynamic diameter of less than 3 microns.

FIG. 16 shows an exemplary NGI characterization pattern of the nucleic acid (e.g., siRNA) microparticles disclosed herein, with an MMAD of 2.6 microns, an emitted dose of 77%, and a FPF (<8 micron) of 78% or greater.

DETAILED DESCRIPTION OF EXAMPLES

Figure 1A:
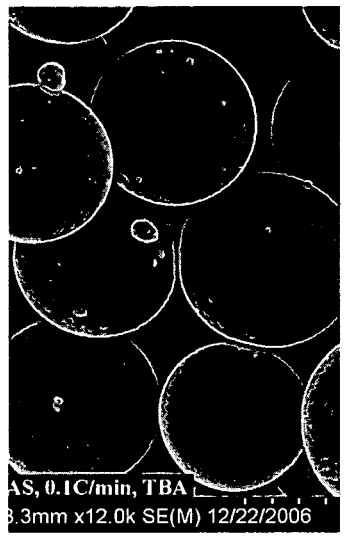
FIGS. 1A-D show the nucleic acid microparticles of different geometric sizes formed from identical reaction mixtures prior to cooling at a cooling rate of 0.1° C./min (FIG. 1A); 0.5° C./min (FIG. 1B); 1° C./min (FIG. 1C); 2° C./min (FIG. 1D); and 5° C./min (FIG. 1E).
Figure 1B:
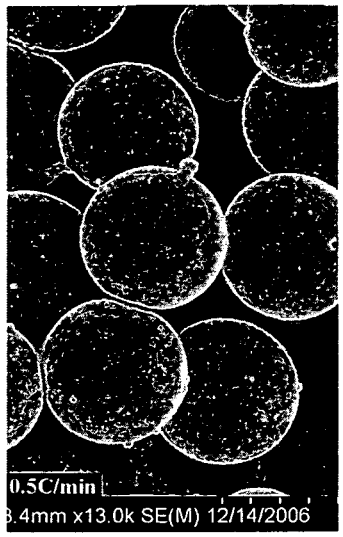
Figure 1C:
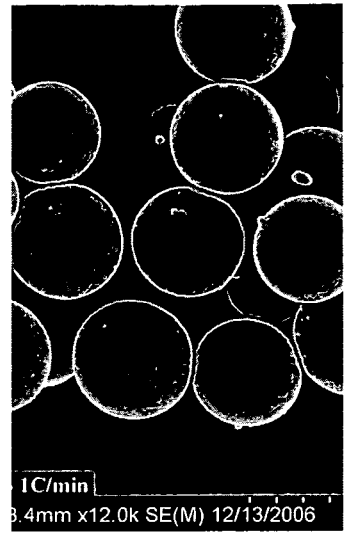
Figure 1D:
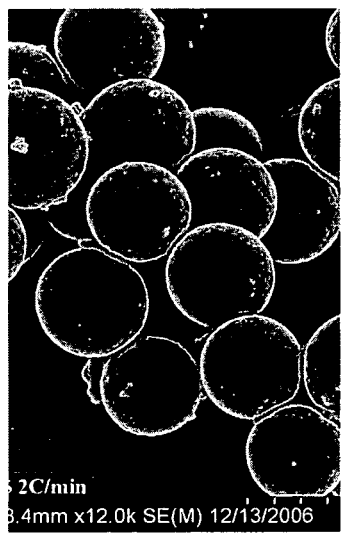
Figure 1E:
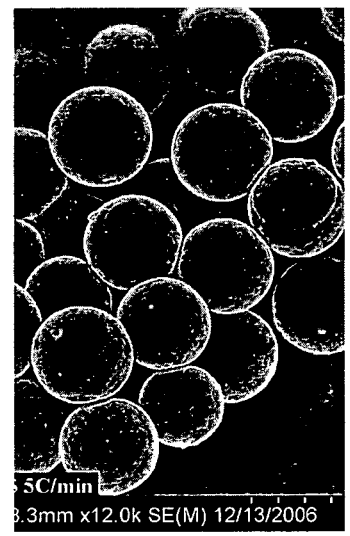
Figure 2A:
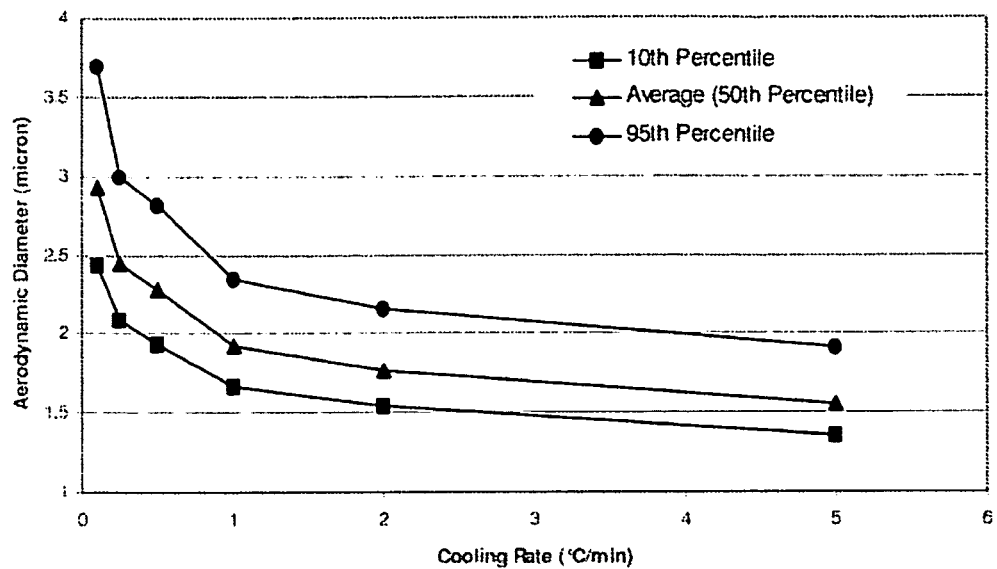
FIGS. 2A-B show a consistent reverse correlation between the aerodynamic diameter cut-off values of the nucleic acid microparticles at different percentiles and the cooling rate. The curve in FIG. 2B is identical to the middle curve in FIG. 2A.
Figure 2B:
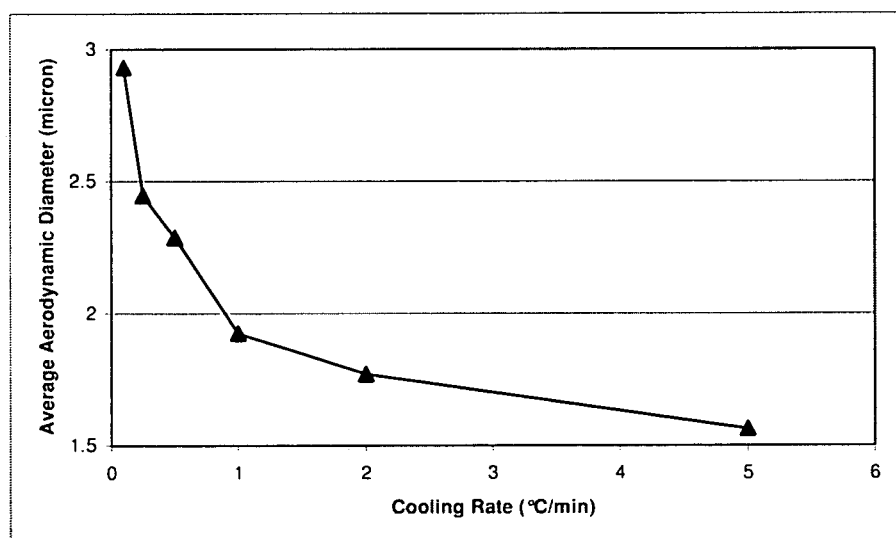
Figure 4A:
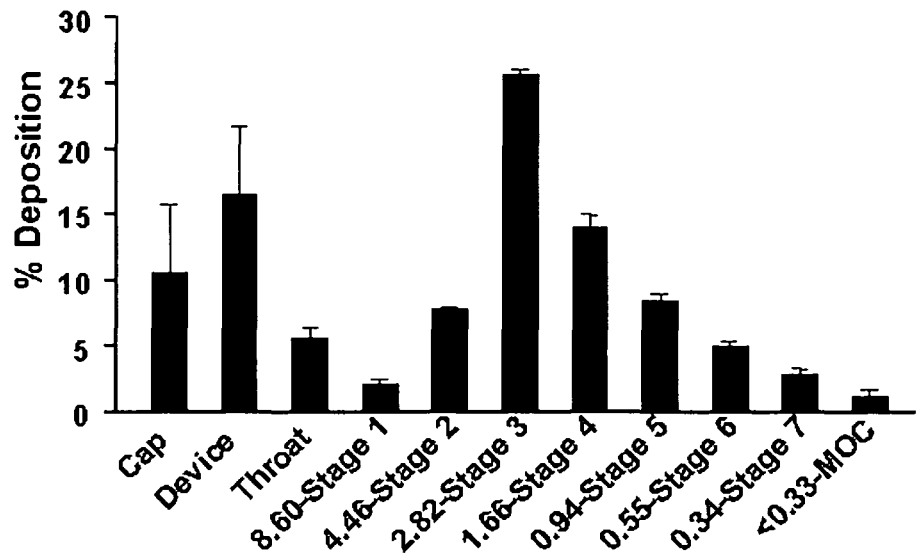
FIGS. 4A-B show the next-generation impactor (NGI) characterization patterns of the nucleic acid (e.g., antisense oligonucleotides) microparticles disclosed herein.
Figure 4B:
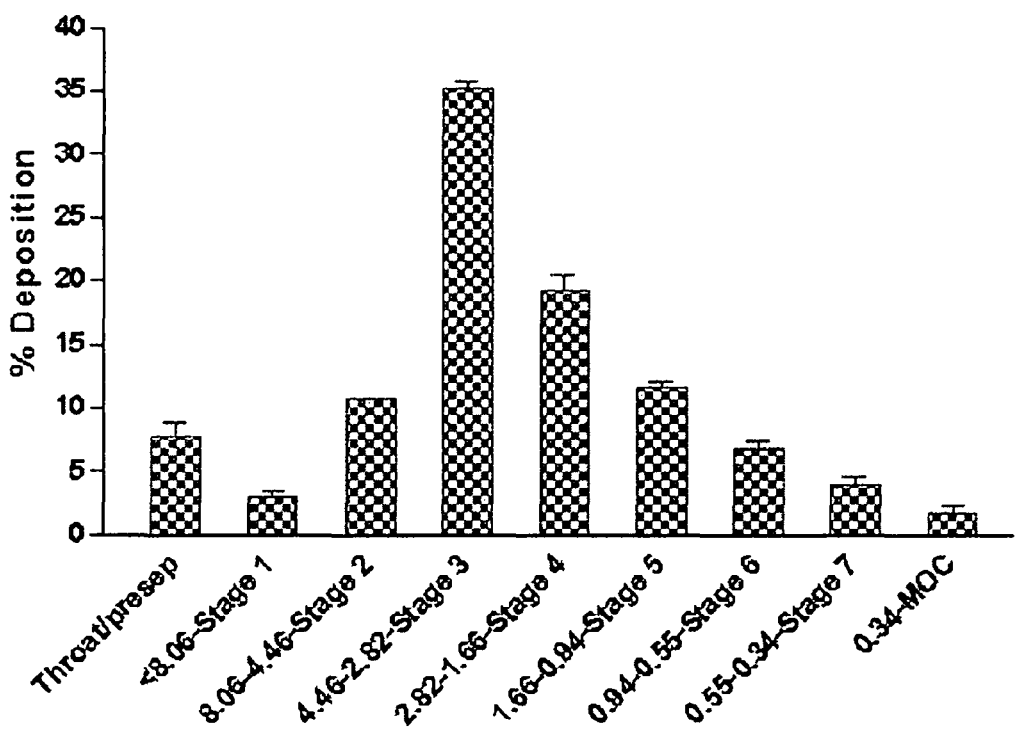

As discussed herein above, microparticles of nucleic acids in combination with polymeric polycations such as those disclosed in U.S. Publication No. 20060018971 are water-insoluble, and are not suitable for delivery to moist or aqueous target locations. The content of the polymeric polycations in these microparticles is in the range of 6% or greater (e.g., 6-12%) by weight of the microparticles, potentially reducing the payload of nucleic acids therein. The present disclosure provides nucleic acid microparticle compositions that can be used to deliver nucleic acid molecules to moist or aqueous target locations such as the surfaces of the lung (e.g., through oral or nasal inhalation of dry powders and/or metered dose formulations). These compositions rapidly dissolve at the target location and release, at that target location, the nucleic acid molecules contained in the microparticle compositions. Non-polymeric cations are smaller in size than the polymeric polycations and in certain cases even smaller than the monomer unit of the polymeric polycations. The use of such smaller non-polymeric cations allows one to form microparticles that contain far less weight (typically less than 6%, and more typically in the order of 2-3% to 5%) of the cation in the final microparticle. This allows higher payloads of the nucleic acids to be delivered in the same amount (by weight) of the microparticles.

In general, the nucleic acids in the present disclosure (e.g., antisense oligonucleotides, small interfering RNAs) were mostly dissolved (reaction mixture being visibly clear) if not completely dissolved (reaction mixture being visibly hazy or cloudy) in a single-phase liquid medium (e.g., aqueous medium such as an aqueous buffer) in the presence of one or more solubilized non-polymeric cations (for example, $Ba^{2+}$, $Ca^{2+}$, $Mg^{2+}$, $Sr^{2+}$, $Zn^{2+}$, $Na^+$, $K^+$, $Li^+$, $Cu^{2+}$, $Fe^{2+}$, $Mn^{2+}$, $Fe^{3+}$, $Al^{3+}$) and one or more solubilized non-ionic polymers (e.g., polyethylene glycol (PEG) and/or polyvinylpyrrolidone (PVP)). The solubility of the dissolved nucleic acids was adjusted (e.g., by cooling the reaction solution, increasing the concentrations of the nucleic acids and/or the non-ionic polymers and/or the non-polymeric cations, and/or increasing or decreasing the pressure to which the reaction solution was subjected) such that the solubilized nucleic acid molecules aggregated together and co-solidified with the non-polymeric cations to form the nucleic acid microparticles, which were typically observed in the form of turbid suspendable dispersions. The nucleic acid microparticle formation was followed by further processing (e.g., centrifugation, washing, and/or lyophilization) to separate the nucleic acid microparticles from the reaction medium and the solubilized ingredients therein (e.g., the non-ionic polymers such as PEG and/or PVP). The resulting nucleic acid microparticles (such as in the form of a dry powder) were characterized (e.g., the size distribution was determined by scanning electron microscopy (SEM) and aerodynamic time-of-flight measurements using a TSI Aerosizer, the aerodynamic properties were determined in vitro using the Next Generation Impactor (NGI) and a Cyclohaler dry powder inhaler device, the integrity of the nucleic acids in the microparticles was determined by reverse phase (RP) HPLC for degradation).

Surprisingly, it was found that the nucleic acid microparticles could be formulated to have any one or more diameters in the range between 0.5 and 5 μm and/or be substantially spherical, and were readily soluble in water and/or physiological medium. Based on both the SEM and the Aerosizer data, the PROMAXX nucleic acid microparticles' size distribution was determined to be suitable for local delivery to any one or more areas of the lung and other areas of the respiratory system. In vitro assessment of aerodynamic properties of certain examples measured with the NGI resulted in a mass median aerodynamic diameter of, for example, 3.0 μm; a geometric standard deviation of, for example, 1.5 μm; an emitted dose of, for example, 73%, and a fine particle fraction (<8 micron) of, for example, 82%, but were not limited thereto. The data suggested that these microparticles were ideal for pulmonary mucosal deposition (e.g., local delivery to the lung). RP-HPLC data showed no significant changes in the nucleic acids post microparticle fabrication. Moreover, the nucleic acid microparticle formation methods resulted in little to no degradation of the nucleic acids incorporated in the nucleic acid microparticles or agglomeration there between.

The present disclosure thus provides nucleic acid microparticles that are characterized in that they are substantially spherical. When the microparticles are visualized using SEM, in one aspect, the nucleic acid microparticles are seen to be substantially non-porous and have smooth surfaces. As such, these microparticles pack more nucleic acid molecules in a limited space, making delivery of the nucleic acids more efficient and effective than porous microparticles having relatively low payloads. Also, the low porosity of the nucleic acid microparticles disclosed herein minimizes their surface areas, effectively shielding the majority of the nucleic acid molecules therein from exposure to elements of degradation, making the nucleic acids therein more storage-stable than those in porous microparticles. Additionally, another feature of the nucleic acid microparticles of the disclosure is that the microparticles have a typical nucleic acid loading in one aspect greater than 45%, and in other aspects of greater than 60% by weight and a non-polymeric cation content of 1 to 3% or greater, leaving no room for matrices of materials as found in other microparticles having various matrices of excipients (e.g., lipids, non-nucleic acid polymers, surfactants, carbohydrates). Indeed, the microparticles of the disclosure are such that the secondary, tertiary, and quaternary structures are principally attributed to the nucleic acid molecules in combination with the non-polymeric cations. As such, the exemplary microparticles of the disclosure may be described as being substantially free of non-cationic structural components other than nucleic acids, and being substantially free of for example lipids, sugars, hydrogel materials, and surfactants. The cationic component of the microparticles consists of one or more non-polymeric cations such as, for example, monovalent cations, divalent cations, trivalent cations, other polyvalent non-polymeric cations, organic non-polymeric cations of one, two, or more valency, and combinations of two or more thereof, which include, without limitation, lithium ions, sodium ions, potassium ions, zinc ions, barium ions, calcium ions, magnesium ions, serum ions, manganese ions, copper ions, iron ions, aluminum ions, ammonium ions, alkyl-ammonium ions, t-alkyl ammonium ions, dialkyl ammonium ions, trialkyl ammonium ions, tetraalkyl ammonium ions, and the like. Included in the class of non-polymeric cations are cationic monomers such as free basic amino acids (e.g., lysine, arginine, histidine, ornithine, citrulline, and optical isomers and stereoisomers thereof). The non-polymeric cations are provided in the form of aqueous-soluble hydroxides and salts that do not form water-insoluble precipitates with any non-nucleic acid ingredients in the reaction solution, the anions of the salts including monovalent anions, divalent anions, trivalent anions, other polyvalent non-polymeric anions, organic non-polymeric anions of one, two, or more valency, and combinations of two or more thereof (e.g., chlorides, acetates, carbonates, trichlorocarbonates, citrates, but not limited thereto). Non-polymeric cations used herein specifically exclude cationic lipids, cationic proteins, and cationic peptides. Cationic surfactants and phospholipids, as well as cationic molecules having a moiety of $(CH_2)_n$, where n is greater than 4 are also excluded from the term non-polymeric cations.

The nucleic acid microparticles are readily soluble in water and/or physiological medium (e.g., saline, PBS buffer, serum). For example, the nucleic acid microparticles have a solubility in deionized water of 0.1% by weight or greater, such as 0.5% or greater, 1% or greater, 2% or greater, 3% or greater, 5% or greater, 10% or greater, 20% or greater, at a temperature in the range of 20° C. to 40° C., such as 25° C. or 37° C. For any given nucleic acid microparticle composition of the disclosure, the geometric size distribution and/or the aerodynamic size distribution may independently or simultaneously be mono-modal, bimodal, or polymodal.

In order for a given composition to reach one or more predetermined areas (e.g., deep lung) or all areas of the lung, as is desirable in certain applications (e.g., lung infections), it is contemplated that the compositions have a polydispersed particle size distribution, for example, by mixing two or more groups of nucleic acid microparticles having different geometric size distributions and/or different aerodynamic size distributions. Non-limiting examples of geometric size distributions and/or aerodynamic size distributions include those distributed across one, two, or more ranges between any values such as 0.1 microns, 0.5 microns, 1 micron, 1.5 microns, 2 microns, 2.5 microns, 3 microns, 3.5 microns, 4 microns, 4.5 microns, 5 microns, 10 microns, and sub-ranges therein. Thus it is contemplated that a given composition may be prepared that has a distribution of particle sizes ranging from 1.5 microns to 3 microns, 1.5 microns to 5 microns, or 1.5 microns to 8 microns.

Methods, materials, and processes for the preparation of these nucleic acid microparticles and compositions containing such nucleic acid microparticles for storage and end uses are described in further detail below.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Thus, for example, the reference to a particular microparticle is a reference to one such microparticle or a plurality of such microparticles, including equivalents thereof known to one skilled in the art. Also, as used herein and in the claims, the terms "at least one" and "one or more" have the same meaning and include one, two, three or more. The following terms, unless otherwise indicated, shall be understood to have the following meanings when used in the context of the present disclosure.

Other than in the operating examples, or unless otherwise expressly specified, all of the numerical ranges, amounts, values and percentages such as those for quantities of materials, times, temperatures, reaction conditions, ratios of amounts, values for molecular weight (whether number average molecular weight $M_n$ or weight average molecular weight $M_w$), and others disclosed herein should be understood as modified in all instances by the term "about." Accordingly, unless indicated to the contrary, the numerical parameters set forth in the present disclosure and attached claims are approximations that may vary as desired. At the very least, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values inclusive of the recited values may be used.

"Formed from" and "formed of" denote open, language. As such, it is intended that a composition "formed from" or "formed of" a list of recited components be a composition comprising at least these recited components, and can further include other non-recited components during formulation of the composition.

Examples provided herein, including those following "such as" and "e.g.," are considered as illustrative only of various aspects of the present disclosure and embodiments thereof, without being specifically limited thereto. Any suitable equivalents, alternatives, and modifications thereof (including materials, substances, constructions, compositions, formulations, means, methods, conditions, etc.) known and/or available to one skilled in the art may be used or carried out in place of or in combination with those disclosed herein, and are considered to fall within the scope of the present disclosure.

A. Nucleic Acid Microparticles

"Microparticle" refers to a particulate that is solid (including substantially solid or semi-solid, but excluding gel, liquid and gas), having an average geometric particle size (sometimes referred to as diameter) of less than 1 mm, such as 200 microns or less, or 100 microns or less, or 10 microns or less. In one example, the particle size is 0.01 microns or greater, such as 0.1 microns or greater, or 0.5 microns or greater, or from 0.5 microns to 5 microns. Average geometric particle size may be measured by dynamic light scattering methods (such as photocorrelation spectroscopy, laser diffraction, low-angle laser light scattering (LALLS), medium-angle laser light scattering (MALLS)), light obscuration methods (such as Coulter analysis method), or other methods (such as rheology, light or electron microscopy). Microparticles for pulmonary delivery will have an aerodynamic particle size determined by time of flight measurements, Andersen Cascade Impactor measurements, or Next Generation Impactor measurements. Microparticles may have a spherical shape (sometimes referred to as microspheres) and/or may be encapsulated (sometimes referred to as microencapsules). Certain microparticles may have one or more internal voids and/or cavities. Other microparticles may be free of such voids or cavities. Microparticles may be porous or non-porous porous, and optionally have smooth surfaces. Non-porous microparticles pack more nucleic acid molecules in a limited space, making delivery of the nucleic acids more efficient and effective than porous microparticles having relatively low payloads. Non-porous microparticles have minimal surface areas, effectively shielding the majority of the active agents therein from exposure to elements of degradation, making the active agents therein more storage-stable than those in porous microparticles. Microparticles may be formed from, in part or in whole, one or more non-limiting materials, such as the active agents, carriers, polymers, stabilizing agents, and/or complexing agents disclosed herein. Microparticles may be water insoluble, but for certain applications (e.g., delivery to moist or aqueous target locations) are preferably substantially water-soluble. The term "nucleic acid microparticles" refers to microparticles that are free of non-nucleic acid carrier structures such as matrices or scaffoldings or networks of non-nucleic acid materials (e.g., excipients, synthetic polymers, proteins), cores of non-nucleic acid materials (e.g., inorganic compounds, synthetic substrates), and shells or walls or envelops of non-nucleic acids materials (e.g., lipids, synthetic polymers), but rather the secondary, tertiary, and quaternary structure of which is principally attributed to the nucleic acid molecules, optionally in combination with cations.

"Spherical" refers to a geometric shape that is at least "substantially spherical." "Substantially spherical" means that the ratio of the longest length (i.e., one between two points on the perimeter and passes the geometric center of the shape) to the shortest length on any cross-section that passes through the geometric center is about 1.5 or less, preferably about 1.33 or less, more preferably 1.25 or less. Spherical does not require a line of symmetry. Further, the microparticles may have surface texturing (such as continuous or discrete lines, islands, lattice, indentations, channel openings, protuberances that are small in scale when compared to the overall size of the microparticles) and still be spherical. Surface contact there between is minimized in microparticles that are spherical, which minimizes the undesirable agglomeration of the microparticles. In comparison, microparticles that are crystals or flakes typically display significant agglomeration through ionic and/or non-ionic interactions at relatively large flat surfaces.

Surface contact is minimized in microparticles that are substantially spherical, which minimizes the undesirable agglomeration of the microparticles upon storage and/or end use. In comparison, most crystals or flakes have flat surfaces that can allow large surface contact areas where agglomeration can occur by ionic or non-ionic interactions.

In one example, the nucleic acid microparticles have a monodisperse size distribution. Microparticles having a broad size distribution where there are both relatively bigger and smaller microparticles allow for the smaller microparticles to fill in the gaps between the larger microparticles, thereby creating greater contact surfaces for agglomeration. The spherical nucleic acid microparticles disclosed herein with their monodisperse size distribution minimize opportunities for contact agglomeration. "Monodisperse size distribution" refers to a microparticle size distribution in which the ratio of the volume diameter of the $90^{th}$ percentile (i.e., the average particle size of the largest 10% of the microparticles) to the volume diameter of the $10^{th}$ percentile (i.e., the average particle size of the smallest 10% of the microparticles) is 5 or less, such as 3 or less, 2 or less, or 1.5 to 1. "Polydisperse size distribution" refers to one where the diameter ratio described above is greater than 5, such as 8 or greater, or 10 or greater.

Geometric Standard Deviation (GSD) can also be used to characterize microparticle size distribution. A GSD value of 2.5 or less, such as 1.8 or less, is an indication of monodisperse size distribution. Calculation of GSD is known and understood to one skilled in the art.

In one example of the disclosure, the nucleic acids in the microparticles are semi-crystalline or non-crystalline, such as being amorphous.

Typically, nucleic acid microparticles made by the processes in this disclosure are substantially non-porous and have a density as a result of the aggregation of the nucleic acids, which includes the compaction among the nucleic acid molecules as well as the compaction between the nucleic acids and the non-polymeric cations. In one example, the nucleic acid microparticles have a density greater than 0.5 $g/cm^3$, such as greater than 0.75 $g/cm^3$, greater than 0.85 $g/cm^3$, or greater than 1 $g/cm^3$. Ranges for the density include from 0.5 to 2 $g/cm^3$, from 0.75 to 1.75 $g/cm^3$, and from 0.85 $g/cm^3$ to 1.5 $g/cm^3$.

The nucleic acid microparticles of the present disclosure typically exhibit high content of the nucleic acids. In one example, the nucleic acid microparticles do not contain a significant quantity of bulking agents or other excipients (other than the non-polymeric cations) that are present in many other microparticles. However, bulking agents or excipients may be included in the nucleic acid microparticles disclosed herein. In another example, the nucleic acids constitute 60% to 100% by weight of the microparticles, and can be equal to or greater than the following values, or in a range between any two of such values: 65%, 70%, 75%, 80%, 85%, 90%, 95%, and 97%. In various embodiments, microparticles comprised of antisense nucleic acids and other inhibitory nucleic acids as described herein and in particular siRNA whether modified or unmodified to include a hydrophobic moiety such as cholesterol, constitute 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 93%, 94%, 95%, 96%, 97%, 98% or 99% by weight of the microparticle.

A further aspect of the present disclosure is that upon their release from the microparticles the nucleic acids incorporated therein retain most if not all (e.g., 70% to 100%) of the biochemical integrity, and the biological activity of the same nucleic acids in solubilized form.

In various aspects of the invention, microparticles are free, or essentially free of matrices and/or cores. In another aspect of the invention, microparticles are free, or essentially free of matrices, cores and/or envelopes. "Matrices," "cores" and "envelopes" as used herein refer to structural components of a microparticle that are typically inert and thus distinct from active agent(s) in the microparticle, each of which can be designed to allow for controlled release of the active agent(s). "Matrices" are in general cross-linked or otherwise porous frameworks comprised of filaments, polymers and the like into which the active agent is interspersed throughout. In one embodiment, a matrix is a combination of drug and carrier formed in essentially a single step. The carrier is often a polymeric carrier, such as PLA, PGA, and PLGA, in which the active agent is interspersed throughout the polymer carrier. The active agent may form a contiguous porous network of drug throughout the carrier through which the active agent is released. Some low molecular weight agents may actually diffuse over time through the polymeric structure. Microparticle "cores" are known in the art to include substantially dense structural components, often metallic, ceramic and/or polymeric, around which the active agent is loaded. "Cores" may be non-porous, substantially non-porous, or porous. Substantially non-porous "cores" can also have porous characteristics which allow an active agent to intercalate into the otherwise dense structure, albeit to a lesser degree than found in a "matrix." "Envelopes" are typically external microparticle structures that encase essentially all of the active agent and are often comprised of covalently-linked polymeric subunits and/or non-covalently-linked subunits, i.e., linked through ionic or hydrophobic interaction. "Envelopes" may be non-porous but degradable to an extent that the active agent can be released all at once or over time, or porous to the extent that the active agent can be released over time. Accordingly, "non-nucleic acid matrices, cores, or envelopes" as used herein refer to structural components of a microparticle which are not nucleic acid. In one type of envelope, a microcapsule is a structure containing an active agent which is then covered with a permeable, semipermaeable or impermeable coating layer. Drug release can only occur through the coating which is generally polymeric in structure.

B. Suitable Nucleic Acid Molecules

"Nucleic acid" refers to a molecule comprising nucleotides but itself is not a nucleotide monomer. The nucleic acid can be single-stranded, double-stranded, or multiple-stranded and can comprise modified or un-modified nucleotides or non-nucleotides or various mixtures and combinations thereof. The nucleic acids can be modified at the base, sugar, and/or the backbone (such as phosphate groups). Non-limiting backbone modifications include phosphodiester, phosphorothioate, phosphorodithioate, 5"-thiophosphate, and methylphosphonate. Non-limiting sugar modifications include deoxyribose, arabino, and fluoroarabino. These modifications may be present singly or in combinations of two or more of the same or different types. Those skilled in the art will recognize that the foregoing are non-limiting examples and that any combination of phosphate, sugar and base chemistry of a nucleic acid that supports the activity of the nucleic acid is within the scope of the present disclosure.

The nucleic acid microparticles of the disclosure are suitable for packaging one, two, or more nucleic acids of any lengths, sequences, primary and secondary structures (e.g., single-stranded, double-stranded, triplexes), origins (e.g., natural, synthetic, semi-synthetic, recombinant, prokaryotic, eukaryotic, exogenous, endogenous), modifications, derivations, and manipulations, as long as there is a need or desire to deliver such nucleic acids to moist or aqueous target locations such as the lung tissues. Non-limiting examples of suitable nucleic acids, beside those described in detail herein, include DNA molecules (e.g., plasmids, chromosomal DNAs), antisense DNA molecules, synthetic antisense molecules, RNA molecules (e.g., locked nucleic acids (LNA), messenger RNAs (mRNA), monocistronic mRNAs, polycistronic mRNAs, antisense mRNAs, transfer RNAs (tRNA), ribosomal RNAs (rRNA), non-coding RNAs (ncRNA), RNA genes, small RNAs (sRNA), non-messenger RNAs (nmRNA), small non-messenger RNAs (snmRNA), functional RNAs (fRNA), small nuclear RNAs (snRNA), small nucleolar RNAs (snoRNA), small Cajal body-specific RNAs (scaRNA), tmR-NAs, catalytic RNAs, ribozymes, RNase P RNAs, groups I and II introns, neurospora VS RNAs, leadzymes, hairpin ribozymes, hammerhead ribozymes, hepatitis delta virus ribozymes, tetrahymena ribozymes, double-stranded RNAs (dsRNA), primary and secondary small interfering RNAs (siRNA) with or without overhangs, pre-siRNA, silencing RNAs, microRNAs (miRNA), primary microRNAs (pri-miRNA), pre-miRNAs, endogenous siRNAs, Piwi-interacting RNAs, small activating RNAs (saRNA), guide RNAs (gRNA), efference RNAs (eRNA), promoter RNAs (pRNA), duplex antigene RNAs (agRNA), short hairpin RNAs (shRNA), hairpin RNAs,), inozymes, G-cleavers, amberzymes, zinzymes, DNAzymes, antisense nucleic acid molecules, 2,5-A chimeras, decoys (including transcriptional factor decoys), CpG oligonucleotides, aptamers, antagomers, peptide nucleic acid (PNA) molecules, other DNA and/or RNA mimics, complexes containing one, two or more of such molecules thereof (e.g., triplex oligonucleotides, RNA-induced silencing complexes (RISC)), complexes with proteins or peptides or cofactors (e.g., signal recognition particle RNA (SRP), small nuclear ribonucleoproteins (snRNP), small nucleolar ribonucleoproteins (snoRNP), miRNPs), constructs containing one, two or more of such molecules, single larger molecules containing the sequences of two or more of such molecules, modifications and derivations thereof (e.g., base modifications such as substitution, sugar modifications such as deoxyribose, arabino, and fluoroarabino, cholesterol attachment, PEGylation, photochemical modifications, backbone modifications such as PNAs, phosphorothioation, phosphoroamidation, phosphodiesterification, phosphorodithioation, 5'-thiophosphation, and methylphosphonation, 2-O-alkyl-RNAs, LNAs, peptide conjugation such as with cell-penetrating peptides, in vivo nucleic acid modifications such as photochemical deprotection and hydrolysis), as well as those explicitly or implicitly disclosed in U.S. Pat. Nos. 5,334,711, 5,627,053, 5,672,695, 5,716,824, 5,898,221, 6,001,311, 6,107,094, 6,506,559, 6,573,099, 7,056,704, and 7,078,196, U.S. Publication Nos. 20060234973, 20060240556, 20060241075, and 20060264396, U.S. Ser. Nos. 09/301,511, 60/082,404, International Patent No. EP 1,144,623, and International Publication Nos. WO 89/02439, WO 91/03162, WO 92/07065, WO 93/15187, WO 93/23569, WO 95/06731, WO 95/11910, WO 97/26270, WO 98/13526, WO 98/28317, WO 99/54459, WO 2006/105361, WO 2006/110688, WO 2006/110813, WO 2006/123800, WO 2006/126600, WO 2006/128141, and WO 2006/128739, the disclosures of which are incorporated herein in their entirety.

In one example, at least one nucleic acid (such as two or more different nucleic acids) incorporated in and releasable from the microparticles is for RNA-mediated regulation of gene expression (e.g., protein production). Non-limiting examples of RNA-mediated modulations of gene expression include RNA-mediated interference (RNAi) such as exogenously and/or endogenously induced reduction and/or silencing at transcriptional and/or post-transcriptional levels, RNA-mediated gene activation (RNAa) at transcriptional and/or post-transcriptional levels exogenously and/or endogenously. In another example, one nucleic acid released from the microparticle correlates to one specific modulation or two or more different modulations of one specific gene expression (e.g., single protein target). In another example, one nucleic acid released from the microparticle correlates to the same modulation or two or more respectively different modulations of two or more respectively different gene expressions (e.g., different protein targets). In another example, two or more different nucleic acids released from the same microparticle or two or more respectively different microparticles of the same composition correlate to the same modulation or respectively different modulations of the same gene expression (e.g., same protein target) or respectively different gene expressions (e.g., different protein targets). As such, the nucleic acid microparticles of the present disclosure provide excellent versatility and great degree of freedom in formulation.

"Suppress" or "down-regulate" means that the expression of the gene, or level of RNAs or equivalent RNAs encoding one or more protein subunits, or activity of one or more protein subunits, is reduced below that observed in the absence of the nucleic acid molecules of the disclosure. In one example, suppression with enzymatic nucleic acid molecule preferably is below that level observed in the presence of an enzymatically inactive or attenuated molecule that is able to bind to the same site on the target RNA, but is unable to cleave that RNA. In another example, suppression with antisense oligonucleotides is preferably below that level observed in the presence of, for example, an oligonucleotide with scrambled sequence or with mismatches. In another example, suppression with the nucleic acid molecule of the instant disclosure is greater in the presence of the nucleic acid molecule than in its absence.

"Up-regulate" means that the expression of the gene, or level of RNAs or equivalent RNAs encoding one or more protein subunits, or activity of one or more protein subunits, is greater than that observed in the absence of the nucleic acid molecules of the disclosure. For example, the expression of a gene, can be increased in order to treat, prevent, ameliorate, or modulate a pathological condition caused or exacerbated by an absence or low level of gene expression.

"Modulate" means that the expression of the gene, or level of RNAs or equivalent RNAs encoding one or more protein subunits, or activity of one or more protein subunit(s) is up-regulated or down-regulated, such that the expression, level, or activity is greater than or less than that observed in the absence of the nucleic acid molecules of the disclosure.

"Enzymatic nucleic acid molecule" refers to a nucleic acid molecule that has complementarity in a substrate-binding region to a specified gene target, and also has an enzymatic activity that is active to specifically cleave target RNA. The enzymatic nucleic acid molecule typically is able to intermolecularly cleave RNA and thereby inactivate a target RNA molecule. These complementary regions allow sufficient hybridization of the enzymatic nucleic acid molecule to the target RNA and thus permit cleavage. One hundred percent complementarity is preferred, but complementarity as low as 50% to 75% can also be useful in this disclosure. The term enzymatic nucleic acid includes, without limitation, ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme and DNA enzyme.

Several varieties of enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target-binding portion of a enzymatic nucleic acid that is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets. Thus, a single enzymatic molecule is able to cleave many molecules of target RNA. In addition, the enzymatic nucleic acid is a highly specific inhibitor of gene expression, with the specificity of inhibition depending not only on the base-pairing mechanism of binding to the target RNA, but also on the mechanism of target RNA cleavage. Single mismatches, or base-substitutions, near the site of cleavage can completely eliminate catalytic activity of a enzymatic nucleic acid.

"Enzymatic portion" or "catalytic domain" of an enzymatic nucleic acid molecule refers to the portion/region of the enzymatic nucleic acid molecule essential for cleavage of a nucleic acid substrate.

"Substrate-binding arm" or "substrate-binding domain" refers to the portion/region of a enzymatic nucleic acid that is able to interact, for example via complementarity (i.e., ability to base-pair), with a portion of its substrate. Preferably, such complementarity is 100%, but can be less if desired (e.g., as few as 10 bases out of 14 can be base-paired). These arms contain sequences within an enzymatic nucleic acid that are intended to bring enzymatic nucleic acid and target RNA together through complementary base-pairing interactions. The enzymatic nucleic acid of the disclosure can have binding arms that are contiguous or non-contiguous and can be of varying lengths. The length of the binding arm(s) are preferably greater than or equal to three nucleotides and of sufficient length to stably interact with the target RNA; preferably 12-100 nucleotides; more preferably 14-24 nucleotides long. If two binding arms are chosen, the design is such that the length of the binding arms are symmetrical (i.e., each of the binding arms is of the same length; e.g., five and five nucleotides, or six and six nucleotides, or seven and seven nucleotides long) or asymmetrical (i.e., the binding arms are of different length; e.g., six and three nucleotides; three and six nucleotides long; four and five nucleotides long; four and six nucleotides long; four and seven nucleotides long; and the like).

"Inozyme" or "NCH" motif or configuration refers to an enzymatic nucleic acid molecule having endonuclease activity to cleave RNA substrates having a cleavage triplet NCH/, where N is a nucleotide, C is cytidine and H is adenosine, uridine or cytidine, and "/" represents the cleavage site. H is used interchangeably with X. Inozymes can also possess endonuclease activity to cleave RNA substrates having a cleavage triplet NCN/, where N is a nucleotide, C is cytidine, and "/" represents the cleavage site.

"G-cleaver" motif or configuration refers to an enzymatic nucleic acid molecule having endonuclease activity to cleave RNA substrates having a cleavage triplet NYN/, where N is a nucleotide, Y is uridine or cytidine and "/" represents the cleavage site. G-cleavers can be chemically modified.

"Amberzyme" motif or configuration refers to an enzymatic nucleic acid molecule having endonuclease activity to cleave RNA substrates having a cleavage triplet NG/N, where N is a nucleotide, G is guanosine, and "/" represents the cleavage site. Amberzymes can be chemically modified to increase nuclease stability through substitutions. In addition, differing nucleoside and/or non-nucleoside linkers can be used to substitute the 5'-gaaa-3' loops. Amberzymes represent a non-limiting example of an enzymatic nucleic acid molecule that does not require a ribonucleotide (2'-OH) group within its own nucleic acid sequence for activity.

"Zinzyme" motif or configuration refers to an enzymatic nucleic acid molecule having endonuclease activity to cleave RNA substrates having a cleavage triplet including but not limited to YG/Y, where Y is uridine or cytidine, and G is guanosine and/represents the cleavage site. Zinzymes can be chemically modified to increase nuclease stability through substitutions, including substituting 2'-O-methyl guanosine nucleotides for guanosine nucleotides. In addition, differing nucleotide and/or non-nucleotide linkers can be used to substitute the 5'-gaaa-2' loop. Zinzymes represent a non-limiting example of an enzymatic nucleic acid molecule that does not require a ribonucleotide (2'-OH) group within its own nucleic acid sequence for activity.

"DNAzyme" motif or configuration refers to an enzymatic nucleic acid molecule that does not require the presence of a 2'-OH group within its own nucleic acid sequence for activity. In particular examples the enzymatic nucleic acid molecule can have an attached linker(s) or other attached or associated groups, moieties, or chains containing one or more nucleotides with 2'-OH groups. DNAzymes can be synthesized chemically or expressed endogenously in vivo, by means of a single stranded DNA vector or equivalent thereof.

"Sufficient length" refers to an oligonucleotide of greater than or equal to 3 nucleotides that is of a length great enough to provide the intended function under the expected condition. For example, for binding arms of enzymatic nucleic acid "sufficient length" means that the binding arm sequence is long enough to provide stable binding to a target site under the expected binding conditions. Preferably, the binding arms are not so long as to prevent useful turnover of the nucleic acid molecule.

"Stably interact" refers to interaction of the oligonucleotides with target nucleic acid (e.g., by forming hydrogen bonds with complementary nucleotides in the target under physiological conditions) that is sufficient to the intended purpose (e.g., cleavage of target RNA by an enzyme).

"Equivalent" or "related" RNA include those naturally occurring RNA molecules having homology (partial or complete) to target proteins or encoding for proteins with similar function in various organisms, including human, rodent, primate, rabbit, pig, protozoans, fungi, plants, and other microorganisms and parasites. The equivalent RNA sequence also includes in addition to the coding region, regions such as 5'-untranslated region, 3'-untranslated region, introns, intron-exon junction and the like.

"Homology" means the nucleotide sequence of two or more nucleic acid molecules is partially or completely identical.

"Antisense nucleic acid" refers to a non-enzymatic nucleic acid molecule that binds to target RNA by means of RNA-RNA or RNA-DNA or RNA-PNA (protein nucleic acid) interactions and alters the activity of the target RNA. Typically, antisense molecules are complementary to a target sequence along a single contiguous sequence of the antisense molecule. However, in certain examples, an antisense molecule can bind such that the substrate molecule forms a loop, and/or an antisense molecule can bind such that the antisense molecule forms a loop. Thus, the antisense molecule can be complementary to two (or even more) non-contiguous substrate sequences, or two (or even more) non-contiguous sequence portions of an antisense molecule can be complementary to a target sequence or both. In addition, antisense DNA can be used to target RNA by means of DNA-RNA interactions, thereby activating RNase H, which digests the target RNA in the duplex. The antisense oligonucleotides can comprise one or more RNAse H activating regions that is capable of activating RNAse H cleavage of a target RNA. Antisense DNA can be synthesized chemically or expressed via the use of a single stranded DNA expression vector or equivalents thereof.

"RNase H activating region" refers to a region (such as those of 4-25 nucleotides or longer, e.g., 5-11 nucleotides in length) of a nucleic acid molecule capable of binding to a target RNA to form a non-covalent complex that is recognized by cellular RNase H enzyme. The RNase H enzyme binds to the nucleic acid molecule-target RNA complex and cleaves the target RNA sequence. The RNase H activating region comprises, for example, phosphodiester, phosphorothioate (such as those with at least four of the nucleotides being phosphorothioted, e.g., 4-11 of the nucleotides being phosphorothioted); phosphorodithioate, 5'-thiophosphate, or methylphosphonate backbone chemistry or a combination thereof. In addition, the RNase H activating region can also comprise a variety of sugar chemistries. For example, the RNase H activating region can comprise deoxyribose, arabino, fluoroarabino or a combination thereof, nucleotide sugar chemistry.

"2-5A chimera" is meant an oligonucleotide, for example an antisense nucleic acid molecule or enzymatic nucleic acid molecule, containing a 5'-phosphorylated 2'-5'-linked adenylate residue. These chimeras bind to target RNA in a sequence-specific manner and activate a cellular 2-5A-dependent ribonuclease that, in turn, cleaves the target RNA.

"Triplex forming oligonucleotides" or "triplex oligonucleotide" refers to an oligonucleotide that can bind to a double-stranded DNA in a sequence-specific manner to form a triple-strand helix. Formation of such triple helix structure has been shown to inhibit transcription of the targeted gene.

"Double-stranded RNA" or "dsRNA" refers to a double-stranded RNA molecule capable of RNA interference "RNAi", and include, without being limited thereto, short interfering RNA (siRNA). The dsRNA typically matches a predetermined gene sequence that is capable of activating cellular enzymes that degrade the corresponding messenger RNA transcripts of the gene. These dsRNAs can be used to inhibit gene expression.

"Gene" refers to a nucleic acid that encodes an RNA, for example, nucleic acid sequences including but not limited to structural genes encoding a polypeptide.

"Complementarity" refers to the ability of a nucleic acid to form hydrogen bond(s) with another RNA sequence by either traditional Watson-Crick or other non-traditional types. In reference to the nucleic molecules of the present disclosure, the binding free energy for a nucleic acid molecule with its target or complementary sequence is sufficient to allow the relevant function of the nucleic acid to proceed, e.g., enzymatic nucleic acid cleavage, antisense or triple helix inhibition. Determination of binding free energies for nucleic acid molecules is well known in the art. A percent complementarity indicates the percentage of contiguous residues in a nucleic acid molecule that can form hydrogen bonds (e.g., Watson-Crick base-pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence.

"RNA" refers to a molecule comprising at least one ribonucleotide residue, but itself is not a ribonucleotide. "Ribonucleotide" or "2'-OH" refers to a nucleotide with a hydroxyl group at the 2' position of a β-D-ribo-furanose moiety.

"MicroRNA" or "miRNA" refers to a small double stranded RNA that regulates the expression of target messenger RNAs either by mRNA cleavage, translational repression/inhibition or heterochromatic silencing. In one example, the microRNA has partial complementarity (i.e., less than 100% complementarity) between the sense strand or sense region and the antisense strand or antisense region of the miRNA molecule or between the antisense strand or antisense region of the miRNA and a corresponding target nucleic acid molecule. For example, partial complementarity can include various mismatches or non-base paired nucleotides (e.g., 1, 2, 3, 4, 5 or more mismatches or non-based paired nucleotides, such as nucleotide bulges) within the double stranded nucleic acid molecule, structure which can result in bulges, loops, or overhangs that result between the sense strand or sense region and the antisense strand or antisense region of the miRNA or between the antisense strand or antisense region of the miRNA and a corresponding target nucleic acid molecule.

"Decoy" refers to a nucleic acid molecule, for example RNA or DNA, or aptamer that is designed to preferentially bind to a predetermined ligand. Such binding can result in the inhibition or activation of a target molecule. The decoy or aptamer can compete with a naturally occurring binding target for the binding of a specific ligand.

"Aptamer" or "nucleic acid aptamer" refers to a nucleic acid molecule that binds specifically to a target molecule wherein the nucleic acid molecule has sequence that is distinct from sequence recognized by the target molecule in its natural setting. Alternately, an aptamer can be a nucleic acid molecule that binds to a target molecule where the target molecule does not naturally bind to a nucleic acid. The target molecule can be any natural or a synthetic molecule, including but not limited to a resin, metabolites, nucleosides, nucleotides, drugs, toxins, transition state analogs, peptides, lipids, proteins, amino acids, nucleic acid molecules, hormones, carbohydrates, receptors, cells, viruses, bacteria and others. For example, the aptamer can be used to bind to a ligand-binding domain of a protein, thereby preventing interaction of the naturally occurring ligand with the protein. Similarly, the nucleic acid molecules of the instant disclosure can bind and thus block activity of proteins.

The enzymatic nucleic acid molecule, antisense nucleic acid molecule, double-stranded RNA molecule, or other nucleic acid molecules of the disclosure that modulate (e.g., up-regulate or down-regulate) gene expression represent a therapeutic approach to treat a variety of diseases and conditions, including but not limited to those that relate to the respiratory system, such as obstructive lung diseases (e.g., emphysema, bronchitis, asthma, chronic obstructive pulmonary disease, bronchiectasis, byssinosis, bronchiolitis, asbestosis, restrictive lung diseases such as fibrosis, cystic fibrosis, sarcoidosis, alveolar damage, pleural effusion, hypersensitivity pneumonitis, pleurisy, lung cancer, infectious lung diseases such as influenza, upper respiratory tract infections, lower respiratory tract infections or pneumonias, tuberculosis, vascular lung diseases such as pulmonary edema, pulmonary embolism, pulmonary hypertension, and respiratory tumors), those that are inflammatory-related such as rheumatoid arthritis, restenosis, asthma, Crohn's disease, incontinentia pigmenti, diabetes, obesity, autoimmune disease, lupus, multiple sclerosis, transplant/graft rejection, gene therapy applications, ischemia/reperfusion injury (CNS and myocardial), glomerulonephritis, sepsis, allergic airway inflammation, inflammatory bowel disease, and infection, as well as a variety of cancers, including but not limited to breast, lung, prostate, colorectal, brain, esophageal, bladder, pancreatic, cervical, head and neck, and ovarian cancer, melanoma, lymphoma, glioma, and multidrug resistant cancers.

In one example, a nucleic acid molecule used in the microparticle compositions of the disclosure contains one, two, or more nucleotide sequences each 3-100 nucleotides in length, such as 5-100, or 10-100 nucleotides in length. Exemplary enzymatic nucleic acid molecules of the disclosure are 12-50 nucleotides in length, such as 15-45, 20-40, or 25-40 nucleotides in length, e.g., 34, 36, or 38 nucleotides in length. Exemplary DNAzymes of the disclosure are 12-40 nucleotides in length, such as 15-40, 20-35, or 25-35 nucleotides in length, e.g., 29, 30, 31, or 32 nucleotides in length. Exemplary antisense molecules of the disclosure are 12-100 nucleotides in length, such as 15-75, 20-50, or 20-35 nucleotides in length, e.g., 21, 25, 26, 27, or 28 nucleotides in length. Exemplary triplex forming oligonucleotide molecules of the disclosure are 8-40 nucleotides in length, such as 10-30 or 12-25 nucleotides in length, e.g., 18, 19, 20, or 21 nucleotides in length. Those skilled in the art will recognize that all that is required is that the nucleic acid molecule be of sufficient length and suitable conformation for the nucleic acid molecule to interact with its target and/or catalyze a reaction contemplated herein. The length of the nucleic acid molecules of the instant disclosure are not limiting within the general limits stated.

The disclosure provides a class of nucleic acid-based gene modulating agents that exhibit a high degree of specificity for the RNA of a desired target such that, for example, specific treatment of a disease or condition can be provided with either one or several nucleic acid molecules of the disclosure. Such nucleic acid molecules can be delivered exogenously in the microparticles disclosed herein to specific tissues or cells as required. Alternatively, the nucleic acid molecules (e.g., ribozymes and antisense) can be expressed from DNA and/or RNA vectors that are delivered in the microparticles disclosed herein to specific tissues or cells.

"Cell" is used in its usual biological sense, and does not refer to an entire multicellular organism. The cell can, for example, be in vitro, e.g., in cell culture, or present in a multicellular organism, including, e.g., birds, plants and mammals such as humans, cows, sheep, apes, monkeys, swine, dogs, and cats. The cell can be prokaryotic (e.g., bacterial cell) or eukaryotic (e.g., mammalian or plant cell).

"Highly conserved sequence region" refers to a nucleotide sequence of one or more regions in a target gene that do not vary significantly from one generation to the other or from one biological system to the other.

The nucleic acids used in the microparticle compositions of the disclosure may include nucleotide linkers linking multiple nucleic acids, the linkers can be 2 nucleotides in length or longer, such as 3, 4, 5, 6, 7, 8, 9, 10, 15, 20, 26, 30, or longer, or in a range between any two of such values. The nucleotides can be internally base-paired to form a stem of 2 or more base pairs. Nucleotide linker can be a nucleic acid aptamer, such as an ATP aptamer.

In yet another example, alternatively or in addition, sequence X can be a non-nucleotide linker. Non-nucleotides as can include abasic nucleotide, polyether, polyamine, polyamide, peptide, carbohydrate, lipid, or polyhydrocarbon compounds. A "non-nucleotide" further means any group or compound which can be incorporated into a nucleic acid chain in the place of one or more nucleotide units, including either sugar and/or phosphate substitutions, and allows the remaining bases to exhibit their activity. The group or compound can be abasic in that it does not contain a commonly recognized nucleotide base, such as adenosine, guanine, cytosine, uracil or thymine.

In another example of the disclosure, nucleic acid molecules (e.g., enzymatic nucleic acid molecules or antisense molecules) that interact with target RNA molecules are expressed from transcription units inserted into DNA or RNA vectors. The recombinant vectors include DNA plasmids or viral vectors, but are not limited thereto. Enzymatic nucleic acid molecule or antisense expressing viral vectors can be constructed based on, but not limited to, adeno-associated virus, retrovirus, adenovirus, or alphavirus. The recombinant vectors capable of expressing the enzymatic nucleic acid molecules or antisense can be delivered to moist or aqueous target locations through the microparticles as described herein, and persist in target cells. Alternatively, viral vectors can be used that provide for transient expression of nucleic acid molecules. Microparticles of such vectors can be repeatedly administered as necessary. The administration can be local or systemic, such as by pulmonary administration, by intravenous or intramuscular administration, by administration to target cells explanted from the patient or subject followed by reintroduction into the patient or subject, or by any other means that would allow for introduction into the desired target cell. Antisense DNA can be expressed via the use of a single stranded DNA intracellular expression vector.

"Vectors" refers to any nucleic acid- and/or viral-based technique used to incorporate a desired nucleic acid in a larger molecule or construct.

"Subject" or "patient" refers to animals, including vertebrates like mammals, preferably humans.

"Region of a subject" refers to a localized internal or external area or portion of the subject (e.g., an organ), or a collection of areas or portions throughout the entire subject (e.g., lymphocytes). Non-limiting examples of such regions include pulmonary region (e.g., lung, alveoli, gastrointestinal region (e.g., regions defined by esophagus, stomach, small large intestines, and rectum), cardiovascular region (e.g., myocardial tissue), renal region (e.g., the region defined by the kidney, the abdominal aorta, and vasculature leading directly to and from the kidney), vasculature (i.e., blood vessels, e.g., arteries, veins, capillaries, and the like), circulatory system, healthy or diseased tissues, benign or malignant (e.g., tumorous or cancerous) tissues, lymphocytes, receptors, organs and the like, as well as regions to be imaged with diagnostic imaging, regions to be administered and/or treated with an active agent, regions to be targeted for the delivery of an active agent, and regions of elevated temperature.

"Tissue" refers generally to an individual cell or a plurality or aggregate of cells specialized and capable of performing one or more particular functions. Non-limiting tissue examples include membranous tissues, (e.g., endothelium, epithelium), blood, laminae, connective tissue (e.g., interstitial tissue), organs (e.g., myocardial tissue, myocardial cells, cardiomyocites), abnormal cell(s) (e.g., tumors).

"Enhanced activity" refers to activity measured in cells and/or in vivo where the activity is a reflection of both the activity and the stability of the nucleic acid molecules of the disclosure. In this disclosure, the product of these properties can be increased in vivo compared to non-microparticle based formulations. In some cases, the activity or stability of the nucleic acid molecule can be decreased (e.g., less than tenfold), but the overall activity of the released nucleic acid molecule is enhanced, in vivo.

The nucleic acid molecules of the instant disclosure, individually, or in combination or in conjunction with other drugs, can be used to treat diseases or conditions discussed herein.

In a further example, the described nucleic acid microparticles can be used in combination with other known treatments to treat conditions or diseases discussed herein. For example, the described microparticles can be used in combination with one or more known therapeutic agents to treat (e.g., down-regulate or inhibit the expression of genes capable of progression or maintenance of) breast, lung, prostate, colorectal, brain, esophageal, bladder, pancreatic, cervical, head and neck, and ovarian cancer, melanoma, lymphoma, glioma, multidrug resistant cancers, rheumatoid arthritis, restenosis, asthma, Crohn's disease, diabetes, incontinentia pigmenti, obesity, autoimmune disease, lupus, multiple sclerosis, transplant/graft rejection, gene therapy applications, ischemia/reperfusion injury (CNS and myocardial), glomerulonephritis, sepsis, allergic airway inflammation, inflammatory bowel disease, infection, and any other cancerous disease or inflammatory disease or condition.

Synthesis of nucleic acids greater than 100 nucleotides in length can be difficult using automated methods, and the therapeutic cost of such molecules can be prohibitive. In this disclosure, small nucleic acid motifs ("small refers to nucleic acid motifs less than about 100 nucleotides in length, preferably less than about 80 nucleotides in length, and more preferably less than about 50 nucleotides in length; e.g., antisense oligonucleotides, hammerhead or the NCH ribozymes) are preferably used for exogenous delivery. The simple structure of these molecules increases the ability of the nucleic acid to invade targeted regions of RNA structure. Exemplary molecules of the instant disclosure are chemically synthesized, and others can similarly be synthesized.

Oligonucleotides (e.g.; antisense, GeneBlocs) are synthesized using protocols known in the art as described, for example, in International Publication No. WO 99/54459, U.S. Pat. No. 6,001,311, as well as other references incorporated herein by reference.

Chemically synthesizing nucleic acid molecules with modifications (base, sugar and/or phosphate) that prevent their degradation by serum ribonucleases can increase their potency. Modifications which enhance their efficacy in cells, and removal of bases from nucleic acid molecules to shorten oligonucleotide synthesis times and reduce chemical requirements are, in certain examples but not in others, desired.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-fluoro, 2'-O-methyl, 2'-H, nucleotide base modifications. Sugar modifications of nucleic acid molecules have been extensively described in the art. Certain references incorporated herein describe general methods and strategies to determine the location of incorporation of sugar, base and/or phosphate modifications and the like into nucleic acid molecules without inhibiting their activities. In view of such teachings, similar modifications can be used as described herein to modify the nucleic acid molecules of the instant disclosure.

While chemical modification of oligonucleotide internucleotide linkages with phosphorothioate, phosphorothioate, and/or 5'-methylphosphonate linkages improves stability, too many of these modifications can cause some toxicity. Therefore when designing nucleic acid molecules the amount of these internucleotide linkages should be minimized. The reduction in the concentration of these linkages should lower toxicity resulting in increased efficacy and higher specificity of these molecules.

Nucleic acid molecules having chemical modifications that maintain or enhance activity are provided. Such nucleic acid is also generally more resistant to nucleases than unmodified nucleic acid. Thus, in a cell and/or in vivo the activity would not be significantly lowered. Therapeutic nucleic acid molecules delivered exogenously are optimally stable within cells until translation of the target RNA has been inhibited long enough to reduce the levels of the undesirable protein. This period of time varies between hours to days depending upon the disease state. Nucleic acid molecules are preferably resistant to nucleases in order to function as effective intracellular therapeutic agents. Improvements in the chemical synthesis of RNA and DNA have expanded the ability to modify nucleic acid molecules by introducing nucleotide modifications to enhance their nuclease stability as described herein.

Use of the nucleic acid-based molecules can lead to better treatment of the disease progression by affording the possibility of combination therapies (e.g., multiple antisense or enzymatic nucleic acid molecules targeted to different genes, nucleic acid molecules coupled with known small molecule inhibitors, or intermittent treatment with combinations of molecules (including different motifs) and/or other chemical or biological molecules). The treatment of subjects with nucleic acid molecules can also include combinations of different types of nucleic acid molecules.

In another aspect the nucleic acid molecules comprise a 5' and/or a 3'-cap structure. "Cap structure" refers to chemical modifications, which have been incorporated at either terminus of the oligonucleotide. These terminal modifications protect the nucleic acid molecule from exonuclease degradation, and can help in delivery and/or localization within a cell. The cap can be present at the 5'-terminus (5'-cap) or at the 3'-terminus (3'-cap) or can be present on both terminus. In non-limiting examples, the 5'-cap includes inverted abasic residue (moiety), 4',5'-methylene nucleotide; 1-(beta-D-erythrofuranosyl)nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

In another example the 3'-cap includes, for example 4',5'-methylene nucleotide; 1-(beta-D-erythrofuranosyl)nucleotide; 4'-thio nucleotide, carbocyclic nucleotide; 5'-aminoalkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties.

"Nucleotide" refers to a heterocyclic nitrogenous base in N-glycosidic linkage with a phosphorylated sugar. Nucleotides are recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other. Some of the non-limiting examples of chemically modified and other natural nucleic acid bases that can be introduced into nucleic acids include, for example, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetyltidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid, 2-thiocytidine, threonine derivatives and others. "Modified bases" refer to nucleotide bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

"Nucleoside" refers to a heterocyclic nitrogenous base in N-glycosidic linkage with a sugar. Nucleosides are recognized in the art to include natural bases (standard), and modified bases well known in the art. Such bases are generally located at the 1' position of a nucleoside sugar moiety. Nucleosides generally comprise a base and sugar group. The nucleosides can be unmodified or modified at the sugar, and/or base moiety, (also referred to interchangeably as nucleoside analogs, modified nucleosides, non-natural nucleosides, non-standard nucleosides and other).

In one example, the disclosure features modified enzymatic nucleic acid molecules with phosphate backbone modifications comprising one or more phosphorothioate, phosphorodithioate, methylphosphonate, morpholino, amidate carbamate, carboxymethyl, acetamidate, polyamide, sulfonate, sulfonamide, sulfamate, formacetal, thioformacetal, and/or alkylsilyl, substitutions.

Various modifications to nucleic acid (e.g., antisense and ribozyme) structure can be made to enhance the utility of these molecules. For example, such modifications can enhance shelf-life, half-life in vitro, stability, and ease of introduction of such oligonucleotides to the target site, including e.g., enhancing penetration of cellular membranes and conferring the ability to recognize and bind to targeted cells.

Use of these molecules can lead to better treatment of the disease progression by affording the possibility of combination therapies (e.g., multiple enzymatic nucleic acid molecules targeted to different genes, enzymatic nucleic acid molecules coupled with known small molecule inhibitors, or intermittent treatment with combinations of enzymatic nucleic acid molecules (including different enzymatic nucleic acid molecule motifs) and/or other chemical or biological molecules). The treatment of subjects with nucleic acid molecules can also include combinations of different types of nucleic acid molecules. Therapies can be devised which include a mixture of enzymatic nucleic acid molecules (including different enzymatic nucleic acid molecule motifs), antisense and/or 25A chimera molecules to one or more targets to alleviate symptoms of a disease.

As mentioned above, one embodiment of the invention is a microsphere comprising a modified nucleic acid, wherein the nucleic acid is conjugated to a lipophilic (or hydrophobic) moiety. Conjugation of siRNA to lipophilic moieties is known in the art (See, e.g., Us Patent Application Publication No. 20070298445, US Patent Application Publication No. 20070082845, U.S. Pat. Nos. 5,138,045, 5,218,105 and 5,459,255, and US Patent Application Publication No, 20070072904) and binding properties of the thus conjugated siRNA has been characterized. See for example, Wolfram, et al., Nature Biotechnology (2007) 25:1149-1157 (published online Sep. 16, 2007) which describes siRNA conjugation to cholesterol, stearoyl, docosanyl, lithocholic-oleyl, lithocholic acid or lauric acid, some of which associate with high density lipoprotein particles, as well as siRNA conjugated to short- and medium-chain fatty acids, such as lauroyl, myristoyl and palmitoyl siRNA, which do not bind to lipoproteins but associate with either serum albumin or remained in an unbound form. Wolfram et al., also disclose that cholesterol is not unique in its ability to bind siRNAs to lipoprotein particles: other highly lipophilic conjugates, such as long-chain fatty acids and bile acids, are also effective in binding to lipoproteins and mediating siRNA uptake into cells. A critical factor determining the affinity of fatty acid-conjugated siRNAs to lipoprotein particles is the length of the alkyl chain, a major determinant of lipophilicity. In the series of fatty acid siRNA conjugates, docosanyl (C22) and stearoyl (C18) conjugates show stronger binding to HDL and efficiently silence gene expression in vivo, whereas lauroyl (C12) and myristoyl (C14) conjugates and other medium and small-chain fatty-acids exhibit weak interactions with lipoprotein particles. In other aspects, Skobridis et al., ARKIVOC (2005) (vi) 459-469 describes lipophilic dendrimeric building blocks and incorporated them into oligonucleotides.

US Patent Application Nos. 20060008822 and 20070275465 disclose that conjugating a ligand to a dsRNA can enhance its cellular absorption. For example, cholesterol has been conjugated to various antisense oligonucleotides resulting in compounds that are substantially more active compared to their non-conjugated analogs. See M. Manoharan Antisense & Nucleic Acid Drug Development 2002, 12, 103. Other lipophilic compounds that have been conjugated to oligonucleotides include 1-pyrene butyric acid, 1,3-bis-O-hexadecyl)glycerol, and menthol. The applications further disclose that other lipophilic moieties such as polyethyleneglycolized fatty glycerides, polyethylene glycols, saturated and monounsaturated polyethyleneglycolyzed fatty acid glycerides, such as those obtained from fully or partially hydrogenated various vegetable oils. Such oils may advantageously consist of tri-. di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Still other useful moieties are described to include partially esterified sorbitan and/or sorbitol, with saturated or mono-unsaturated fatty acids (SPAN-series) or corresponding ethoxylated analogs (TWEEN-series), as well as commercially available moieties such as Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

US Patent Application Nos. 20050186591, 20050288244, 20070213292, 20070275914, 20060035254 and 20070161595 describe lipophilic moieties to include cholesterol, lipid, oleyl, retinyl, cholesterol residues, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine.

US Patent Application Publication No, 20060008822 discloses that cholesterol has been conjugated to various antisense oligonucleotides resulting in compounds that are substantially more active compared to their non-conjugated analogs. See M. Manoharan Antisense & Nucleic Acid Drug Development 2002, 12, 103. Other lipophilic compounds that have been conjugated to oligonucleotides include 1-pyrene butyric acid, 1,3-bis-O-(hexadecyl)glycerol, and menthol.

US Patent Application Publication Nos. 20080039415, 20070004667, and 20080039414 disclose additional lipophilic groups to include saturated or unsaturated linear, branched, or cyclic alkyl group, cholesterol, or a derivative thereof. Still other lipophilic moieties include fatty acids and their derivatives, including straight chain, branched chain, saturated and unsaturated fatty acids, carotenoids, terpenes, bile acids, and steroids, including cholesterol, vitamin E, vitamin K, vitamin A, folic acid, a cationic dye, such as Cy3, and derivatives or analogs thereof.

US Patent Application Publication No. 20070026079 discloses lipophilic substances that can enhance delivery of the compound across the nasal mucus and include fatty acids (e.g., palmitic acid), gangliosides (e.g., GM-I), phospholipids (e.g., phosphatidylserine), and emulsifiers (e.g., polysorbate 80), bile salts such as sodium deoxycholate, and detergent-like substances including, for example, polysorbate 80 such as Tween™, octoxynol such as Triton™ X-100, and sodium tauro-24,25-dihydrofusidate (STDHF).

Various other aspects of the invention and methods for producing these aspects are described in US Patent Application Publication Nos.: 20040198640, 20070173476, 20050107325, 20050119214, 20040110296, 20040249178, 20050058982, 20040171033, and 20050119470, The disclosures of each patent and application publication discussed above is incorporated by reference with respect to the lipophilic moieties described therein and attachment of lipophilic moieties to nucleic acids.

C. Methods of Making the Microparticles

In one example, the microparticles are formed by mixing an aqueous non-polymeric cation solution and an aqueous nucleic acid solution and reducing the solubility of the nucleic acids to form the microparticles. In another example, in addition to the nucleic acid and non-polymeric cation, the reaction solution further contains one or more aqueous or aqueous-miscible non-ionic polymers. In general, such processes involve solubilizing the materials (e.g., nucleic acids, non-polymeric cations, and non-ionic polymers) through, for example, heating the different solutions to a sufficient temperature (e.g., in the range of from 37° C. to 95° C.) for a sufficient time period (e.g., 1 minute to 24 hours). As used herein, an "aqueous solution", refers to solutions of water or buffer alone as the solvent, or water or buffer mixed with one or more water-miscible solvents, such as ethanol, DMSO, acetone, N-methyl pyrrolidone, and 2-pyrrolidone; however, the preferred aqueous solutions do not contain detectable organic solvents.

The present disclosure is related to methods of production and methods of use and compositions of microparticles of nucleic acids such as, without limitation, antisense oligonucleotides or siRNA molecules. In accordance with the methods of production, the nucleic acid (e.g., antisense oligonucleotides, siRNA molecules, or combinations of two or more thereof) is solubilized in a single-phase reaction solution containing one or more solubilized non-polymeric cations and one or more solubilized non-ionic polymers. The solvent is aqueous or aqueous-miscible (e.g., water, buffer). The reaction solution is then subjected to cooling to below the phase transition temperature of the active agent (without freezing), whereby the nucleic acid molecules and the non-polymeric cations together go through a liquid-solid phase separation to form spherical microparticles constituting a discontinuous phase suspended in the continuous phase containing the solubilized non-ionic polymers and other components not incorporated into the nucleic acid microparticles.

The Continuous Phase:

The method of the present disclosure of preparing microparticles of nucleic acids begins with providing a reaction mixture in which the one or more nucleic acids, the one or more non-polymeric cations, and the one or more non-ionic polymers are all substantially solubilized in a single continuous phase. The single continuous phase of the reaction mixture is an aqueous-based solution comprising an aqueous medium and, optionally, an aqueous-miscible organic solvent or a mixture of aqueous-miscible organic solvents, or combinations thereof. The aqueous medium can be water, salt solutions (e.g., normal saline), buffered solutions, buffered saline, and the like.

Suitable aqueous-miscible organic solvents include, but are not limited to, N-methyl-2-pyrrolidinone (N-methyl-2-pyrrolidone), 2-pyrrolidinone (2-pyrrolidone), 1,3-dimethyl-2-imidazolidinone (DMI), dimethylsulfoxide, dimethylacetamide, acetic acid, lactic acid, acetone, methyl ethyl ketone, acetonitrile, methanol, ethanol, isopropanol, 3-pentanol, n-propanol, benzyl alcohol, glycerol, tetrahydrofuran (THF), polyethylene glycol (PEG), PEG-4, PEG-8, PEG-9, PEG-12, PEG-14, PEG-16, PEG-120, PEG-75, PEG-150, polyethylene glycol esters, PEG-4 dilaurate, PEG-20 dilaurate, PEG-6 isostearate, PEG-8 palmitostearate, PEG-150 palmitostearate, polyethylene glycol sorbitans, PEG-20 sorbitan isostearate, polyethylene glycol monoalkyl ethers, PEG-3 dimethyl ether, PEG-4 dimethyl ether, polypropylene glycol (PPG), polypropylene alginate, PPG-10 butanediol, PPG-10 methyl glucose ether, PPG-20 methyl glucose ether, PPG-15 stearyl ether, propylene glycol dicaprylate/dicaprate, propylene glycol laurate, and glycofurol (tetrahydrofurfuryl alcohol polyethylene glycol ether), alkanes including propane, butane, pentane, hexane, heptane, octane, nonane, decane, or a combination thereof.

The single continuous phase (i.e., the reaction solution) can be prepared by dissolving the nucleic acids, salts or hydroxides of the non-polymeric cations, and the non-ionic polymers in any appropriate order (e.g., together at once or in sequence of each other) in a single aqueous medium, or by providing separate solutions of one or two of these components in the same or different aqueous media and then combine these separate solutions in any appropriate order (e.g., together at once or in sequence of each other). Physical means to facilitate solvation of the various components, such as increasing temperature (e.g., heating), decreasing pressure, and/or adjusting pH, are optionally applied in the formation of the reaction solution and/or the separate solutions, provided that the components are not adversely affected (e.g., reduction in nucleic acid activity, degradation or decomposition or crosslinking of the molecules). In one example, a nucleic acid solution is first combined with a non-ionic polymer solution, the mixture of which is then combined with a non-polymeric cation solution. In another example, a non-polymeric cation solution is first combined with a non-ionic polymer solution, the mixture of which is then combined with a nucleic acid solution. In another example, a nucleic acid solution is first combined with a non-polymeric cation solution, the mixture of which is then combined with a non-ionic polymer solution. In another example, concentrated stock solutions of the various components are separately prepared, and aliquots of the stock solutions are used together with appropriate diluents to provide the reaction solution. The reaction mixture resulted from the combination of the separate solutions is, visibly, a single-phase solution in which no phase separation (e.g., haziness, milky color, clouding, precipitation, crystallization, emulsion, oil-water separation) is visible, or a dispersion with some phase separation. In another example, a visibly clear reaction solution is formed upon combining the separate solution under normal operating conditions (e.g., at ambient temperature, under atmospheric pressure, with or without continuous agitation), optionally following a period of incubation (e.g., minutes to hours, such as 1 hour or less) sufficient to allow the reaction mixture reach equilibrium. The optional incubation can be carried out under normal operation conditions, such as the same conditions when the separate solutions are combined. In another example, the reaction mixture as a dispersion is visibly clarified by one or more means such as, for example, heating or cooling to another pre-determined temperature, as well as other dissolution means such as dilution. While it is not necessary for the reaction mixture to be visibly clear prior to the formation of the microparticles, a visibly clear reaction mixture allows greater degrees of control over the characteristics (e.g., particle size distribution, aerodynamic and geometric particle sizes, particle morphology, particle uniformity) of the microparticles formed subsequently. In another example, the separate solutions are pre-heated at a common pre-determined temperature or different pre-determined temperatures and combined in any appropriate order (optionally at the pre-heated temperature), optionally heated or cooled to another temperature higher or lower than the pre-heated temperature following the combination.

Non-Ionic Polymer.

The non-ionic polymers of the present disclosure serve to enhance and/or induce the liquid-solid phase separation of the nucleic acids from the reaction solution, in which the nucleic acid molecules aggregate with the non-polymeric cations to become solid or semi-solid to form microparticles as a discontinuous phase suspendably dispersed in the aqueous medium in which the non-ionic polymers remain dissolved. The non-ionic polymers reduce the solubility of the nucleic acids when the reaction solution is brought to the phase separation conditions. Suitable non-ionic polymers include, but are not limited to, polymers or mixtures of polymers that are soluble or miscible with water and/or the aqueous medium of the reaction solution. Examples of suitable non-ionic polymers include linear or branched non-ionic polymers.

Non-ionic polymers that are water-soluble and/or water-miscible include carbohydrate-based non-ionic polymers, non-ionic amphiphilic polymers, non-ionic polyaliphatic alcohols, non-ionic poly(vinyl) polymers, non-ionic polyesters (e.g., non-ionic polyacrylic acids, non-ionic polyorganic acids), non-ionic polyamino acids, non-ionic co-polymers and non-ionic block co-polymers (e.g., poloxamers such as Pluronics F127 or F68), non-ionic terpolymers, non-ionic polyethers, naturally occurring non-ionic polymers, non-ionic polyimides, non-ionic cyclo-polymers, and non-ionic polyaldehydes, used singly or in combination of two or more thereof (e.g., weight ratio between any two polymers ranging from 1:1 to 99:1).

Preferred non-ionic polymers are ones that are acceptable as pharmaceutical additives for the intended route of administration of the nucleic acid microparticles. These include polyethylene glycol (PEG) of 1 kD to 1,000 kD in molecular weight, such as PEG 3350, PEG 8000, PEG 10000, PEG 20000, etc. poloxamers of 1 kD or greater in molecular weight, such as Pluronics F127 or Pluronics F68, polyvinylpyrrolidone (PVP), and combinations thereof (e.g., 1:1 mixture of PEG and PVP).

Liquid-Solid Phase Separation.

A liquid-solid phase separation of the nucleic acids in the reaction solution can be induced by any method known in the art, such as change in temperature, change in pressure, change in pH, change in ionic strength of the solution, change in the concentration of the one or more solutes therein, change in osmolality of the solution, combinations of these, and the like.

In one example of the present disclosure, the phase change is a temperature-induced phase change achieved by lowering the temperature of the reaction solution below the phase transition temperature of the nucleic acids that are solubilized in the reaction solution, without freezing the entire reaction solution.

In the cooling process, the rate of cooling is controlled to yield microparticles of desired size and shape. For example, it is found that all else being equal, the rate of cooling appears to be inversely correlated to the geometric size of the microparticles. That is, slower rates appears to form larger microparticles, while faster rates appears to form smaller microparticles. For delivery to moist or aqueous target locations such as areas in the lung, the cooling rate is 0.01° C./minute or faster, such as being equal to or greater than the following values, or in a range between any two of such values: 0.05° C./minute, 0.1° C./minute, 0.5° C./minute, 1° C./minute, 3° C./minute, 5° C./minute, 10° C./minute, 20° C./minute, 50° C./minute, 100° C./minute, 200° C./minute, 500° C./minute, 600° C./minute. The rate of temperature change can be at a constant or linear rate, a non-linear rate, intermittent, or a programmed rate (having multiple phase cycles).

The nucleic acid microparticles can be separated from the reaction solution by washing as will be discussed below.

The present disclosure contemplates adjusting the concentration of the solutes (e.g., nucleic acids, non-polymeric cations, non-ionic polymers), the temperature, the pressure, the pH, the ionic strength, the osmolality and the like or any combination of these parameters of the reaction solution to control (e.g., induce or terminate) or modulate (e.g., enhance, promote, suppress) a phase change where the nucleic acid molecules go from a solvated state to an aggregated solid state while the non-ionic polymers and solvent do not go through a phase change. For reaction solutions in which the freezing point is relatively high, or the freezing point is above the phase transition temperature, the reaction solutions can include one or more freezing point depressing agents, such as propylene glycol, sucrose, ethylene glycol, alcohols (e.g., ethanol, methanol) or mixtures of freezing-point depression agents to lower the freezing point of the reaction solution to allow the phase change of the nucleic acids to take place without freezing the reaction solution. The process can also be carried out such that the temperature of the reaction solution is reduced below its freezing point.

Separating and Washing the Microparticles.

In one example of the present disclosure, the dispersion containing the newly formed nucleic acid microparticles dispersed in suspension in the reaction solution is suitable for end use as is. In another example, the nucleic acid microparticles are harvested by separating them from the reaction solution. In yet another example, the method of separation involves concentrating the nucleic acid microparticles and washing them with a non-solvent liquid medium in which the components not incorporated into the microparticles (e.g., non-ionic polymers, excess reagents) are soluble. Non-limiting methods of concentrating the microparticles include centrifugation, dialysis, and diafiltration. Non-limiting methods of washing include diafiltration, dialysis, centrifugal washing. The liquid washing medium can be an aqueous medium or an organic solvent. For microparticles with low aqueous solubility, the liquid washing medium can be an aqueous medium or an aqueous medium containing agents that reduce the aqueous solubility of the microparticles, such as the non-polymeric cations disclosed herein (e.g., divalent cations). For active agents with high aqueous solubility, an organic solvent or an aqueous solvent containing one or more solubility reducing agents such as ammonium sulfate may be used.

Examples of suitable organic solvents for use as the liquid washing medium include those organic solvents specified above as suitable for the continuous phase, and more preferably methylene chloride, chloroform, acetonitrile, ethylacetate, methanol, ethanol, pentane, and the like.

It is also contemplated to use mixtures of any of these solvents as the washing medium. One preferred blend is methylene chloride or a 1:1 mixture of methylene chloride and acetone. It is preferred that the liquid medium has a low boiling point for easy removal by, for example, lyophilization, evaporation, or drying.

The liquid washing medium can also be a supercritical fluid, such as liquid carbon dioxide or a fluid near its supercritical point. Supercritical fluids can be suitable solvents for the non-ionic polymers, but are nonsolvents for nucleic acid microparticles. Supercritical fluids can be used by themselves or with a co-solvent. The following supercritical fluids can be used: liquid $CO_2$, ethane, or xenon. Potential co-solvents can be acetontitrile, dichloromethane, ethanol, methanol, water, or 2-propanol.

The liquid washing medium may further contain one or more solubility reducing agents for the microparticles. It is most desirable that the microparticles exhibit minimal solubility in the liquid washing medium to maximize the yield of the microparticles. For the nucleic acid microparticles in the present disclosure, solubility reducing agents can be any of the non-polymeric cations disclosed herein, including but not limited to, $Zn^{2+}$, $Ca^{2+}$, $Ba^{2+}$, $Mg^{2+}$, $Cu^{2+}$, $Fe^{2+}$, $Fe^{3+}$, and the like.

The liquid washing medium may also contain one or more additives which may imbue nucleic acids or the microparticles with additional characteristics such as increased stability of the microparticles and/or of the nucleic acid molecules therein, controlled release of the nucleic acids from the microparticles, or modified interactions (e.g., permeation) of the nucleic acids with biological tissues and cells as discussed previously.

Aqueous-Based Process.

In another example, the reaction solution is of an aqueous system including an aqueous or an aqueous-miscible solvent. Examples of suitable aqueous-miscible solvents include, but are not limited to, those identified above for the continuous phase. One advantage of using an aqueous-based process is that the solution can be buffered and can contain additives that provide, for example, biochemical stabilization to protect the nucleic acid molecules.

The following table lists exemplary nucleic acid microparticle formulations in which calcium cation is used as an exemplary non-polymeric cation. Also listed are corresponding final salt (of the non-polymeric cation) concentration in the reaction solution, the molar ratio of [nucleic acid]:[non-polymeric cation], the mean diameters of the microparticles, the cut-off diameters for 10% of the microparticles (i.e., 10% of the microparticles have diameters equal to or less than this value while 90% of the microparticles have diameters greater than this value), the cut-off diameters for 50% of the microparticles, and the cut-off diameters for 95% of the microparticles.:

| Sample Final [Salt] (Molar ratio of [nucleic acid]:[non-polymeric cation]) | Density Used | Diameter Calc. | Mean Diameter (um) | St Dev | 10% Under (um) | 50% Under (um) | 95% Under (um) |
|---|---|---|---|---|---|---|---|
| 1.243M (1:6477) | 1.45 | Number | 1.239 | 1.223 | 0.947 | 1.250 | 1.699 |
| 1.243M (1:6477) | 1.45 | Volume | 1.389 | 1.209 | 1.083 | 1.401 | 1.861 |
| 0.994M (1:4858) | 1.45 | Number | 1.501 | 1.246 | 1.122 | 1.512 | 2.129 |
| 0.994M (1:4858) | 1.45 | Volume | 1.718 | 1.226 | 1.313 | 1.736 | 2.339 |
| 0.667M (1:3239) | 1.45 | Number | 2.103 | 1.117 | 1.833 | 2.112 | 2.499 |
| 0.667M (1:3239) | 1.45 | Volume | 2.180 | 1.118 | 1.910 | 2.174 | 2.627 |
| 0.333M (1:1619) | 1.45 | Number | 2.114 | 1.117 | 1.839 | 2.128 | 2.505 |
| 0.333M (1:1619) | 1.45 | Volume | 2.191 | 1.117 | 1.920 | 2.189 | 2.631 |

From the above data, it was seen that 0.333M and 0.667M calcium salt concentrations yielded the similarly sized microparticles and the 1M and 1.25 M salt concentrations yielded relatively smaller microparticles. These and related data are discussed in further detail below. These data demonstrate that the use of an non-polymeric cation, such as $Ca^{2+}$ allows the formation of nucleic acid microparticles that can readily be prepared in a controllable size-range for use in pulmonary delivery.

In specific embodiments of the invention that include microspheres comprised of nucleic acids modified to include a lipophilic moiety, methods are provided for producing such microspheres comprising the steps of incubating a mixture of an aqueous solution of one or more modified nucleic acids with a solution of one or more polymers and one or more cations with heat, and cooling the mixture to form microspheres. In various aspects, the method comprising a first step of dissolving the modified nucleic acid in an aqueous solution, preparing a polymer/cation solution, mixing the modified nucleic acid solution and the polymer/cation solution, incubating the mixture of modified nucleic acids, polymers and cation at elevated heat for a set time, and cooling the mixture at a set rate to form microspheres. In certain aspects, the resulting microspheres are solid, spherical and/or monodispersed or substantially solid, spherical, and/or monodispersed.

In various aspects of the methods provided, a polymer utilized in production of the microspheres is one or more of a linear polymer (e.g., polyethylene glycol, polylysine, dextran, etc.), a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 Oct. 1993); a lipid; a cholesterol group (such as a steroid); or a carbohydrate or oligosaccharide. Other possible carriers include one or more water soluble polymer attachments such as polyoxyethylene glycol, or polypropylene glycol as described U.S. Pat. Nos. 4,640,835, 4,496,689, 4,301,144, 4,670,417, 4,791,192 and 4,179,337. Still other useful polymers known in the art include monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide copolymer, polyoxyethylated polyols (e.g., glycerol) and polyvinyl alcohol, as well as mixtures of these polymers and other polymers described herein. It is contemplated that use of "one or more" polymers in a method provided indicates that mixtures of polymers can be included in the method.

In various aspects, the final concentration of the polymer or combination of polymers, when combined with the modified nucleic acid, used in the methods is about 5% weight/volume (w/v), 5.1% w/v, 5.2% w/v, 5.3% w/v, 5.4% w/v, 5.5% w/v, 5.6% w/v, 5.7% w/v, 5.8% w/v, 5.9% w/v, 6% w/v, 6.1% w/v, 6.2% w/v, 6.3% w/v, 6.4% w/v, 6.5% w/v, 6.6% w/v, 6.7% w/v, 6.8% w/v, 6.9% w/v, 7% w/v, 7.1% w/v, 7.2% w/v, 7.3% w/v, 7.4% w/v, 7.5% w/v, 7.6% w/v, 7.7% w/v, 7.8% w/v, 7.9% w/v, 8% w/v, 8.1% w/v, 8.2% w/v, 8.3% w/v, 8.4% w/v, 8.5% w/v, 8.6% w/v, 8.7% w/v, 8.8% w/v, 8.9% w/v, 9% w/v, 9.1% w/v, 9.2% w/v, 9.3% w/v, 9.4% w/v, 9.5% w/v, 9.6% w/v, 9.7% w/v, 9.8% w/v, 9.9% w/v, 10% w/v, 10.1% w/v, 10.2% w/v, 10.3% w/v, 10.4% w/v, 10.5% w/v, 10.6% w/v, 10.7% w/v, 10.8% w/v, 10.9% w/v, 11% w/v, 11.1% w/v, 11.2% w/v, 11.3% w/v, 11.4% w/v, 11.5% w/v, 11.6% w/v, 11.7% w/v, 11.8% w/v, 11.9% w/v, 12% w/v, 12.1% w/v, 12.2% w/v, 12.3% w/v, 12.4% w/v, 12.5% w/v, 12.6% w/v, 12.7% w/v, 12.8% w/v, 12.9% w/v, 13% w/v, 13.1% w/v, 13.2% w/v, 13.3% w/v, 13.4% w/v, 13.5% w/v, 13.6% w/v, 13.7% w/v, 13.8% w/v, 13.9% w/v, 14% w/v, 14.1% w/v, 14.2% w/v, 14.3% w/v, 14.4% w/v, 14.5% w/v, 14.6% w/v, 14.7% w/v, 14.8% w/v, 14.9% w/v, 15% w/v, 15.1% w/v, 15.2% w/v, 15.3% w/v, 15.4% w/v, 15.5% w/v, 15.6% w/v, 15.7% w/v, 15.8% w/v, 15.9% w/v, 16% w/v, 16.1% w/v, 16.2% w/v, 16.3% w/v, 16.4% w/v, 16.5% w/v, 16.6% w/v, 16.7% w/v, 16.8% w/v, 16.9% w/v, 17% w/v, 17.1% w/v, 17.2% w/v, 17.3% w/v, 17.4% w/v, 17.5% w/v, 17.6% w/v, 17.7% w/v, 17.8% w/v, 17.9% w/v, 18% w/v, 18.1% w/v, 18.2% w/v, 18.3% w/v, 18.4% w/v, 18.5% w/v, 18.6% w/v, 18.7% w/v, 18.8% w/v, 18.9% w/v, 19% w/v, 19.1% w/v, 19.2% w/v, 19.3% w/v, 19.4% w/v, 19.5% w/v, 19.6% w/v, 19.7% w/v, 19.8% w/v, 19.9% w/v, 20% w/v, 20.1% w/v, 20.2% w/v, 20.3% w/v, 20.4% w/v, 20.5% w/v, 20.6% w/v, 20.7% w/v, 20.8% w/v, 20.9% w/v, 21% w/v, 21.1% w/v, 21.2% w/v, 21.3% w/v, 21.4% w/v, 21.5% w/v, 21.6% w/v, 21.7% w/v, 21.8% w/v, 21.9% w/v, 22% w/v, 22.1% w/v, 22.2% w/v, 22.3% w/v, 22.4% w/v, 22.5% w/v, 22.6% w/v, 22.7% w/v, 22.8% w/v, 22.9% w/v, 23% w/v, 23.1% w/v, 23.2% w/v, 23.3% w/v, 23.4% w/v, 23.5% w/v, 23.6% w/v, 23.7% w/v, 23.8% w/v, 23.9% w/v, 24% w/v, 24.1% w/v, 24.2% w/v, 24.3% w/v, 24.4% w/v, 24.5% w/v, 24.6% w/v, 24.7% w/v, 24.8% w/v, 24.9% w/v, 25% w/v, 25.1% w/v, 25.2% w/v, 25.3% w/v, 25.4% w/v, 25.5% w/v, 25.6% w/v, 25.7% w/v, 25.8% w/v, 25.9% w/v, 26% w/v, 26.1% w/v, 26.2% w/v, 26.3% w/v, 26.4% w/v, 26.5% w/v, 26.6% w/v, 26.7% w/v, 26.8% w/v, 26.9% w/v, 27% w/v, 27.1% w/v, 27.2% w/v, 27.3% w/v, 27.4% w/v, 27.5% w/v, 27.6% w/v, 27.7% w/v, 27.8% w/v, 27.9% w/v, 28% w/v, 28.1% w/v, 28.2% w/v, 28.3% w/v, 28.4% w/v, 28.5% w/v, 28.6% w/v, 28.7% w/v, 28.8% w/v, 28.9% w/v, 29% w/v, 29.1% w/v, 29.2% w/v, 29.3% w/v, 29.4% w/v, 29.5% w/v, 29.6% w/v, 29.7% w/v, 29.8% w/v, 29.9% w/v, 30% w/v, 30.1% w/v, 30.2% w/v, 30.3% w/v, 30.4% w/v, 30.5% w/v, 30.6% w/v, 30.7% w/v, 30.8% w/v, 30.9% w/v, 31% w/v, 31.1% w/v, 31.2% w/v, 31.3% w/v, 31.4% w/v, 31.5% w/v, 31.6% w/v, 31.7% w/v, 31.8% w/v, 31.9% w/v, 32% w/v, 32.1% w/v, 32.2% w/v, 32.3% w/v, 32.4% w/v, 32.5% w/v, 32.6% w/v, 32.7% w/v, 32.8% w/v, 32.9% w/v, 33% w/v, 33.1% w/v, 33.2% w/v, 33.3% w/v, 33.4% w/v, 33.5% w/v, 33.6% w/v, 33.7% w/v, 33.8% w/v, 33.9% w/v, 34% w/v, 34.1% w/v, 34.2% w/v, 34.3% w/v, 34.4% w/v, 34.5% w/v, 34.6% w/v, 34.7% w/v, 34.8% w/v, 34.9% w/v, 35% w/v or greater.

In methods for preparing microspheres comprised on modified nucleic acids, the cation utilized is in one aspect a polyvalent cation as described herein and/or otherwise known in the art, and in the method, the polyvalent cation is mixed with the modified nucleic acid(s) at a molar ratio of cation: nucleic acid of about 1:1, 2:1, 3:1, 4:1; 5:1, 6:1, 7:1, 8:1, 9:1, 10:1; 11:1, 12:1, 13:1, 14:1; 15:1, 16:1, 17:1, 18:1, 19:1, 20:1; 21:1, 22:1, 23:1, 24:1; 25:1, 26:1, 27:1, 28:1; 29:1, 30:1; 31:1, 32:1, 33:1, 34:1; 35:1, 36:1, 37:1, 38:1, 39:1, 40:1; 41:1, 42:1, 43:1, 44:1; 45:1, 46:1, 47:1, 48:1, 49:1, 50:1; 51:1, 52:1, 53:1, 54:1; 55:1, 56:1, 57:1, 58:1, 59:1, 60:1; 61:1, 62:1, 63:1, 64:1; 65:1, 66:1, 67:1, 68:1, 69:1, 70:1; 71:1, 72:1, 73:1, 74:1; 75:1, 76:1, 77:1, 78:1, 79:1, 80:1; 81:1, 82:1, 83:1, 84:1; 85:1, 86:1, 87:1, 88:1, 89:1, 90:1; 91:1, 92:1, 93:1, 94:1; 95:1, 96:1, 97:1, 98:1, 99:1, 100:1; 101:1, 102:1, 103:1, 104:1; 105:1, 106:1, 107:1, 108:1, 109:1, 110; 110:1; 111:1, 112:1, 113:1, 114:1; 115:1, 116:1, 117:1, 118:119:1, 120:1; 121:1, 122:1, 123:1, 124:1; 125:1, 126:1, 127:1, 128:1, 129:1, 130:1; 131:1, 132:1, 133:1, 134:1; 135:1, 136:1, 137:1, 138:1, 139:1, 140:1; 141:1, 142:1, 143:1, 144:1; 145:1, 146:1, 147:1, 148:1, 149:1, 150:1; 151:1, 152:1, 153:1, 154:1; 155:1, 156:1, 157:1, 158:1, 159:1, 160:1; 161:1, 162:1, 163:1, 164:1; 165:1, 166:1, 167:1, 168:1, 169:1, 170:1; 171:1, 172:1, 173:1, 174:1; 175:1, 176:1, 177:1, 178:1, 179:1, 180:1; 181:1, 182:1, 183:1, 184:1; 185:1, 186:1, 187:1, 188:1, 189:1, 190:1; 191:1, 192:1, 193:1, 194:1; 195:1, 196:1, 197:1, 198:1, 199:1, 200:1; 201:1, 202:1, 203:1, 204:1; 205:1, 206:1, 207:1, 208:1, 209:1, 210:1; 211:1, 212:1, 213:1, 214:1; 215:1, 216:1, 217:1, 218:1, 219:1, 220:1; 221:1, 222:1, 223:1, 224:1; 225:1, 226:1, 227:1, 228:1, 229:1, 230:1; 231:1, 232:1, 233:1, 234:1; 235:1, 236:1, 237:1, 238:1, 239:1, 240:1; 241:1, 242:1, 243:1, 244:1; 245:1, 246:1, 247:1, 248:1, 249:1, 250:1; 251:1, 252:1, 253:1, 254:1; 255:1, 256:1, 257:1, 258:1, 259:1, 260:1; 261:1, 262:1, 263:1, 264:1; 265:1, 266:1, 267:1, 268:1, 269:1, 270:1; 271:1, 272:1, 273:1, 274:1; 275:1, 276:1, 277:1, 278:1, 279:1, 280:1; 281:1, 282:1, 283:1, 284:1; 285:1, 286:1, 287:1, 288:1, 289:1, 290:1; 291:1, 292:1, 293:1, 294:1; 295:1, 296:1, 297:1, 298:1, 299:1, 300:1; 301:1, 302:1, 303:1, 304:1; 305:1, 306:1, 307:1, 308:1, 309:1, 310:1; 311:1, 312:1, 313:1, 314:1; 315:1, 316:1, 317:1, 318:1, 319:1, 320:1; 321:1, 322:1, 323:1, 324:1; 325:1, 326:1, 327:1, 328:1, 329:1, 330:1; 331:1, 332:1, 333:1, 334:1; 335:1, 336:1, 337:1, 338:1, 339:1, 340:1; 341:1, 342:1, 343:1, 344:1; 345:1, 346:1, 347:1, 348:1, 349:1, 350:1; 351:1, 352:1, 353:1, 354:1; 355:1, 356:1, 357:1, 358:1, 359:1, 360:1; 361:1, 362:1, 363:1, 364:1; 365:1, 366:1, 367:1, 368:1, 369:1, 370:1; 371:1, 372:1, 373:1, 374:1; 375:1, 376:1, 377:1, 378:1, 379:1, 380:1; 381:1, 382:1, 383:1, 384:1; 385:1, 386:1, 387:1, 388:1, 389:1, 390:1; 391:1, 392:1, 393:1, 394:1; 395:1, 396:1, 397:1, 398:1, 399:1, 400:1; 401:1, 402:1, 403:1, 404:1; 405:1, 406:1, 407:1, 408:1, 409:1, 410:1; 411:1, 412:1, 413:1, 414:1; 415:1, 416:1, 417:1, 418:1, 419:1, 420:1; 421:1, 422:1, 423:1, 424:1; 425:1, 426:1, 427:1, 428:1, 429:1, 430:1; 431:1, 432:1, 433:1, 434:1; 435:1, 436:1, 437:1, 438:1, 439:1, 440:1; 441:1, 442:1, 443:1, 444:1; 445:1, 446:1, 447:1, 448:1, 449:1, 450:1; 451:1, 452:1, 453:1, 454:1; 455:1, 456:1, 457:1, 458:1, 459:1, 460:1; 461:1, 462:1, 463:1, 464:1; 465:1, 466:1, 467:1, 468:1, 469:1, 470:1; 471:1, 472:1, 473:1, 474:1; 475:1, 476:1, 477:1, 478:1, 479:1, 480:1; 481:1, 482:1, 483:1, 484:1; 485:1, 486:1, 487:1, 488:1, 489:1, 490:1; 491:1, 492:1, 493:1, 494:1; 495:1, 496:1, 497:1, 498:1, 499:1, 500:1, 1; 550:1, 600:1, 650:1, 700:1, 750:1, 800:1; 850:1, 900:1, 950:1, 1000:1; 1100:1, 1200:1, 1300:1, 1400:1, 1500:1, 1600:1; 1700:1, 1800:1, 1900:1, 2000:1; 2100:1, 2200:1, 2300:1, 2400:1, 2500:1, 2600:1; 2700:1, 2800:1, 2900:1, 3000:1; 3100:1, 3200:1, 3300:1, 3400:1, 3500:1, 3600:1; 3700:1, 3800:1, 3900:1, 4000:1; 4100:1, 4200:1, 4300:1, 4400:1, 4500:1, 4600:1; 4700:1, 4800:1, 4900:1, 5000:1; 5100:1, 5200:1, 5300:1, 5400:1, 5500:1, 5600:1; 5700:1, 5800:1, 5900:1, 6000:1; 6100:1, 6200:1, 6300:1, 6400:1, 6500:1, 6600:1; 6700:1, 6800:1, 6900:1, 7000:1; 7100:1, 7200:1, 7300:1, 7400:1, 7500:1, 7600:1; 7700:1, 7800:1, 7900:1, 8000:1; 8100:1, 8200:1, 8300:1, 8400:1, 8500:1, 8600:1; 8700:1, 8800:1, 8900:1, 9000:1; 9100:1, 9200:1, 9300:1, 9400:1, 9500:1, 9600:1; 9700:1, 9800:1, 9900:1, 10000:1; or greater.

The polycation concentration in a mixture of polycation, water soluble polymer and nucleic acid from about 5 mM to greater than 1 M, or from about 10 mM to about 20 mM, to about 25 nM or to about 35 mM. as well as all concentrations within these ranges. More specifically, the final polycation concentration is about 5 mM, about 10 mM, about 15 mM about 20 mM, about 25 mM, about 30 mM, about 35 mM, about 40, about 45 mM, about 50 mM, about 55 mM about 60 mM, about 65 mM, about 70 mM, about 75 mM, about 80, about 85 mM, about 90 mM, about 95 mM, about 100 mM, 105 mM, about 110 mM, about 115 mM about 120 mM, about 125 mM, about 130 mM, about 135 mM, about 140, about 145 mM, about 150 mM, about 155 mM about 160 mM, about 165 mM, about 170 mM, about 175 mM, about 180, about 185 mM, about 190 mM, about 195 mM about 200 mM, 205 mM, about 210 mM, about 215 mM about 220 mM, about 225 mM, about 230 mM, about 235 mM, about 240, about 245 mM, about 250 mM, about 255 mM about 260 mM, about 265 mM, about 270 mM, about 275 mM, about 280, about 285 mM, about 290 mM, about 295 mM about 300 mM, about 305 mM, about 310 mM, about 315 mM about 320 mM, about 325 mM, about 330 mM, about 335 mM, about 340, about 345 mM, about 350 mM, about 355 mM about 360 mM, about 365 mM, about 370 mM, about 375 mM, about 380, about 385 mM, about 390 mM, about 395 mM, about 400 mM, about 405 mM, about 410 mM, about 415 mM about 420 mM, about 425 mM, about 430 mM, about 435 mM, about 440, about 445 mM, about 450 mM, about 455 mM about 460 mM, about 465 mM, about 470 mM, about 475 mM, about 480, about 485 mM, about 490 mM, about 495 mM, about 500 mM, 505 mM, about 510 mM, about 515 mM about 520 mM, about 525 mM, about 530 mM, about 535 mM, about 540, about 545 mM, about 550 mM, about 555 mM about 560 mM, about 565 mM, about 570 mM, about 575 mM, about 580, about 585 mM, about 590 mM, about 595 mM, about 600 mM, 605 mM, about 610 mM, about 615 mM about 620 mM, about 625 mM, about 630 mM, about 635 mM, about 640, about 645 mM, about 650 mM, about 655 mM about 660 mM, about 665 mM, about 670 mM, about 675 mM, about 680, about 685 mM, about 690 mM, about 695 mM, about 700 mM, about 705 mM, about 710 mM, about 715 mM about 720 mM, about 725 mM, about 730 mM, about 735 mM, about 740, about 745 mM, about 750 mM, about 755 mM about 760 mM, about 765 mM, about 770 mM, about 775 mM, about 780, about 785 mM, about 790 mM, about 795 mM, about 800 mM, about 805 mM, about 810 mM, about 815 mM about 820 mM, about 825 mM, about 830 mM, about 835 mM, about 840, about 845 mM, about 850 mM, about 855 mM about 860 mM, about 865 mM, about 870 mM, about 875 mM, about 880, about 885 mM, about 890 mM, about 895 mM, about 900 mM, about 905 mM, about 910 mM, about 915 mM about 920 mM, about 925 mM, about 930 mM, about 935 mM, about 940, about 945 mM, about 950 mM, about 955 mM about 960 mM, about 965 mM, about 970 mM, about 975 mM, about 980, about 985 mM, about 990 mM, about 995 mM, about 1 M, about 1.1 M, about 1.2 M, about 1.3 M, about 1.4 M, about 1.5 M, about 1.6 M, about 1.7 M, about 1.8 M, about 1.9 M, about 2.0 M, about 2.1 M, about 2.2 M, about 2.3 M, about 2.4 M, about 2.5 M, about 2.6 M, about 2.7 M, about 2.8 M, about 2.9 M, about 3.0 M or greater than 3 M.

In the methods for preparing microspheres comprising modified nucleic acids incubation of the nucleic acid aqueous nucleic acid solution and the polymer/cation solution is performed at about 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., or higher. This incubation step is carried out for about 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, 30 min or longer. After the incubation step is completed, the mixture is then cooled to a final temperature of about lower than −10° C., to about −10° C., to about −9° C., to about −8° C., to about −7° C., to about −6° C., to about −5° C., to about −4° C., to about −3° C., to about −2° C., to about −1° C., to about 0, to about 1° C., to about 2° C., to about 3° C., to about 4° C., to about 5° C., to about 6° C., to about 7° C., to about 8° C., to about 9° C., to about 10° C., or higher, and the cooling step is carried out with a decrease in temperature at a rate of about less than about 0.1° C./min, up to about 0.1° C./min, 0.11° C./min; 0.12° C./min, 0.13° C./min, 0.14° C./min, 0.15° C./min, 0.16° C./min; 0.17° C./min, 0.18° C./min, 0.19° C./min, 0.2° C./min, 0.21° C./min; 0.22° C./min, 0.23° C./min, 0.24° C./min, 0.25° C./min, 0.26° C./min; 0.27° C./min, 0.28° C./min, 0.29° C./min, 0.3° C./min, 0.31° C./min, 0.32° C./min, 0.33° C./min, 0.34° C./min, 0.35° C./min, 0.36° C./min, 0.37° C./min, 0.38° C./min, 0.39° C./min, 0.40° C./min, 0.41° C./min, 0.42° C./min, 0.43° C./min, 0.44° C./min, 0.45° C./min, 0.46° C./min; 0.47° C./min, 0.48° C./min, 0.49° C./min, 0.50° C./min, 0.51° C./min, 0.52° C./min, 0.53° C./min, 0.54° C./min, 0.45° C./min, 0.56° C./min; 0.57° C./min, 0.58° C./min, 0.59° C./min, 0.60° C./min, 0.61° C./min; 0.62° C./min, 0.63° C./min, 0.64° C./min, 0.65° C./min, 0.66° C./min; 0.67° C./min, 0.68° C./min, 0.69° C./min, 0.70° C./min, 0.71° C./min; 0.72° C./min, 0.73° C./min, 0.74° C./min, 0.75° C./min, 0.76° C./min; 0.77° C./min, 0.78° C./min, 0.79° C./min, 0.80° C./min, 0.81° C./min; 0.82° C./min, 0.83° C./min, 0.84° C./min, 0.85° C./min, 0.86° C./min; 0.87° C./min, 0.88° C./min, 0.89° C./min, 0.90° C./min, 0.91° C./min; 0.92° C./min, 0.93° C./min, 0.94° C./min, 0.95° C./min, 0.96° C./min; 0.97° C./min, 0.98° C./min, 0.99° C./min, 1.0° C./min, 2.0° C./min, 3.0° C./min, 4.0° C./min, 5.0° C./min, 6.0° C./min, 7.0° C./min, 8.0° C./min, 9.0° C./min 10.0° C./min, 11.0° C./min, 12.0° C./min, 13.0° C./min, 14.0° C./min, 15.0° C./min, 16.0° C./min, 17.0° C./min, 18.0° C./min, 19.0° C./min, 20.0° C./min, 21.0° C./min, 22.0° C./min, 23.0° C./min, 24.0° C./min, 25.0° C./min, 26.0° C./min, 27.0° C./min, 28.0° C./min, 29.0° C./min, 30.0° C./min, 31.0° C./min, 32.0° C./min, 33.0° C./min, 34.0° C./min, 35.0° C./min, 36.0° C./min, 37.0° C./min, 38.0° C./min, 39.0° C./min, 40.0° C./min, 41.0° C./min, 42.0° C./min, 43.0° C./min, 44.0° C./min, 45.0° C./min, 46.0° C./min, 47.0° C./min, 48.0° C./min, 49.0° C./min, 50.0° C./min or faster. Flash cooling steps are also contemplated. While not being bound by any particular mechanism of action, the cooling step, and the way it is carried out, plays a role in determining the resulting size of the microspheres.

After the cooling step of the method, the microspheres are optionally collected, washed, re-suspended, and or dried to a powder.

Microspheres of the invention which include one or more modified nucleic acids, in one aspect, have an ability to enter cells and perform a biological function at least as efficiently as the same nucleic acid which is not part of a microsphere or modified as described herein. In another aspect, microspheres of the invention which include one or more modified nucleic acids, in one aspect, have an ability to enter cells and perform a biological function more efficiently than the same nucleic acid which is not part of a microsphere or modified as described herein.

D. Pharmaceutical Compositions Containing the Microparticles

As noted herein, the compositions of the present disclosure are prepared for delivery to moist or aqueous target locations such as the lung. The compositions are prepared such that they may be in an inhalable form. The inhalable form may be a dry powder, with or without a pharmaceutically acceptable excipient or diluent or the inhalable form may be in the form of a propellant-based dispersion with metered dosing. However, the nucleic acid microparticles are themselves free of any matrices of excipients, and do not form larger particles with the excipients when they are used. The inhalable form may be delivered orally or intranasally through the use of an inhaler or nasal spray. Thus, the disclosure provides a self administration method for patient treatment. Such administration may be used in a hospital, in a medical office or outside a hospital or medical office by non-medical personnel for nasal or inhalant self administration of the compositions of the disclosure.

Thus, in certain aspects of the disclosure, there is provided a device for patient self-administration of the compositions of the disclosure, which device comprises a nasal inhaler containing an aerosol formulation of the compositions of the disclosure and a pharmaceutically acceptable dispersant, wherein the device is metered to disperse an amount of the aerosol formulation that contains a desired dose of the compositions of the disclosure to alleviate or treat the symptoms of the disorder being treated. The dispersant may be any dispersant that is generally used in inhalant and spray compositions for example, a surfactant, such as, but not limited to, polyoxyethylene fatty acid esters, polyoxyethylene fatty acid alcohols, and polyoxyethylene sorbitan fatty acid ester or even phospholipid-based surfactants. However, it is noted that the inhalable devices of the disclosure need not necessarily employ such a dispersant.

In preferred examples, the compositions of the disclosure will be in the form of a dry powder aerosol formulation in which the composition is present as a finely divided powder. The dry powder formulation can further comprise a bulking agent, such as, but not limited to, lactose, sorbitol, sucrose and mannitol.

In another specific example, the aerosol formulation may be a liquid aerosol formulation further comprising a pharmaceutically acceptable diluent, such as, but not limited to, sterile water, saline, buffered saline and dextrose solution.

The compositions thus will preferably be prepared in a formulation or pharmaceutical composition appropriate for intranasal or inhalant administration, or mucosal administration in general. As used herein, compositions and formulations for delivery to mucosa include those that are therapeutically, prophylactically or diagnostically deliverable to buccal mucosa, esophageal mucosa, gastric mucosa, intestinal mucosa, olfactory mucosa, oral mucosa, bronchial mucosa, uterine mucosa, and endometrium as well as malignant cell types thereof. Suitable formulations can be formulated with a mucosal penetration enhancer to facilitate delivery of the compositions of the disclosure. A mucosal penetration enhancer is a reagent that increases the rate or facility of transmucosal penetration of the compositions of the disclosure, such as but not limited to, a bile salt, fatty acid, surfactant or alcohol. In specific examples, the permeation enhancer can be sodium cholate, sodium dodecyl sulphate, sodium deoxycholate, taurodeoxycholate, sodium glycocholate, dimethylsulfoxide or ethanol.

The formulation can also be prepared with pH optimized for solubility, drug stability, absorption through nasal mucosa, and other considerations.

Accordingly, the invention provides methods for delivering a therapeutic, prophylactic or diagnostic microparticle composition of the invention to mucosa comprising the step of contacting target mucosa with a microparticle composition in an amount effective to penetrate and act on or within the target mucosa.

The compositions of the disclosure are delivered in a therapeutically effective amount, i.e., an amount effective to demonstrate a desired activity of the drug. According to the instant disclosure, a therapeutically effective amount of a given nucleic acid will depend on the target for which it is being delivered. The therapeutic outcome of the delivery may be a decrease or alleviation of one or more of the symptoms of the disease being targeted and/or a decrease in the expression of the particular nucleic acid being targeted or activity of the protein whose expression is decreased as a result of the targeting.

As used herein, the term "aerosol" refers to suspension in the air. In particular, aerosol refers to the particalization or atomization of a formulation of the disclosure and its suspension in the air. According to the present disclosure, an aerosol formulation is a formulation comprising the microparticles of the disclosure for nasal inhalation or pulmonary administration through the oral cavity.

As used herein, the term "inhaler" refers both to devices for nasal and pulmonary administration of a drug, e.g., in solution, powder and the like. For example, a the term "inhaler" is intended to encompass a propellant driven inhaler, such as is used for to administer antihistamine for acute asthma attacks, and plastic spray bottles, such as are used to administer decongestants.

As used herein, the term "dispersant" refers to an agent that assists aerosolization of the compositions of the disclosure or absorption of these compositions in mucosal tissue, or both. However, it is noted that the microparticles of the disclosure have particularly good aerodynamic characteristics due to the uniform particle size distribution and their size range. In a specific aspect, the dispersant can be a mucosal penetration enhancer. Preferably, the dispersant is pharmaceutically acceptable. As used herein, the term "pharmaceutically acceptable" means approved by a regulatory agency of the Federal or a state government or listed in the U.S. Pharmacopeia or other generally recognized pharmacopeia for use in animals, and more particularly in humans.

The microparticles of the disclosure are non-aggregating and as such, it should not be necessary to use an agent to facilitate dispersion and "separateness" of the particles. If dispersing agents are used, however, they may include surfactants and the like. Such surfactants are generally used in the art to reduce surface induce aggregation of the agents being delivered caused by atomization of the solution forming the liquid aerosol and may be used in the methods and devices of the present disclosure. Examples of such surfactants include, but are not limited to, surfactants such as polyoxyethylene fatty acid esters and alcohols, and polyoxyethylene sorbitan fatty acid esters. Amounts of surfactants used will vary, being generally within the range or 0.001 and 4% by weight of the formulation. Suitable surfactants are well known in the art, and can be selected on the basis of desired properties, depending on the specific formulation, concentration of the oligonucleotides, diluent (in a liquid formulation) or form of powder (in a dry powder formulation), etc.

For liquid aerosol formulations the oligonucleotide microparticles can contain and a dispersing agent in a physiologically acceptable diluent. The dry powder aerosol formulations of the present disclosure consist of a finely divided lyophilized form of the microparticles and optionally, a dispersing agent.

"Lyophilize" or freeze drying refers to the preparation of a microparticle composition in dry form by rapid freezing and dehydration in the frozen state (sometimes referred to as sublimation). Lyophilization takes place at a temperature which results in the crystallization of the lipids to form a lipid matrix. This process may take place under vacuum at a pressure sufficient to maintain frozen product with the ambient temperature of the containing vessel at about room temperature, preferably less than about 500 mTorr, more preferably less than about 200 mTorr, even more preferably less than about 1 mTorr.

With either the liquid or dry powder aerosol formulation, the formulation will be aerosolized in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other parameters, such as construction of the delivery device, additional components in the formulation, and particle characteristics also should be considered. These aspects of nasal or pulmonary administration of a drug are well known in the art, and manipulation of formulations, aerosolization means and construction of a delivery device require at most routine experimentation by one of ordinary skill in the art.

For the method of delivery, any form of aerosolization known in the art, including but not limited to spray bottles, nebulization, atomization or pump aerosolization of a liquid formulation, and aerosolization of a dry powder formulation, can be used in the practice of the disclosure.

As noted above, in a preferred aspect of the disclosure, the device for aerosolization is an inhalable dry powder form in other preferred examples the device is a metered dose inhaler. A metered dose inhaler provides a specific dosage when administered, rather than a variable dose depending on administration. Such a metered dose inhaler can be used with either a liquid or a dry powder aerosol formulation. Metered dose inhalers are well known in the art.

For nasal administration, a useful device is a small, hard bottle to which a metered dose sprayer is attached. In one example, the metered dose is delivered by drawing the microparticle solution into a chamber of defined volume, which chamber has an aperture dimensioned to aerosolize and aerosol formulation by forming a spray when a liquid in the chamber is compressed. The chamber is compressed to administer the formulation. In a specific example, the chamber is a piston arrangement. Such devices are commercially available.

Alternatively, a plastic squeeze bottle with an aperture or opening dimensioned to aerosolize an aerosol formulation by forming a spray when squeezed. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the composition to be administered.

Often, the aerosolization of a liquid or a dry powder formulation for inhalation into the lung will require a propellant. The propellant may be any propellant generally used in the art. Specific non-limiting examples of such useful propellants are a chlorofluorocarbon, a hydrofluorocarbon, a hydrochlorofluorocarbon, or a hydrocarbon, including trifluoromethane, dichlorodifluoromethane, dichlorotetrafluoroethanol, and 1,1,1,2-tetrafluoroethane, or combinations thereof.

Liquid aerosol formulations and dosage forms also are contemplated. In general such dosage forms contain the compositions in a pharmaceutically acceptable diluent. Pharmaceutically acceptable diluents in such liquid aerosol formulations include but are not limited to sterile water, saline, buffered saline, dextrose solution, and the like. In a specific example, a diluent that may be used in the present disclosure or the pharmaceutical formulation of the present disclosure is phosphate buffered saline or a buffered saline solution generally between the pH 7.0-8.0 range, or water.

In addition, the formulations of the present example may also include other agents useful for pH maintenance, solution stabilization, or for the regulation of osmotic pressure. Examples of the agents include but are not limited to salts, such as sodium chloride, or potassium chloride, and carbohydrates, such as glucose, galactose or mannose, and the like.

E. In Vivo Delivery of the Particles

The nucleic acid microparticles in the present disclosure are suitable for in vivo delivery to a subject by a suitable route, such as injectable, topical, oral, rectal, nasal, pulmonary, vaginal, buccal, sublingual, transdermal, transmucosal, otic, intraocular or ocular. The microparticles can be delivered as a stable liquid suspension or formulated as a solid dosage form such as a dry powder. A preferred delivery route is pulmonary, which includes oral and nasal.

In this route of delivery, the microparticles may be selectively designed to deposit in the deep lung, in the upper respiratory tract, or anywhere in the respiratory tract. The microparticles may be delivered as a dry powder by a dry powder inhaler, or they may be delivered by a metered dose inhaler or a nebulizer.

Drugs intended to function systemically, are desirably deposited in the alveoli, where there is a very large surface area available for absorption into the bloodstream. When targeting the drug deposition to certain regions within the lung, the aerodynamic diameter of the microparticle can be adjusted to an optimal range by manipulating fundamental physical characteristics of the microparticles such as shape and size.

Acceptable respirable fractions of inhaled drug particles are often achieved by adding excipients to the formulation, either incorporated into the particle composition or as a mixture with the drug particles. For example, improved dispersion of micronized drug particles (about 5 µm) is effected by blending with larger (30-90 µm) particles of inert carrier particles such as trehalose, lactose or maltodextrin. The larger excipient particles improve the powder flow properties, which correlates with an improved pharmacodynamic effect. In a further refinement, the excipients are incorporated directly into the small spherical particles to effect aerosol performance as well as potentially enhancing the stability of protein drugs. Generally, excipients are chosen that have been previously FDA approved for inhalation, such as lactose, or organic molecules endogenous to the lungs, such as albumin and DL-.alpha.-phosphatidylcholine dipalmitoyl (DPPC). Other excipients, such as poly(lactic acid-co-glycolic acid) (PLGA) have been used to engineer particles with desirable physical and chemical characteristics. However, much of the inhalation experience with FDA approved excipients has been with asthma drugs having large aerodynamic particle sizes that desirably deposit in the tracheobronchial region, and which do not appreciably penetrate to the deep lung. For inhaled protein or peptide therapeutics delivered to the deep lung, there is concern that undesirable long-term side effects, such as inflammation and irritation can occur which may be due to an immunological response or caused by excipients when they are delivered to the alveolar region.

In order to minimize potential deleterious side effects of deep lung inhaled therapeutics, it may be advantageous to fabricate particles for inhalation that are substantially constituted by the drug to be delivered. This strategy would minimize alveolar exposure to excipients and reduce the overall mass dose of particles deposited on alveolar surfaces with each dose, possibly minimizing irritation during chronic use of the inhaled therapeutic. Small spherical particles with aerodynamic properties suitable for deep lung deposition that are essentially composed entirely of a therapeutic, prophylactic, and/or diagnostic protein, peptide or other agent as described herein may be particularly useful for isolated studies on the effects of chronic therapeutic or prophylactic dosing on the alveolar membrane of the lung. The effects of systemic delivery of protein, peptide or other agent in the form of small spherical particles by inhalation could then be studied without complicating factors introduced by associated excipients.

The requirements to deliver particles to the deep lung by inhalation are that the particles have a small mean aerodynamic diameter of 0.5-10 micrometers and a narrow size distribution. The disclosure also contemplates mixing together of various batches of particles having different particle size ranges. The process of the present disclosure allows the fabrication of microparticles with the above characteristics.

There are two principal approaches for forming particles with aerodynamic diameters of 0.5 to 3 micron. The first approach is to produce relatively large but very porous (or perforated) microparticles. Since the relationship between the aerodynamic diameter ($D_{aerodynamic}$) and the geometric diameter ($D_{geometric}$) is $D_{aerodynamic}$ is equal to $D_{geometric}$ multiplied by the square root of the density of the particles. Particles with very low mass density (around 0.1 g/cm$^3$) can exhibit small aerodynamic diameters (0.5 to 3 microns) while possessing relatively high geometric diameters (5 to 10 microns).

An alternative approach is to produce particles with relatively low porosity, in the case of the present disclosure, the particles have a density, set forth in the ranges above, and more generally that is close to 1 g/cm$^3$. Thus, the aerodynamic diameter of such non-porous dense particles is close to their geometric diameter.

The present method for particle formation set forth above, provides for particle formation with or without excipients.

Fabrication of small particles from nucleic acid itself with little or no additives other than the non-polymeric cation provides superior advantages for use in pulmonary delivery as it provides options for larger drug payloads, increased safety and decreased numbers of required inhalations.

H. Examples

The following section provides examples of methods and compositions used for the preparation of nucleic acid particle of the present disclosure. The scalability of the processes disclosed herein was demonstrated with various sized vessels of different materials, including 1.5 ml microfuge tube, 5 ml glass tube, 15 ml polypropylene tube, 10 ml jacketed glass vessel, 50 ml jacketed glass vessel and 100 ml jacketed glass vessel.

Exemplary nucleic acid microparticles of the present disclosure are prepared from a solution containing dissolved nucleic acids, non-ionic polymers, and non-polymeric cations. Relative concentrations of these solutes can be adjusted to optimize certain characteristics of the nucleic acid microparticles, such as particle size, shape (e.g., how spherical the microparticles are), and surface smoothness. The molarity of the non-polymeric cation typically ranges between 0.01M and 5M, such as 0.05M, 0.1M, 0.2M 0.3M, 0.4M 0.5M, 0.6M, 0.7M, 0.8M, 0.9M, 1M, 1.1M, 1.2M, 1.3M, 1.4M, 1.5M, 1.6M, 1.7M, 1.8M, 1.9M 2M, 2.1M, 2.2M, 2.3M, 2.4M, 2.5M, 2.6M, 2.7M, 2.8M, 2.9M, 3M, 3.1M, 3.2M, 3.3M, 3.4M, 3.5M, 3.6M, 3.7M, 3.8M, 3.9M, 4M, 4.1M, 4.2M, 4.3M, 4.4M, 4.5M, 4.6M, 4.7M, 4.8M, 4.9M, 5M, or in a range between any two of these values. The weight by volume concentration of the non-ionic polymer typically ranges from 5% to 50%, such as 8%, 10%, 15%, 20%, 25%, 30%, 35%, 40%, or in a range between any two of such values. The molar ratio of the nucleic acid to the non-polymeric cation typically ranges from 1:20 to 1:50,000, such as 1:20, 1:30, 1:40, 1:50, 1:60, 1:70, 1:80, 1:90, 1:100, 1:150, 1:200, 1:250, 1:300, 1:350, 1:400, 1:450, 1:500, 1:550, 1:600, 1:650, 1:700, 1:750, 1:800, 1:850, 1:900, 1:950, 1:1,000, 1:1,500, 1:2,000, 1:3,000, 1:4,000, 1:5,000, 1:6,000, 1:7,000, 1:8,000, 1:10,000, 1:15,000, 1:20,000, 1:30,000, 1:40,000, or in a range between any two of such values, or a ratio of otherwise described herein.

The present examples provide exemplary methods and compositions for preparing microparticles that may be used for pulmonary applications as described herein. These illustrative examples provide microparticles that are free of polymeric polycations. In addition, the microparticles prepared herein are soluble in water and/or aqueous solutions, a feature which enables the rapid release of the nucleic acids components of the microparticles when the microparticles are administered to predetermined sites, such as areas in the lung. The aerodynamic features of the microparticles, e.g., size and diameter, can be manipulated for targeted delivery, for example, to various predetermined areas within the lung.

Preferably, the microparticles prepared herein typically have a low moisture content (measured by Karl Fisher), for example, a moisture content of less than 8%. In addition, the microparticles have a non-polymeric cation content (as measured by atomic absorption) that is 3% or greater of the overall microparticle composition. A weight ratio of the dry powder of the resulting microparticles to the starting weight of the nucleic acid is about 1 or greater (e.g., for Ca-antisense microparticles the ratio was typically 1.03).

Example 1

Materials Used for the Preparation of Exemplary Microparticles

The following materials were used in the preparation of exemplary microparticles of the disclosure. While specific nucleic acids and siRNAs are provided for exemplary examples, similar microparticles can be prepared using other nucleic acids and oligonucleotides.

All aqueous solutions were prepared using nuclease-free, de-ionized water that was autoclaved and sterile filtered through a 0.2-micron filter.

Nucleic acid solutions were prepared at a concentration of about 15 mg/ml in water. Exemplary antisense oligodeoxynucleotides (anti-CD40, anti-CD80, anti-CD86) used in the methods described herein are commercially available in HPLC-purified lyophilized preparations. These oligonucleotides phosphorothioated in the oligonucleotide backbone and are available from Integrated DNA Technologies, (Coralville, Iowa).

Various siRNA compositions are used for the microparticles prepared herein. The siRNA molecules were made up of unmodified duplexes optionally having one strand labeled with a fluorescent dye. The duplexes consist of two 21-mer RNA oligonucleotides base-pair annealed together with each 21-mer having a 2-nucleotide-long 3'-overhang. As negative controls SCR-027, NT-2 and NT2 labeled with fluorescent dye DY547 were used and the active siRNA molecules labeled with fluorescent dye DY547 were directed against eGFP. HPLC-purified and lyophilized preparations of these siRNA molecules are commercially available from Dharmacon (Dharmacon, Lafayette, Colo.).

The non-polymeric cation stock solutions were prepared by dissolving salts of the non-polymeric cation (in anhydrous or hydrate form) in water at a concentration of 1M to 10M. The pH of the stock solutions was adjusted to a pH near neutral to acidic (e.g., 3 to 7.5);

Non-ionic Polymer solution A was made up of 12.5% (w/v) PEG 3350 (average MW 3409D) and 12.5% (w/v) PVP (average MW 40 kD) in 0.1M NaOAc buffer at an acidic pH (e.g., 5.6).

Non-ionic Polymer solution B was made up of 25% (w/v) PEG 3350 in 0.1M NaOAc buffer at an acidic pH (e.g., 5.6).

Non-ionic Polymer solution C was made up of 24% (w/v) poloxamer 188 (average MW 8400, Lutrol® F68 from BASF), pH 5.6 (adjusted with HOAc).

Non-ionic Polymer solution D was made up of 50% (w/v) PEG 3350 in 0.167 M NaOAc buffer at an acidic pH (e.g., 5.6). Final concentration of the polymer in reaction mixtures using Non-ionic Polymer solution D was typically 20% (w/v) PEG 3350 in 0.067 M NaOAc buffer.

Example 2

Exemplary Microparticles of Antisense Oligonucleotides Prepared with $Ca^{2+}$ as a Cation The following example provides two exemplary processes for the preparation of $Ca^{2+}$-containing antisense oligonucleotide-based microparticles of the disclosure.

Preparation Process 1:

In this process, a series of six reaction mixtures was prepared in which each reaction mixture contained the non-ionic polymer solution, the salt solution and the nucleic acid solution. Briefly, aliquots of non-ionic polymer solution A were dispensed into a vessel such that two-thirds of each final reaction mixture would contain solution A. Salt solution (5M $CaCl_2$ stock solution, pH 5.5) and water were added to the non-ionic polymer aliquots such that Ca concentrations in the final reaction mixtures were 0.1M, 0.17M, 0.33M, 0.67M, 1M, and 1.25M, respectively. Aliquots of antisense nucleic acid solution were prepared such that when these aliquots of nucleic acid solution were added to the final reaction mixture, the concentration of the antisense nucleic acid in each final reaction mixture would be 0.206 mM.

The salt/polymer reaction mixtures and the nucleic acid aliquots were pre-heated and then combined to form the final reaction mixtures. The final reaction mixtures were incubated for 5 minutes, all at about the same incubation temperature. The reaction with the series of reaction mixtures was repeated over a range of different temperatures (e.g., 60° C., 65° C., or 70° C.). All reaction mixtures, with the exception of reaction mixtures containing 1.25M Ca became turbid initially upon mixing, and turned visibly clear (i.e., indicating that the reaction mixtures were homogeneous, single-phase solutions) by the end of the incubation. The reaction mixture containing 1.25M and 1M Ca remained turbid even when further heated to 75° C. The reaction mixtures were cooled to 4° C. at controlled rates (ranging from 0.1° C./min to 5° C./min). Ca-antisense microparticles were dispersed in all reaction mixtures as visualized with light microscopy. Ca-antisense microparticles were collected from the dispersions by centrifugation and supernatant decantation/aspiration. The collected microparticles were centrifugally washed repeatedly with methylene chloride to remove the non-ionic polymers, and lyophilized into dry powders.

Preparation Process 2:

In this process, the Ca-antisense microparticles were prepared as follows: Aliquots of non-ionic polymer solution A were prepared such that each made up $2/3^{rd}$ of the total volume of the final reaction mixture (including the non-ionic polymer solution, the salt solution, and the nucleic acid solution). Salt aliquots were prepared such that when mixed directly with the nucleic acid aliquots that they would have intermediate salt concentrations of 0.1M, 0.3M, 1M, 2M, 3M, and 4.18M. Salt aliquots and nucleic acid aliquots were pre-heated, combined to form intermediate mixtures and incubated for 30 minutes, all at about the same temperature (70° C.). Non-ionic polymer aliquots, also pre-heated, were combined with the intermediate mixtures to form the reaction mixtures and incubated for 30 minutes, all at about the same temperature (70° C.). The reaction mixtures were cooled to about −10° C. by exposing the reaction mixtures to a −10° C. cooling medium for 30 minutes. Ca-antisense microparticles were dispersed in all reaction mixtures as visualized with light microscopy.

Ca-antisense microparticles were collected from the dispersions using centrifugation and supernatant decantation/aspiration. The microparticles were centrifugally washed repeatedly with 1.5M $CaCl_2$ solution at 4° C., then centrifugally washed repeatedly with 0.2M $CaCl_2$ solution at 4° C. The washed Ca-antisense microparticles were then lyophilized into dry powders.

In an alternative washing process, the collected Ca-antisense microparticles were centrifugally washed repeatedly with 50% (w/v) PEG 3350 solution at 4° C. and lyophilized to remove water and volatile salts. These lyophilized preparations were then resuspended to be centrifugally washed repeatedly with methylene chloride/methanol mixture and subsequently washed with methylene chloride alone to remove PEG and PVP, and re-lyophilized to remove methylene chloride.

Results

Under otherwise identical conditions, the cooling rate of the Ca-antisense microparticles correlated with the average aerodynamic diameter of the microparticles (FIGS. 1A-1E and FIGS. 2A-B and FIG. 11), without affecting the aerodynamic diameter distribution of the microparticles (in the range of 0.34 to 0.43). As can be seen from FIGS. 1A-1E and FIGS. 2A-B, the diameter of the Ca-antisense microparticles decreased with increasing cooling rate. However, the average diameter distribution of the overall population of Ca-microparticles in any given reaction mixture remained substantially uniform.

The aerodynamic diameter distribution was measured by the ratio of aerodynamic diameter distribution range to the average aerodynamic diameter of the microparticles, where the aerodynamic diameter distribution range is the difference between the aerodynamic diameter that corresponds to $95^{th}$ percentile of the particles (i.e., 95% of the particles are of this aerodynamic diameter or smaller) and the aerodynamic diameter that corresponds to $10^{th}$ percentile of the particles (i.e., 10% of the particles are of this aerodynamic diameter or smaller). For Ca-antisense microparticles, the aerodynamic diameter distribution was less than 0.7, typically in the range of 0.3 to 0.6. Exemplary aerodynamic diameter distributions ($10^{th}$ percentile 1.836 micron, average 2.294 micron, $95^{th}$ percentile 2.954 micron) and next-generation impactor (NGI) characterization patterns (MMAD being 2.6 microns to 2.9 microns, GSD being 1.5, emitted dose being 73% to 77%, FPF (<8 micron) being 78% to 82% or greater of the emitted dose) of Ca-antisense microparticles are illustrated in FIGS. 3A-B and 4A-B, respectively.

Figure 5A:
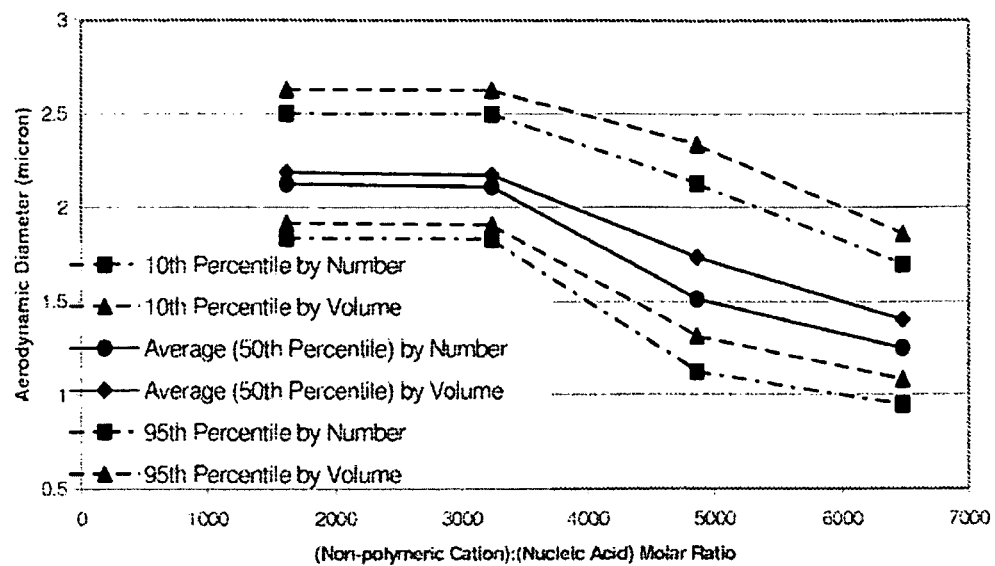
FIGS. 5A-B show a consistent correlation between the aerodynamic diameter cut-off values of the nucleic acid microparticles at different percentiles and the molar ratio of the non-polymeric cation to the nucleic acid in the reaction mixture prior to the formation of the nucleic acid microparticles. The curves of FIG. 5B are identical to the middle solid curves of FIG. 5A.
Figure 5B:
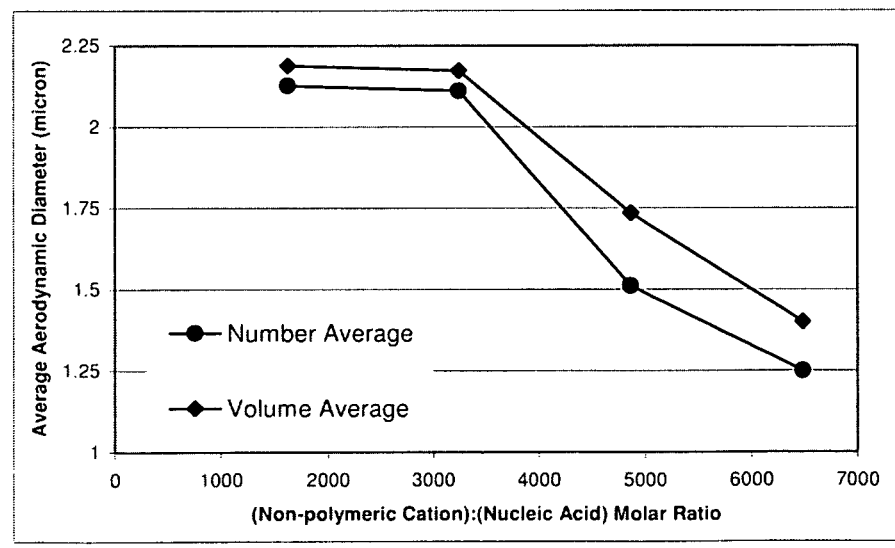
Figure 6:
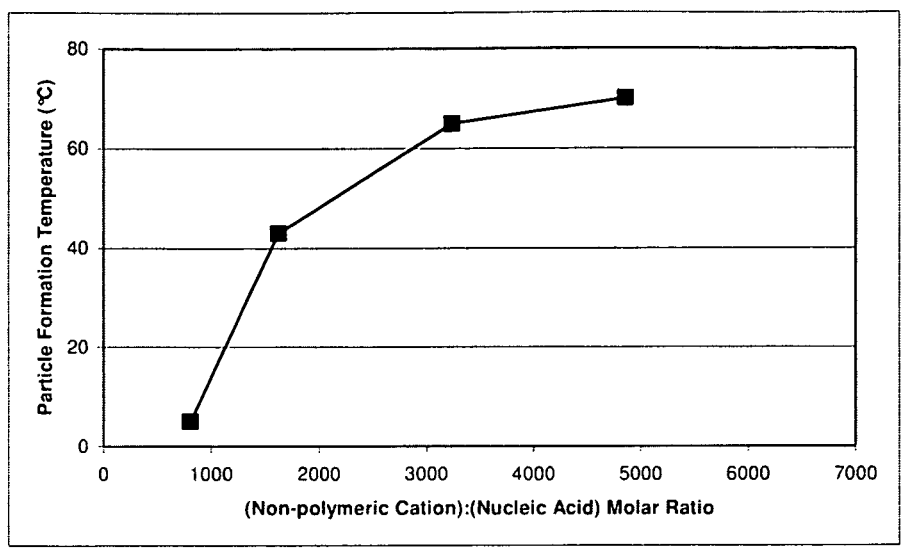
FIG. 6 shows a positive correlation between the temperature at which the nucleic acid microparticles form during the cooling process and the molar ratio of the non-polymeric cation to the nucleic acid in the reaction mixture prior to the formation of the nucleic acid microparticles.

Under otherwise identical conditions, the molar ratio of the non-polymeric cation to the nucleic acid in the reaction mixture correlated with the aerodynamic diameter of the microparticles produced in the given reaction mixture (FIGS. 5A-B), as well as with the temperature at which the microparticles formed during the cooling process (FIG. 6). These data corresponded to a cooling rate of 1° C./min. More particularly, as can be seen from FIGS. 5A-B, the aerodynamic diameter of the microparticles-decreased with increasing molar ratio of non-polymeric cation to nucleic acid. As can be seen in FIG. 6, the temperature at which particles formed increased with increasing molar ratio of non-polymeric cation to nucleic acid.

Ca-antisense microparticles had an average aerodynamic diameter of 1-3 micron. Typically, at least 85% of the microparticles in any given reaction were distributed over a narrow range of about 0.8-4 microns. The moisture content of the Ca-antisense microparticles ranged between 3% to 7%, and more specifically a moisture content of between 3.6% to 6.1%. Finally, the non-polymeric cation content of the Ca-antisense microparticles ranged from 4% or greater, and typically, the non-polymeric cation content of ranged from 4.1% to 4.3% of the microparticle.

Figure 12:
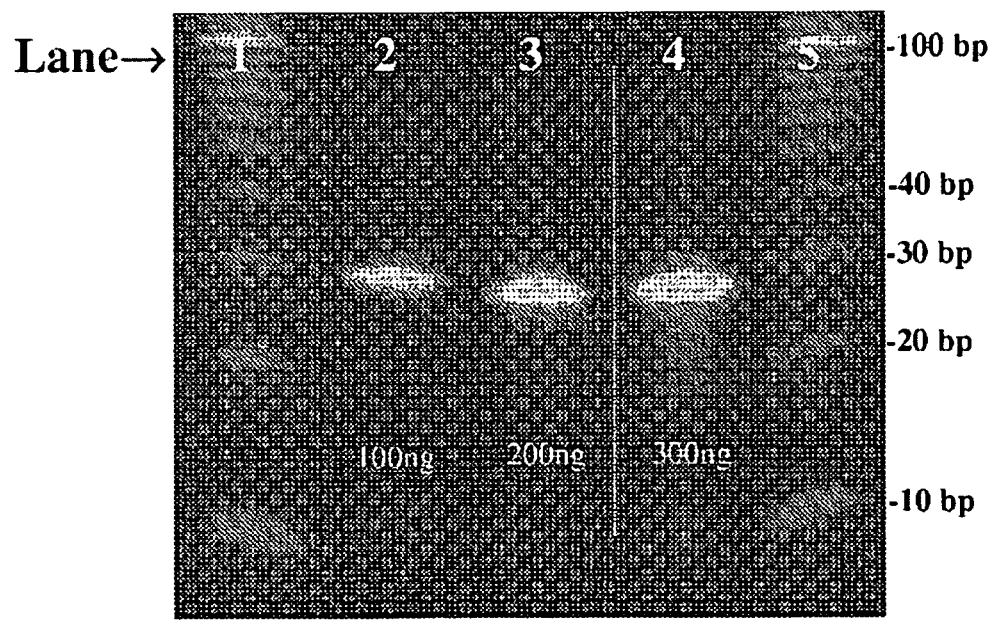
FIG. 12 shows that the nucleic acid (e.g., antisense oligonucleotide) is not degraded through the microparticle formation process. Lanes 1 and 5 are 10-bp DNA ladders for reference. Lane 3 is the de-formulation mixture of the microparticles corresponding to FIG. 11, while lanes 2 and 4 are the same nucleic acid molecule as controls.

As shown in FIG. 12, the process of nucleic acid microparticle formation does not degrade the nucleic acids of Example 2.

Example 3

Exemplary Microparticles of Antisense Oligonucleotides Prepared with $Zn^{2+}$ as a Cation In this process, a series of seven reaction mixtures was prepared in which each reaction mixture contained the non-ionic polymer solution, the salt solution and the nucleic acid solution. Briefly, aliquots of non-ionic polymer solution A were dispensed into a vessel such that two-thirds of each final reaction mixture would contain solution A. Aliquots of antisense nucleic acid solution were prepared such that when these aliquots of nucleic acid solution were added to the final reaction mixture, the concentration of the antisense nucleic acid in each final reaction mixture would be 0.206 mM.

A 4M $ZnCl_2$ stock solution (pH 4) was used to prepare aliquots of the salt solution through dilution with water such that the Zn concentrations in the initial salt with nucleic acid mixtures when the aliquots were added to the reaction mixtures would be 0.1M, 0.33M, 1M, 2M, and 3M, respectively.

The salt aliquots and nucleic acid aliquots were pre-heated and then combined to form intermediate mixtures. These intermediate mixtures were incubated for 30 minutes, all at about the same temperature (70° C.). All intermediate mixtures became turbid upon mixing, and the turbidity was visibly seen to increase with increasing Zn concentration. Non-ionic polymer aliquots that had also been pre-heated, were combined with the intermediate mixtures to form the final combined reaction mixtures. The final combined reaction mixtures were incubated for 30 minutes, all at about the same temperature (70° C.). All the final reaction mixtures remained turbid upon mixing, and the turbidity as seen through visual inspection increased with increasing Zn concentration. The Zn-antisense microparticles prepared according to this process were dispersed throughout all the reaction mixtures as visualized with light microscopy. The reaction mixtures were cooled to about −10° C. by exposing the reaction mixtures to a −10° C. cooling medium for 30 minutes. Upon cooling, the Zn-antisense microparticles were re-inspected via light microscopy and were seen to be dispersed in all the reaction mixtures.

The Zn-antisense microparticles were collected from the dispersions using centrifugation and supernatant decantation/aspiration. The collected Zn-antisense microparticles were centrifugally washed repeatedly with 1.5M $ZnCl_2$ solution at 4° C. The washed Zn-antisense microparticles were then centrifugally washed repeatedly with 0.2M $ZnCl_2$ solution at 4° C., and finally lyophilized into dry powders.

In an alternative washing procedure, the collected Zn-antisense microparticles were centrifugally washed repeatedly with 50% (w/v) PEG 3350 solution at 4° C., and lyophilized to remove water and volatile salts. The lyophilized Zn-antisense microparticles were then resuspended and centrifugally washed repeatedly with methylene chloride to remove PEG 3350, prior to being re-lyophilized in order to remove methylene chloride.

The Zn-antisense microparticles prepared from the reaction mixture containing 0.33M Zn had an average particle size of 400 nm. The zeta potential of these Zn-antisense microparticles was −17 mV (in 1 mM KCl, pH=7.1, PALS Zeta Potential Analyzer ver. 3.29, Brookhaven Instruments Corp.). The antisense nucleic acid loading in these Zn-antisense microparticles was 48% (by weight of the microparticles, as determined using gel electrophoresis and quantitation).

Example 4

Exemplary Microparticles of Antisense Oligonucleotides Prepared with $Mg^{2+}$ as the Cation The same was used for forming the Mg-antisense microparticles described in Example 3 process for forming the Zn-antisense microparticles except that the stock Zn salt solution was substituted with a $MgCl_2$ stock solution (4.09M, pH 4.5) and Mg final concentration in reaction mixtures being 0.033M, 0.1M, 0.33M, 0.67M, and 1M, respectively. Upon mixing of the salt solution and the nucleic acid solution, the intermediate reaction mixture that contained 0.033M Mg appeared visibly clear, while all other intermediate mixtures became turbid upon mixing. The turbidity of the intermediate reaction mixtures increased with increasing Mg concentration. When the inter mediate mixtures were mixed with the non-ionic polymer solution A, the reaction mixture that contained 0.033M Mg remained clear, the reaction mixtures that contained 0.1M and 0.33M Mg remained turbid, the reaction mixture containing 0.67M Mg turned clear, and the reaction mixture containing 1M Mg precipitated agglomerates that settled in the bottom of the reaction vessel. Incubation of the reaction mixtures for 30-minutes at 70° C. turned all reaction mixtures into homogeneous, single-phase solutions. Upon cooling, all reaction mixtures became turbid, with the reaction mixtures containing 0.67M and 1M Mg having compositions of sufficient density that the microparticles settled in the reaction mixture upon cooling. Mg-antisense microparticles were dispersed in all reaction mixtures as visualized with light microscopy.

The Mg-antisense microparticles were collected from the dispersions using centrifugation and supernatant decantation/aspiration and centrifugally washed repeatedly with 1.5M $MgCl_2$ solution at 4° C. The washed, pellets of Mg-antisense microparticles were then centrifugally re-washed repeatedly with 0.2M $MgCl_2$ solution at 4° C., and finally lyophilized into dry powders.

In an alternative washing procedure, the collected Mg-antisense microparticles were centrifugally washed repeatedly with 50% (w/v) PEG 3350 solution at 4° C., and lyophilized to remove water and volatile salts. The lyophilized Mg-antisense microparticles were then centrifugally washed repeatedly with methylene chloride to remove PEG 3350, and re-lyophilized to remove methylene chloride.

Example 5

Exemplary Microparticles of Antisense Oligonucleotides Prepared with $Na^+$ as the Cation To prepare Na-antisense microparticles, substantially the same process as described above in example 3 for forming the Zn-antisense microparticles was followed except that the Zn stock salt solution was substituted by NaCl stock solution (5.3M, pH 6.7). Six reaction mixtures were used in which the final sodium concentration in reaction mixtures was 0.033M, 0.1M, 0.33M, 0.67M, 1M, and 1.47M, respectively. All intermediate mixtures were visibly clear except for the reaction mixture that contained 1.47M Na, which was turbid. Upon mixing, all reaction mixtures became turbid. Incubation of the reaction mixtures for 30-minutes at 70° C. turned all reaction mixtures into clear homogeneous, single-phase solutions). Upon cooling, the reaction mixtures containing 0.033M, 0.1M, and 0.33M Na remained clear, the reaction mixtures containing 0.67M and 1M Na became turbid, and the reaction mixture containing 1.47M Na remained turbid. The reaction mixtures containing 0.67M and 1M Na became visibly clear again when heated to ambient temperature, but became turbid again upon cooling, demonstrating that the microparticles were reversibly formed and de-formed with cooling and heating, respectively.

Example 6

Exemplary Microparticles of siRNA Prepared using $Ca^{2+}$ as a Cation

Process 1 described in Example 2 above for forming the Ca-antisense microparticles was used to prepare Ca-siRNA microparticles except that the nucleic acid solution from Example 2 was substituted by siRNA solutions in the present example such that the concentration of siRNA in each reaction mixture was 0.151 mM. Seven separate reaction mixtures were set up containing Ca concentrations of 0.033M, 0.1M, 0.17M, 0.5M, 0.67M, 0.74M, and 1M, respectively. Examples of Ca-siRNA microparticles were prepared using non-ionic polymer solution A, as well as using non-ionic polymer solutions B and C. Reaction preheat temperatures were varied. Reactions were set up with preheat temperatures of 58° C., 60° C., and 70° C. Upon mixing the nucleic acid solution and the non-ionic polymer/salt solution at the pre-heat temperature, all reaction mixtures became turbid and remained turbid at the end of the 5-minute incubation period. The turbidity of the reaction mixtures increased with increasing Ca concentration in the reaction mixture. Following cooling and incubation, Ca-siRNA microparticles collected from the dispersions (using centrifugation and supernatant decantation/aspiration) were centrifugally washed repeatedly with appropriate washing medium at 4° C., and lyophilized into dry powders.

Example 7

Exemplary Microparticles of siRNA Prepared using $Mg^{2+}$ as a Cation

The process described in Example 6 above for forming the Ca-siRNA microparticles was used to prepare Mg-siRNA microparticles except that the, salt stock solution in Example 6 was substituted in the present example with $MgCl_2$ stock solution (5M, pH 5.6). Two reaction mixtures were set up containing Mg concentrations in the reaction mixtures being 0.78M and 1.15M, respectively. Upon mixing the nucleic acid solution and the non-ionic polymer/salt solution at the pre-heat temperature (70° C.), all reaction mixtures were visibly clear (i.e., the reaction mixtures were homogeneous, single-phase solutions) and remained clear at the end of the 5-minute incubation period. Upon cooling and incubation, Mg-siRNA microparticles collected from the dispersions (using centrifugation and supernatant decantation/aspiration) were centrifugally washed repeatedly with appropriate washing medium at 4° C., and lyophilized into dry powders. Mg-siRNA microparticles formed at 1.15M Mg concentration in the presence of non-ionic polymer solutions B and C.

Example 8

Mg-siRNA Microparticles

Figures 15, 16:
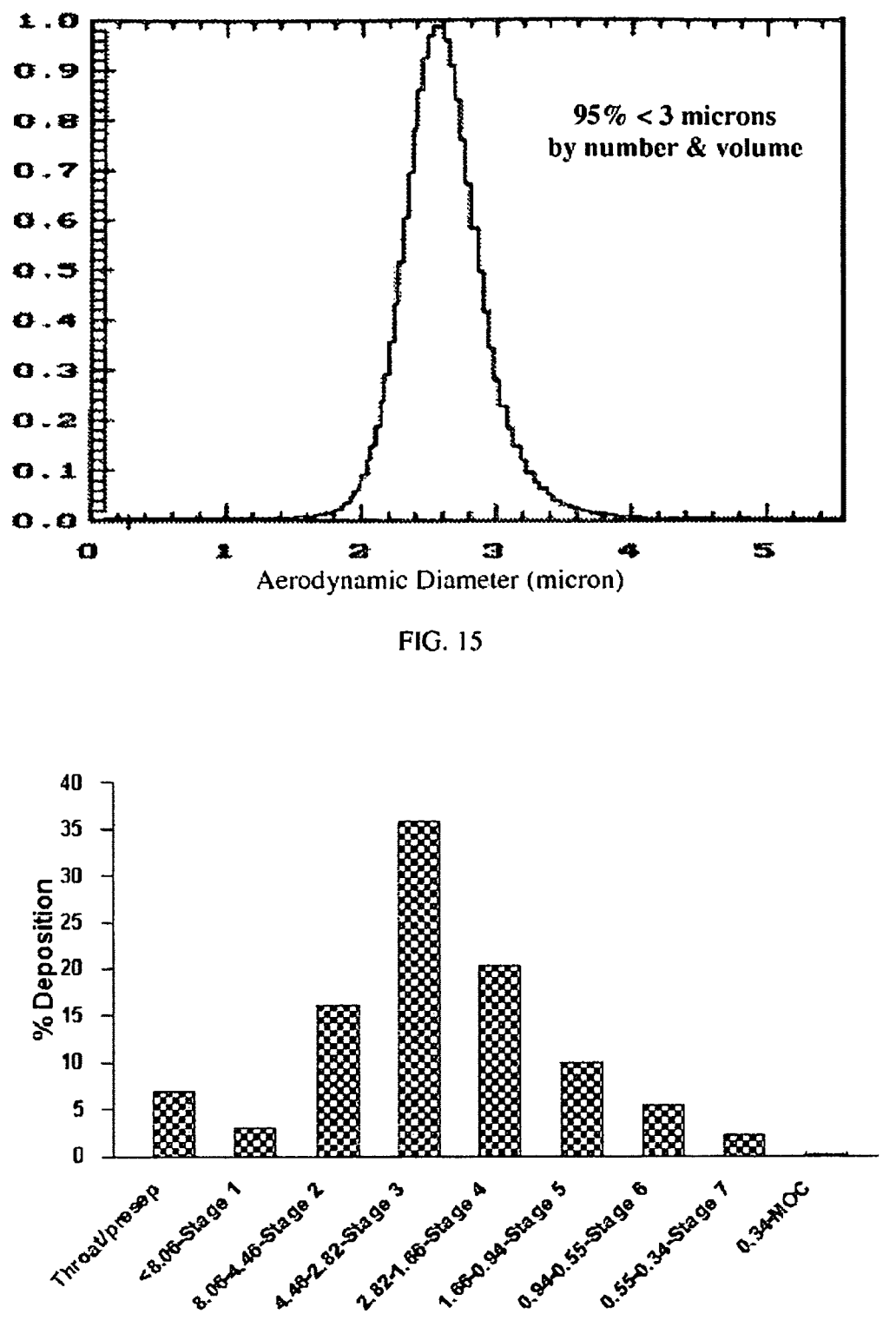

Mg-siRNA microparticles were prepared according to methods disclosed above with the formulations and reaction conditions listed in the following tables. All siRNAs were commercially available from Dharmacon. FIGS. 7A-B, 8A-B, 9A-B, 10A-B, and 13 are SEM images of these microparticles. As shown in FIG. 14, the process of nucleic acid microparticle formation does not degrade the nucleic acids of Example 8. As shown in FIGS. 15 and 16, the nucleic acid microparticles of Example 8 have the aerodynamic characteristics (e.g., 95% of the population less than 3 microns by number and volume, high FPF) suitable for pulmonary delivery.

Figure 7A:
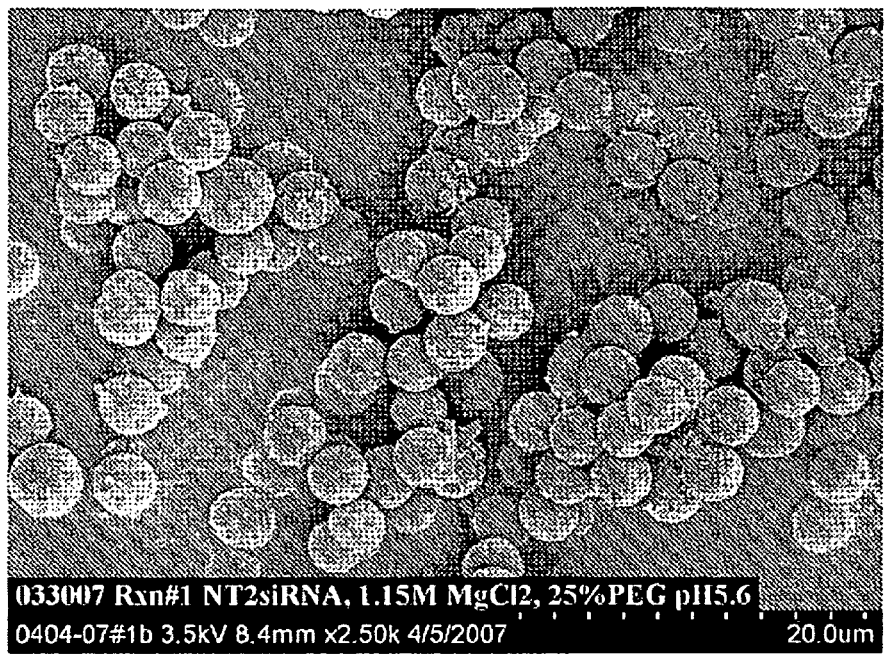
FIGS. 7A-B, 8A-B, 9A-B, and 10A-B show the nucleic acid microparticles formed from the various labeled and unlabeled siRNA molecules according to Example 8.
Figure 8A:
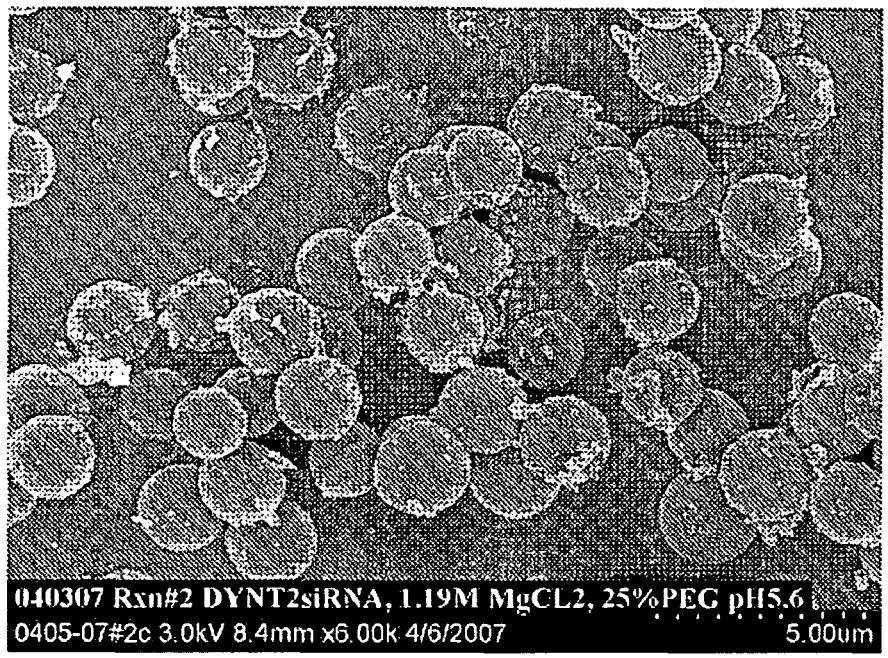
Figure 9A:
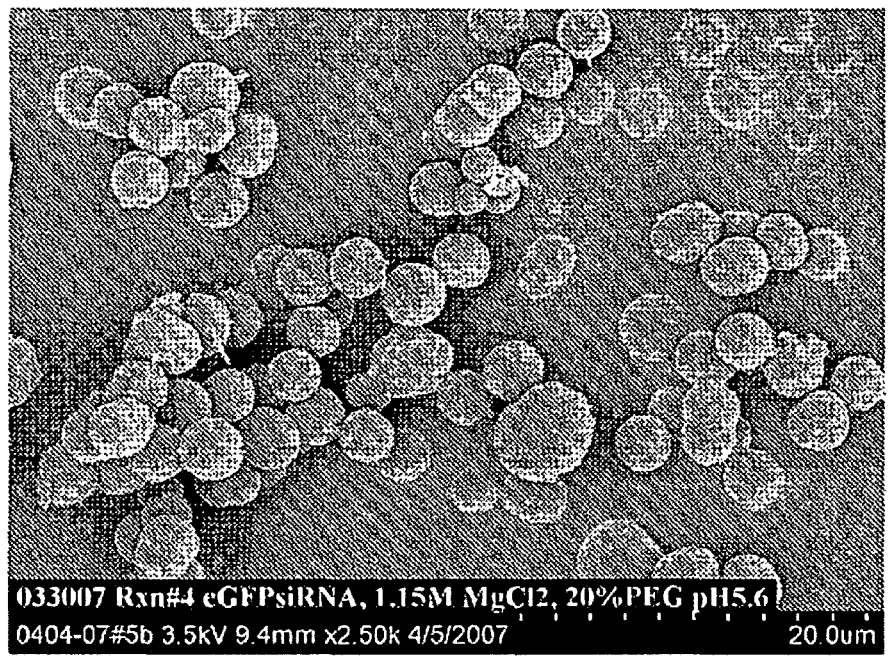
Figure 10A:
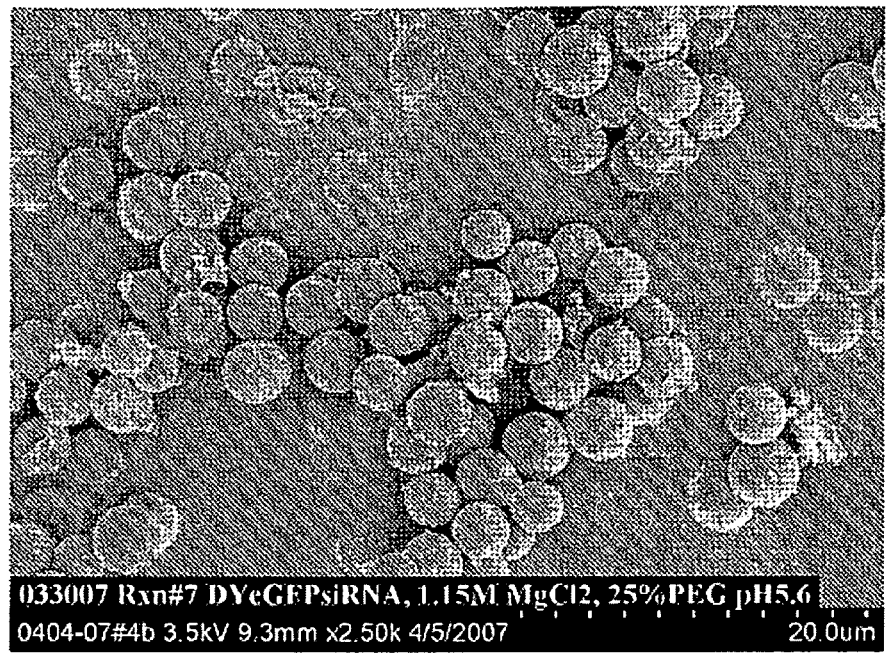

| Parameters | FIG. 7A | FIG. 8A | FIG. 9A | FIG. 10A |
|---|---|---|---|---|
| Nucleic acid (MW) | NT-2 siRNA (13,438) | DY547-labeled NT-2 siRNA (13,851) | eGFP siRNA (13,526) | DY547-labeled eGFP siRNA (13,939) |
| Nucleic acid final concentration | 0.149 mM | 0.144 mM | 0.146 mM | 0.140 mM |
| PEG 3350 final concentration [Stock concentration] | 16.67% (w/v) [25% (w/v)] | 16.67% (w/v) [25% (w/v)] | 13.33% (w/v) [20% (w/v)] | 16.67% (w/v) [25% (w/v)] |
| $Mg^{2+}$ final concentration | 1.15 M | 1.19 M | 1.15 M | 1.15 M |
| Ph | 5.6 | 5.6 | 5.6 | 5.6 |
| Pre-heat temperature | 65° C. | 65° C. | 65° C. | 65° C. |
| Cooling rate | 0.1° C./minute | 0.5° C./minute | 0.1° C./minute | 0.1° C./minute |

Figure 7B:
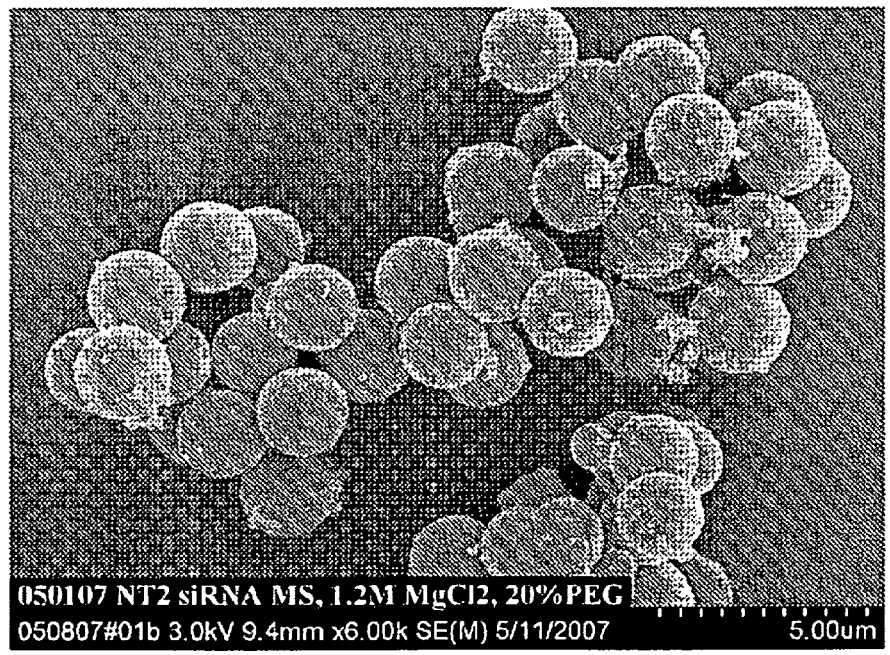
Figure 8B:
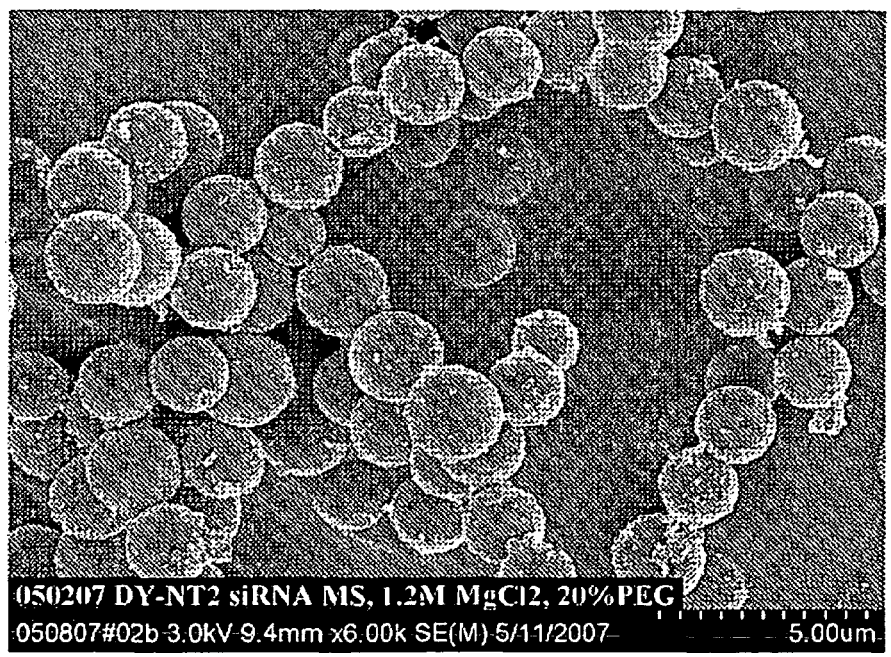
Figure 9B:
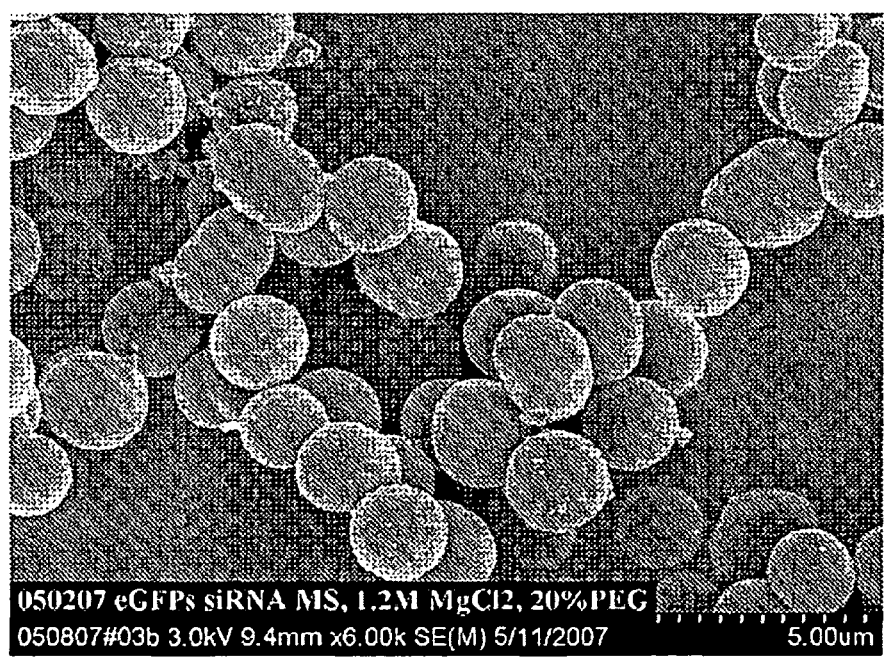
Figure 10B:
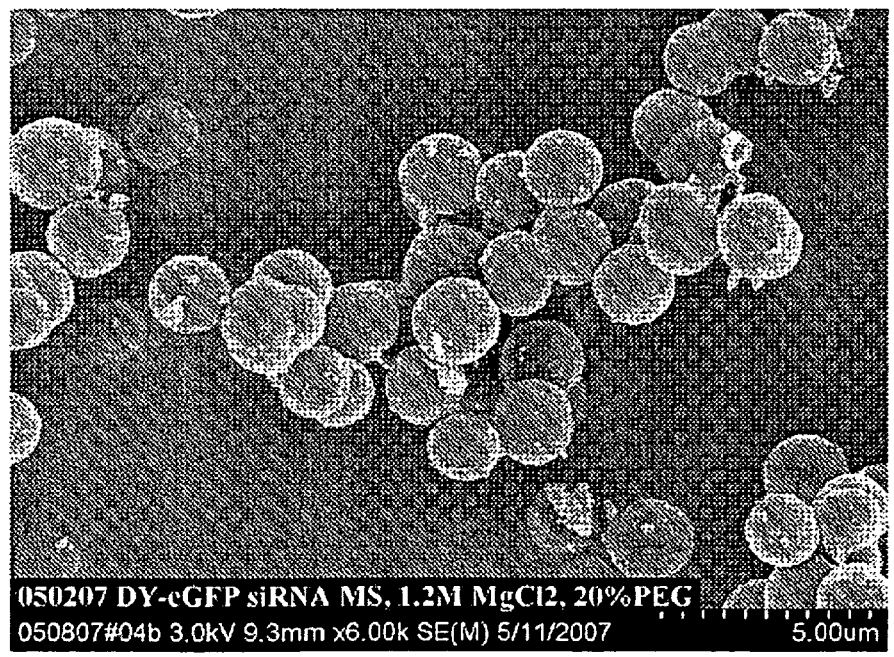
Figure 11:
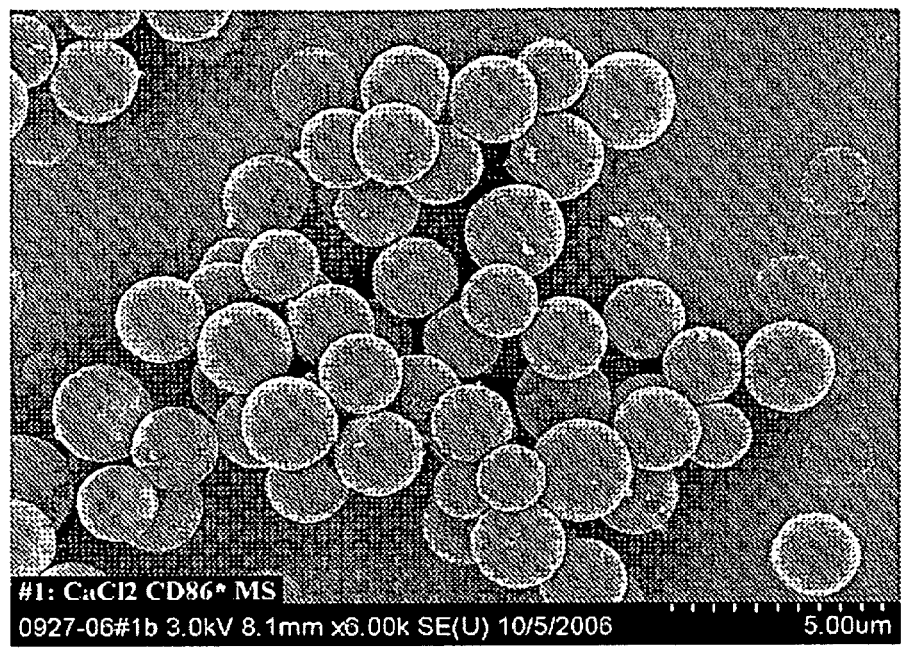
FIG. 11 shows antisense oligonucleotide microparticles formed according to Example 2.
Figure 13:
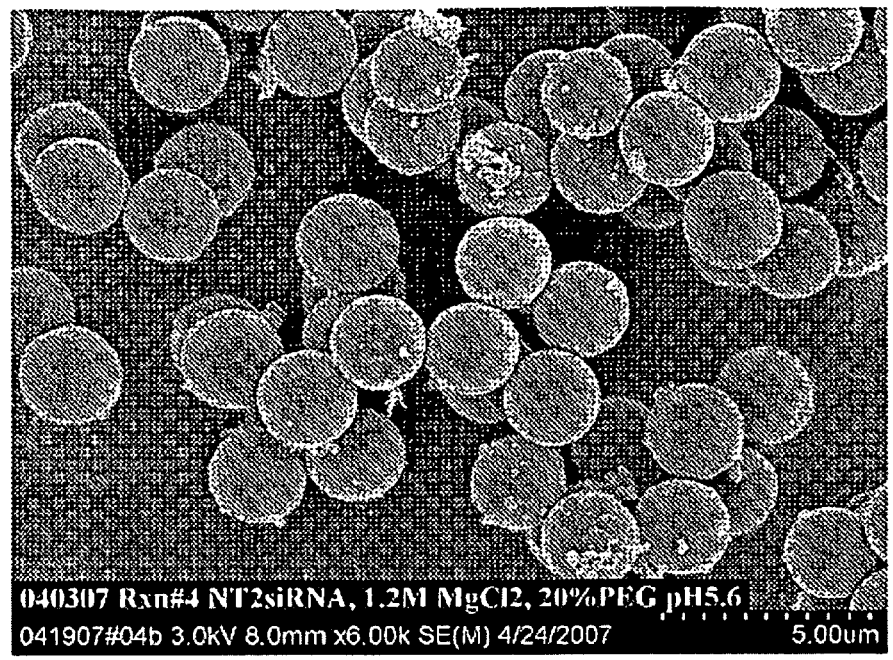
FIG. 13 shows siRNA microparticles formed according to Example 8.
Figure 14:
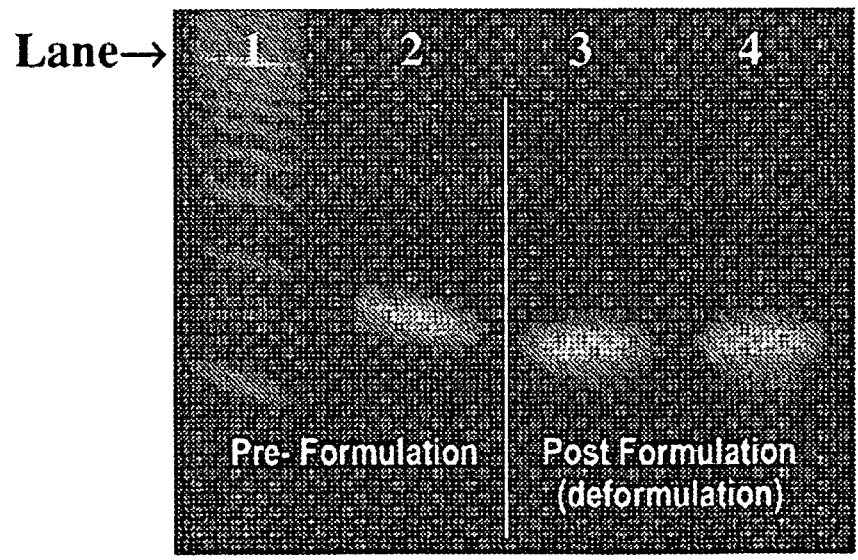
FIG. 14 shows that the nucleic acid (e.g., siRNA) is not degraded through the microparticle formation process. Lane 1 is 10-bp DNA ladders for reference. Lanes 3 and 4 are de-formulation mixtures of two different microparticle formulations (same nucleic acid molecule) according to Example 8, while lane 2 is the same nucleic acid molecule as control.

| Parameters | FIG. 7B | FIG. 8B | FIG. 9B | FIG. 10B | FIG. 13 |
|---|---|---|---|---|---|
| Nucleic acid | NT-2 siRNA | DY547-NT-2 siRNA | eGFP siRNA | DY547-eGFP siRNA | NT-2 siRNA |
| Nucleic acid final concentration | 0.15 mM | 0.15 mM | 0.15 mM | 0.15 mM | 0.15 mM |
| Polymer final concentration | 20% (w/v) | 20% (w/v) | 20% (w/v) | 20% (w/v) | 20% (w/v) |

| Parameters | FIG. 7B | FIG. 8B | FIG. 9B | FIG. 10B | FIG. 13 |
|---|---|---|---|---|---|
| [Stock concentration] | [50% (w/v)] | [50% (w/v)] | [50% (w/v)] | [50% (w/v)] | [50% (w/v)] |
| $Mg^{2+}$ final concentration | 1.228 M | 1.228 M | 1.228 M | 1.228 M | 1.228 M |
| pH | 5.6 | 5.6 | 5.6 | 5.6 | 5.6 |
| Pre-heat temperature | 65° C. | 65° C. | 65° C. | 65° C. | 65° C. |
| Cooling rate | 0.5° C./min | 0.5° C./min | 0.5° C./min | 0.5° C./min | 0.5° C./min |

Example 9

Mg-siRNA Microparticles

Mg-siRNA microparticles were prepared according to methods disclosed above, using NT-2 siRNA as the nucleic acid, non-ionic polymer solution D as the stock solution, pH at 5.6, pre-heat temperature of 65° C., cooling rate of 0.5° C./minute, cooling end temperature 4° C., and different polymer final concentrations and different cation final concentrations as listed in the following table. All reactions resulted in the formation of spherical nucleic acid microparticles.

| Reaction # | Cation final concentration | Polymer final concentration | Molar Ratio [Cation]:[Nucleic acid] | Particle Forming Temperature |
|---|---|---|---|---|
| 1 | 1.228 M | 16.7% (w/v) | 8251:1 | 5° C. |
| 2 | 1.8 M | 16.7% (w/v) | 12094:1 | 5° C. |
| 3 | 2.2 M | 16.7% (w/v) | 14782:1 | 65° C. |
| 4 | 1.228 M | 20.0% (w/v) | 8251:1 | 21° C. |
| 5 | 1.8 M | 20.0% (w/v) | 12094:1 | 22° C. |
| 6 | 2.2 M | 20.0% (w/v) | 14782:1 | 65° C. |
| 7 | 1.228 M | 23.7% (w/v) | 8251:1 | 28° C. |
| 8 | 1.8 M | 23.7% (w/v) | 12094:1 | 65° C. |
| 9 | 2.2 M | 23.7% (w/v) | 14782:1 | 65° C. |

Example 10

Production of Microspheres with Cholesterol Modified siRNA

Figure 17:
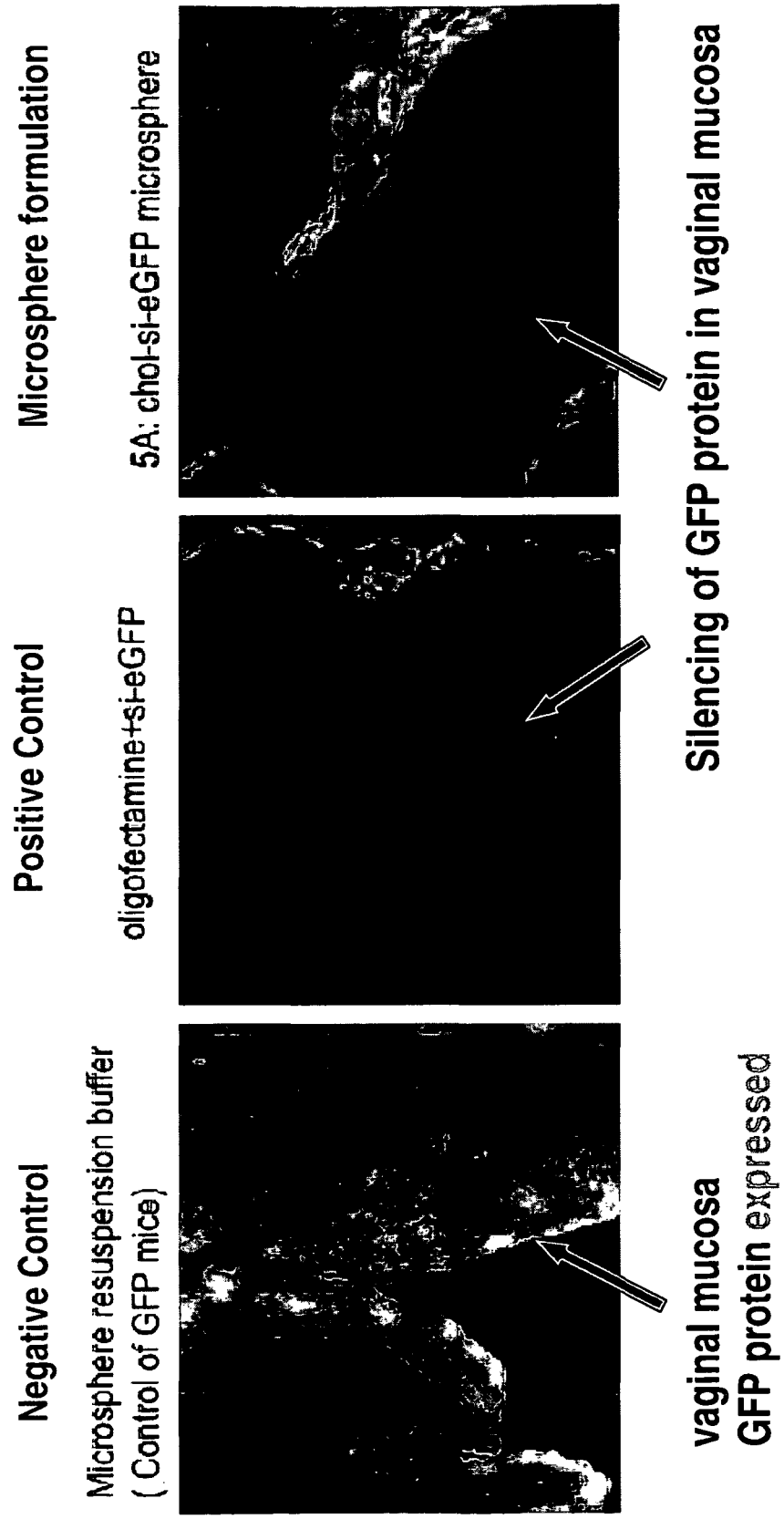
FIG. 17 depicts a cholesterol modified siRNA specific for enhanced green fluorescent protein (eGFP).
Figure 18:
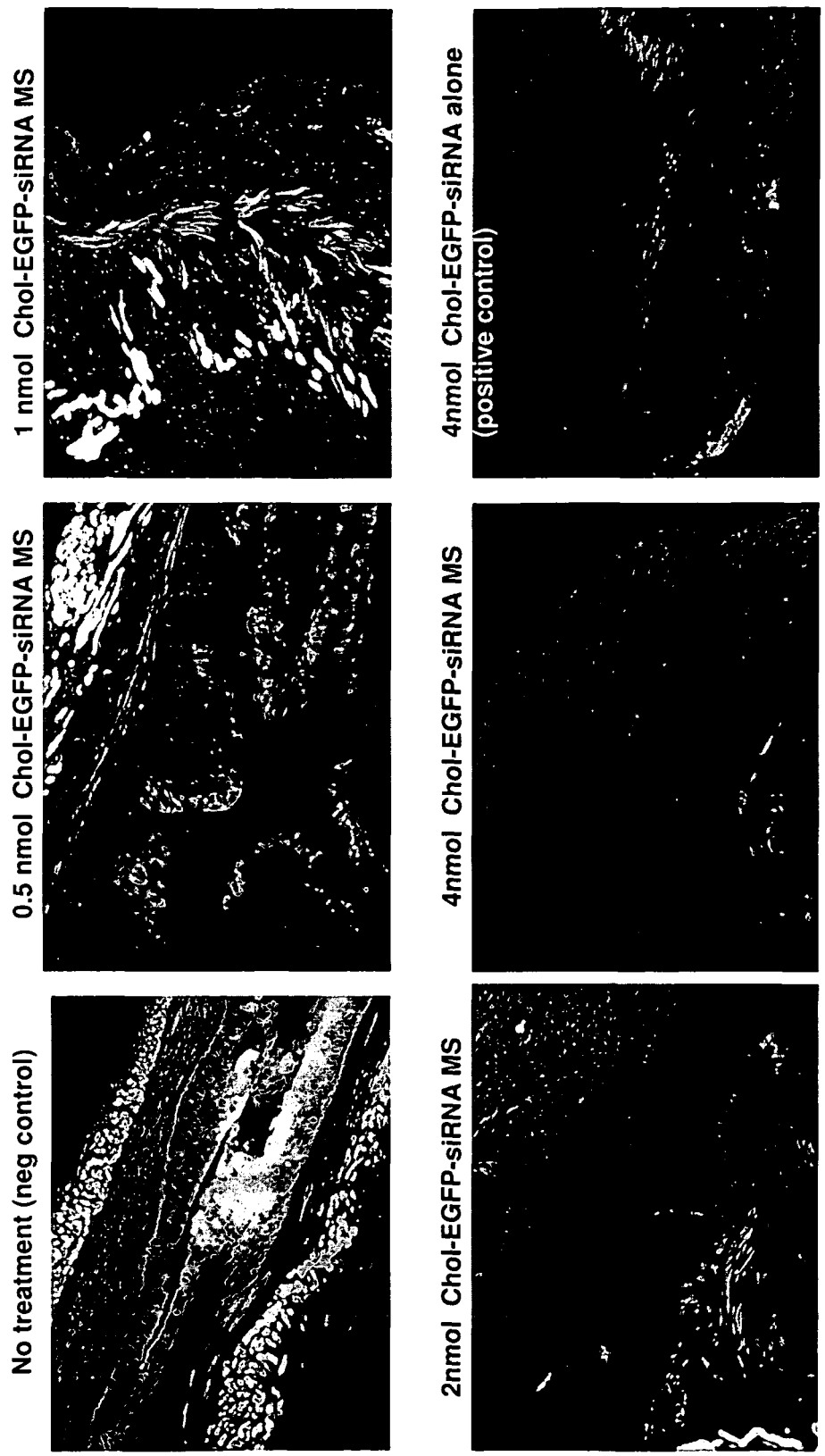
FIG. 18 shows the knock down effect of cholesterol modified siRNA in microsphere form on eGFP expression in vaginal mucosa, compared to microsphere buffer and siRNA for eGFP with Oligofectamine.

An nuclease-free aqueous solution (the water, obtained from Ambion, Cat#9930, is deionized and nuclease free, and additionally autoclaved and 0.2 μm sterile filtered) containing cholesterol-conjugated enhanced green fluorescent protein (eGFP, Dharmacon/Thermofisher) siRNA as shown in FIG. 17 dissolved therein was heated to 37° C. A buffered polymer/cation solution containing an aqueous-soluble polyethylene glycol 3500 (PEG 3350, Spectrum, Cat# P0125; solution consisting of 46% PEG, buffered with 0.245 M NaOAc, in nuclease free water pH 5.6, and diluted in the final formulation to 12.5% PEG and 67 mM NaOAc), an aqueous-soluble salt of a $MgCl_2$ (100 mM $MgCl_2$ solution (pH 5.6) in 0.2 μm filtered water), and a buffer sodium acetate (Spectrum, Cat# S0104) all dissolved therein was heated to 65° C. At 65° C., an aliquot of the siRNA solution was admixed to an aliquot of the polymer/cation solution to final concentrations of the cholesterol-modified siRNA, the polymer, the cation, and the buffer of 0.142 mM, 12.5% (w/v), 25 mM, and 67 mM, respectively. The molar ratio between the polyvalent cation and the cholesterol-modified siRNA in the reaction mixture was 176:1. The reaction mixture was incubated at 65° C., during which the mixture became clear, after which the clear mixture was cooled at 0.8° C./minute to 0° C., during which time microspheres of the cholesterol-modified siRNA formed turning the clear mixture into milky white. The microspheres were collected through centrifugation at 0° C., washed three times with a chilled 0° C., binary solution of 50% 2-methyl-2-propanol and 50% water (w/v), re-suspended in the binary solution, frozen and lyophilized into a dry powder.

The resulting microspheres were solid, spherical, and monodispersed in particle size.

| Rxn # | Nucleic Acid | Molecular Weight (g/mole) | Polymer | % Polymer In Final Vol | Cation or Salt | Starting [Salt] (M) | Final [Salt] (M) | Salt Vol. (ul) |
|---|---|---|---|---|---|---|---|---|
| 1 | CHOLeGFP siRNA | 14070.1 | PEG | 12.5 | $MgCl_2$ | 0.10 | 0.0250 | 187.5 |

| Vol. Water (ul) | Start [siRNA] (mg/ml) | Final [siRNA] (mM) | Vol. siRNA (ul) | Molar ratio Salt:siRNA | Vol. Polymer Sol'n (ul) | Total Vol. (ul) | Starting % Polymer |
|---|---|---|---|---|---|---|---|
| 233.5 | 11.98 | 0.142 | 125.2 | 176:1 | 203.8 | 750 | 46 |

| Aerosizer Data Sample Information | 10% Under (um) | 50% Under (um) | 95% Under (um) |
|---|---|---|---|
| 061907 MS Chol.eGFP siRNA, 25 mM $MgCl_2$ 12.5% PEG | 3.027 | 3.543 | 4.443 |

Example 11

Use of Cholesterol Modified siRNA in Standard Microsphere Formulation for Pulmonary Delivery An aqueous solution containing dissolved cholesterol-modified eGFP siRNA as shown FIG. 17 was heated to 37° C. A solution containing an aqueous-soluble PEG 3350 buffered with sodium acetate was mixed with $MgCl_2$ solution as described above and heated to 65° C. At 65° C., aliquots of the siRNA solution were added to aliquots of the polymer/cation solution to final concentrations of the cholesterol-modified siRNA, the polymer, the cation, and the buffer of 0.142 mM, 16.7% or 20% (w/v), 1.173 M, and 67 mM, respectively. The molar ratio between the polyvalent cation and the cholesterol-modified siRNA in the reaction mixtures was 8251:1. At this cation concentration, the reaction immediately became milky white, and were incubated at 65° C. for 5 minutes, during which the mixtures stayed milky white. The mixtures were cooled at 0.5° C./minute to 0° C., the mixtures remained milky white. The microspheres were collected through centrifugation, washed three times with a binary solution of 50% 2-methyl-2-propanol and 50% water (w/v), re-suspended in the binary solution, frozen, and lyophilized into a dry powder.

The resulting microspheres were solid, spherical, polydispersed in particle size and mixed with non-spherical microparticles, as visualized with light microscopy and scanning electron microscopy.

Example 12

Microsphere Formulations with Lowered Cation Concentration to Controlled Phase Separation An aqueous solution containing dissolved cholesterol-modified eGFP siRNA depicted in FIG. 17 was heated to 37° C. PEG3500 polymer solutions as described above were mixed with a number of $MgCl_2$ solutions over a range of concentrations and thereafter heated to 65° C. At 65° C., aliquots of the siRNA solution were added to aliquots of the polymer/cation solutions to final concentrations of the cholesterol-modified siRNA, the polymer, the cation, and the buffer were 0.142 mM, 16.7% (w/v), cation range 1.173M to 0M (1.173 M, 587 mM, 293 mM, 147 mM, 73 mM, 25 mM, and 0 mM), and 67 mM, respectively. Final molar ratios of the polyvalent cation to the cholesterol-modified siRNA in the individual reaction mixtures were 8251:1, 4126:1, 2061:1, 1031:1, 516:1, 176:1, and 0:1 respectively. All of the mixtures, except the 0 mM cation solution which did not form a precipitate, immediately became milky white, and all were incubated at 65° C. for approximately 5 minutes during which the mixtures stayed milky white. All mixtures were then cooled to 0° C., and all but the 0 mM cation mixture remained milky white. Microspheres formed in each in these processes which become milky white, but formation was not via a CPS-like reaction. Thus, it was determined that under these conditions, the cation concentration needed to be below 25 mM for a CPS-like reaction.

Example 13

Additional Microsphere Formulations with Lowered Cation Concentration to Controlled Phase Separation An aqueous solution of a cholesterol-modified eGFP siRNA depicted in FIG. 17 dissolved therein was heated to 37° C. PEG3500 polymer solutions buffered with sodium acetate were mixed with various $MgCl_2$ solutions over a range of concentrations and heated to 65° C. At 65° C., aliquots of the siRNA solution were added to the polymer/cation solutions to final concentrations of the cholesterol-modified siRNA, the polymer, the cation, and the buffer of 0.142 mM, 16.7% or 20% (w/v), cation range 15 mM to 10 mM (10 mM, 12.5 mM, 15 mM or 12.5 mM with the single 20% PEG formulation), and 67 mM, respectively. Molar ratios of the polyvalent cation and the cholesterol-modified siRNA in the various mixtures were 70:1, 80:1, 106:1, or 80:1 respectively. The reaction mixtures were incubated at 65° C. for 10 minutes, during which the 70:1 and 80:1 ratio reactions remained clear, the 106:1 ratio reaction was slightly hazy and the 80:1 ratio reaction was hazy. The mixtures were cooled at 0.5° C./minute to 0° C., during which time siRNA microspheres formed turning the mixtures milky white. The microspheres were collected through centrifugation, washed three times with a binary solution of 50% 2-methyl-2-propanol and 50% water (w/v), re-suspended in the binary solution, frozen, and lyophilized into a dry powder.

The resulting microspheres were solid, spherical, monodispersed in particle size and mixed with some non-spherical microparticles as visualized with light microscopy and scanning electron microscopy.

Example 14

Use of Calcium Cations in Microsphere Formulations

An aqueous solution containing dissolved cholesterol-modified eGFP siRNA depicted in FIG. 17 was heated to 37° C. Polymer solutions containing PEG 3350 or combination of PEG 3350 and PVP, each buffered with sodium acetate were mixed with $CaCl_2$ solutions over a range of concentrations and heated to 65° C. At 65° C., aliquots of the siRNA solution were mixed with the polymer/cation solutions. Conditions that yielded CPS-like reactions were those wherein the concentrations of the cholesterol-modified siRNA was 0.142 mM, the polymer was 16.7% or 20% PEG (w/v) or combination of 8.3% each of PEG and PVP, the cation was 10 mM or 7.5 mM or 25 mM, and the buffer was 67 mM. Molar ratios of polyvalent cation and cholesterol-modified siRNA in the reaction mixtures were 70:1 or 50:1 or 176:1 respectively. All three reactions remained clear during incubation at 65° C. for approximately five minutes as determined visually in each 50 ul volume. Each mixture was then cooled to 0° C., and during the cooling process microspheres formed apparently by controlled phase separation like reaction.

Example 15

Additional Microsphere Formulations with Magnesium to Provide Controlled Phase Separation and Less Agglomeration In view of the results obtained above, small scale screening experiments were carried out in order to lower the polymer content of the $MgCl_2$ formulation to determine conditions that would yield a CPS-like reaction and provide microspheres that could be used in an Aerosizer assay with less agglomeration.

An aqueous solution containing dissolved cholesterol-modified eGFP siRNA depicted in FIG. 17 was heated to 37° C. PEG3500 polymer solutions buffered with sodium acetate were mixed to two solutions containing different amounts of $MgCl_2$ and heated to 65° C. At 65° C., aliquots of the siRNA solution was mixed with aliquots of the polymer/cation solutions such that the final concentrations of the cholesterol-modified siRNA, the polymer, the cation, and the buffer were 0.142 mM, 12.5% (w/v), 20 mM or 25 mM, and 67 mM, respectively. Molar ratios of polyvalent cation to cholesterol-modified siRNA in the reaction mixtures were 141:1, or 176:1 respectively. The reaction mixtures were incubated at 65° C. for 10 minutes during which time the mixtures remained clear. The mixtures were then cooled to 0° C., during which microspheres of the cholesterol-modified siRNA formed, turning the mixtures milky white, by controlled phase separation like reaction.

Example 16

Scaled-Up Formulations for Microsphere Characterization

The results described above led to a scaled-up set of experiments to screen for formulations that would yield a CPS-like reaction to produce microspheres that could be characterized.

An aqueous solution of dissolved cholesterol-modified eGFP siRNA depicted in FIG. 17 was heated to 37° C. Polymer solutions containing an either PEG 3350 or a combination of PEG 3350 and PVP, all buffered with sodium acetate, were mixed with $MgCl_2$ or $CaCl_2$ cation solutions over a range of concentrations and heated to 65° C. At 65° C., aliquots of the siRNA solution were mixed with aliquots of the polymer/cation solutions to provide final concentrations of the cholesterol-modified siRNA at 0.142 mM, PEG at 12.5% (w/v), $MgCl_2$ at 20 mM or 25 mM, and buffer at 67 mM respectively. Molar ratios of $Mg^{++}$ cation and cholesterol-modified siRNA in these reaction mixtures were 141:1, or 176:1 respectively. For the PEG reactions with $CaCl_2$ the final concentrations were 0.142 mM siRNA, 16.7% or 20% (w/v) PEG, 10 mM or 7.5 mM $CaCl_2$, and 67 mM buffer, and final molar ratios of polyvalent cation to cholesterol-modified siRNA in the reaction mixtures were 70:1, or 53:1 respectively. For the PEG/PVP reaction with $CaCl_2$, the final concentrations were 0.142 mM siRNA, 8.3% each (w/v) PEG and PVP, 25 mM $CaCl_2$, and 67 mM buffer. Molar ratio between the polyvalent cation and the cholesterol-modified siRNA in this reaction mixture was 176:1. Each reaction mixtures was incubated at 65° C. for 5 minutes, during which time the mixtures with PEG and $MgCl_2$ remained clear and the mixtures with $CaCl_2$ became slightly hazy. After the 5 minute incubations, all mixtures were cooled at 0.75° C./minute to 0° C., during which time microspheres formed turning the clear or slightly hazy mixtures into milky white. The microspheres were collected through centrifugation, washed three times with a binary solution of 50% 2-methyl-2-propanol and 50% water, re-suspended in the binary solution, and lyophilized into a dry powder.

The resulting microspheres from the 12.5% PEG-25 mM $MgCl_2$, 16.7% PEG/10 mM $CaCl_2$, and 20% PEG/7.5 mM $CaCl_2$ reactions were solid, spherical, and monodispersed in particle size, the 8.3% PEG/PVP-25 mM $CaCl_2$ microspheres were solid and spherical, and had a slightly broader size distribution, and the 12.5% PEG/20 mM $MgCl_2$ reaction yielded smaller and slightly agglomerated microspheres. All resulting microspheres were visualized with light microscopy and scanning electron microscopy.

Example 17

Microsphere Formations Using Increasing Magnesium Cations at a Set Polymer Concentration In view of the results described above, experiment were designed to explore the effect of increasing $MgCl_2$ cation content on the 12.5% PEG formulation.

An aqueous solution containing dissolved cholesterol-modified siRNA depicted in FIG. 17 was heated to 37° C. Polymer solutions containing PEG 3350 buffered with sodium acetate were mixed to solutions containing $MgCl_2$ solutions over a range of 22.5 mM to 32.5 mM and heated to 65° C. At 65° C., aliquots of the siRNA solution were mixed to aliquots of the polymer/cation solutions to final concentrations of 0.142 mM siRNA, 12.5% (w/v) polymer, 22.5 mM, 25 mM, 27.5 mM, 30 mM, or 32.5 mM $MgCl_2$, and 67 mM buffer. Molar ratios of polyvalent cation to cholesterol-modified siRNA in the reaction mixtures were 158:1, 176:1, 193:1, 211:1, and 229:1, respectively. The reaction mixtures were incubated at 65° C. for 10 minutes and the mixtures remained clear. The mixtures were then cooled at 0.75° C./minute to 0° C., during which time microspheres, turning the mixtures milky white. The microspheres were collected through centrifugation, washed three times with a binary solution of 50% 2-methyl-2-propanol and 50% water (w/v), re-suspended in the binary solution, frozen, and lyophilized into a dry powder.

The resulting microspheres from each reaction were solid, spherical, monodispersed in particle, as visualized with light microscopy and scanning electron microscopy, except for the reaction including 22.5 mM $MgCl_2$ which, for some unknown reason, failed to yield many microspheres.

Example 18

Selection of a Formulation for Biological Characterization Studies

The results above led to repeated experiments including various $MgCl_2$ and $CaCl_2$ formulations to select one cation concentration for use in biological characterization studies.

An aqueous solution containing dissolved cholesterol-modified siRNA depicted in FIG. 17 was heated to 37° C. PEG3500 solutions buffered with sodium acetate were mixed to solutions containing either $CaCl_2$ or $MgCl_2$ at specific concentrations and heated to 65° C. At 65° C., aliquots of the siRNA solution were mixed with aliquots of the polymer/cation solutions at final concentrations for the PEG with $MgCl_2$ reactions were 0.142 mM siRNA, 12.5% (w/v) polymer, 25 mM or 32.5 mM $MgCl_2$, and 67 mM buffer, with final molar ratios of polyvalent cation and cholesterol-modified siRNA in the mixtures of 176:1, or 229:1 respectively. For the PEG reactions with $CaCl_2$ the final concentrations were 0.142 mM siRNA, 16.7% or 12.5% (w/v) polymer, 9 mM $CaCl_2$, and 67 mM buffer. Molar ratios of polyvalent cation and cholesterol-modified siRNA in these reaction mixtures were 63:1. Each reaction mixtures was incubated at 65° C. for 10 minutes and the mixtures remained clear. Afterwards, the mixtures were cooled at 0.8° C./minute to −5° C., during which time microspheres formed, turning the mixtures milky white. The microspheres were collected through centrifugation, washed three times with a binary solution of 50% 2-methyl-2-propanol and 50% water (w/v), re-suspended in the binary solution, frozen, and lyophilized into a dry powder.

The resulting microspheres were solid, spherical, monodispersed in particle size, as visualized with light microscopy and scanning electron microscopy. Aerosizer analysis show that the $CaCl_2$ based formulations in this experiment demonstrated more agglomeration compared to the $MgCl_2$ formulations.

Example 19

Production of Microspheres for Biological Characterization

The results described above provided a method to generate microsphere for biological characterization studies.

An aqueous solution containing dissolved cholesterol-modified eGFP siRNA depicted in FIG. 17 was heated to 37° C. A PEG3500 polymer solution buffered with sodium acetate was mixed with a $MgCl_2$ solution and heated to 65° C. At 65° C., an aliquot of the siRNA solution was mixed with an aliquot of the polymer/cation solution to final concentrations of the cholesterol-modified siRNA, the polymer, the cation, and the buffer of 0.142 mM, 12.5% (w/v), 25 mM, and 67 mM, respectively. The molar ratio of polyvalent cation to cholesterol-modified siRNA in the reaction mixture was 176:1. The reaction mixture was incubated at 65° C. for 10 minutes and the mixture remained clear. After incubation, the mixture was cooled at 0.8° C./minute to −5° C., during which time microspheres formed, turning the mixtures milky white. The microspheres were collected through centrifugation, washed three times with a binary solution of 50% 2-methyl-2-propanol and 50% water (w/v), re-suspended in the binary solution, frozen, and lyophilized into a dry powder.

The resulting microspheres were solid, spherical, monodispersed in particle size, as visualized with light microscopy and scanning electron microscopy. Aerosizer analysis also showed a monodispersed particle size suitable for delivery to the lung.

Example 20

In Vivo Delivery of Cholesterol-Modified siRNA

Microspheres comprised of cholesterol-modified eGFP siRNA as shown in Fig. X were utilized in a transgenic mouse modified to express GFP under transcriptional control of the human ubiquitin C (UBC) promoter in order to determine effectiveness of the microspheres to knock down GFP protein expression. UBC-GFP expressing transgenic mice are described in Palliser, et al., Nature (2006) 439:89-94 and Swenson, et al., Stem Cells (2007) 25:2593-2600.

In a first experiment, 2 nmol cholesterol-modified eGFP siRNA microspheres prepared as described in Example 19 above were administered intravaginally to mice and GFP expression in vaginal mucosa assessed after 72 hours. The 2 nmol dose was equivalent to a dosage of approximately 1 mg/kg. The negative control was microsphere suspension buffer and the positive control was eGFP siRNA with Oligofectamine (Invitrogen). GFP expression was detected and quantitated using techniques known in the art.

Results showed that GFP expression was essentially eliminated (FIG. 18) with the positive control compared to the negative control. It is noted that the positive control in this experiment was not a cholesterol modified siRNA. Still results showed that GFP expression after administration of the cholesterol modified eGFP siRNA microspheres was significantly reduced compared to the negative control demonstrating proof of concept.

In a related experiment, knock down of GFP expression in actin-GFP transgenic mice (Guo, et al., Transgenic Research (2007) 16:829-834) using cholesterol modified siRNA microspheres, prepared as described in Example 19 above, was shown to be dose-dependent. In brief mice were administered 0.0.5, 1, 2, and 4 nmol siRNA microsphere intravaginally and GFP protein expression assessed in vaginal mucosa. Increasing knock down of GFP expression was observed with increasing amounts of cholesterol modified GFP siRNA and the degree of knock down at the highest amount of siRNA was found to be essentially the same as found with an equal amount of cholesterol modified GFP siRNA which was not in a microsphere formulation. (FIG. 19 A-F).

In still another related experiment, UBC-EGFP transgenic mice were administered 2 nmol cholesterol modified EGFP siRNA microspheres intravaginally and knock down of GFP expression in vaginal mucosa was assessed over a period of 14 days at days 1, 3, 5, 7, and 14.

Results showed that knock-down of EGFP expression could be sustained for a period of time greater than 72 hours as observed in the previous experiments. Indeed, knock-down was observed for approximately 5 to 7 days after a single administration.

Example 20

In Vivo Delivery of Cholesterol-Modified siRNA

In analyses of nucleic acid loading in microparticles produced in the examples described above, it was found by measuring absorbance at 260 nm that antisense DNA oligonucleotides comprised approximately 65% to about 75% of the microparticle when formed using $CaCl_2$, unmodified siRNA comprised approximately 70% to about 95% of the microparticle when formed with $MgCl_2$, and cholesterol modified siRNA comprised approximately 55% to about 90% of the microparticle when formed using $MgCl_2$.

The invention claimed is:

1. A composition comprising a plurality of nucleic acid microparticles comprising one or more nucleic acids and one or more non-polymeric cations wherein the microparticles are substantially spherical, water-soluble at ambient temperature and have an average particle size of 0.5 microns to 5 microns, wherein the microparticles are free of polymeric polycations, the microparticles having a structure attributed to the nucleic acids in combination with the non-polymeric cations, the non-polymeric cations comprising 3% or greater of individual microparticles as measured by atomic absorption.

2. The composition of claim 1 wherein said microparticles comprise less than 10 weight % of the one or more non-polymeric cation and greater than 50 weight % of the one or more nucleic acids.

3. An aerosol composition comprising a composition of claim 1.

4. Nucleic acid microparticle comprising one or more nucleic acids and one or more non-polymeric cations, wherein the microparticle is free of polymeric polycations and free of non-nucleic acid matrices, cores, or envelops, the microparticles having a structure attributed to the nucleic acids in combination with the non-polymeric cations, the one or more non-polymeric cations comprising 3% or greater of the microparticle as measured by atomic absorption.

5. A microparticle produced by a method comprising forming a solution or a dispersion comprising one or more nucleic acids, one or more non-polymeric cations, and one or more non-ionic polymers; and cooling the solution or dispersion to form a plurality of substantially spherical nucleic acid microparticles, wherein the microparticles are free of polymeric polycations and free of non-nucleic acid matrices, cores, or envelopes, the microparticles having a structure attributed to the nucleic acids in combination with the non-polymeric cations, the one or more non-polymeric cations comprising 3% or greater of individual microparticles as measured by atomic absorption.

6. The composition of claim 1 which is free of non-nucleic acid matrices and non-nucleic acid cores.

7. The composition of claim 1 which is free of non-nucleic acid matrices, non-nucleic acid cores and non-nucleic acid envelopes.

8. The composition of claim 1, said microparticles comprise between about 4 weight % to about 10 weight % of a non-polymeric cation.

9. The composition of claim 8, wherein the non-polymeric cation is selected from the group consisting of $Ca^{2+}$, $Zn^{2+}$, $Mn^{2+}$, $Na^+$, $Ba^{2+}$, $K^+$, $Mg^{2+}$, $Mn^{2+}$, $Co^{2+}$, $Cu^{2+}$, $Fe^{2+}$, $Fe^{3+}$, $Al^{3+}$, and $Li^+$.

10. The composition of claim 1, wherein said nucleic acid is an antisense oligonucleotide.

11. The composition of claim 1, wherein said nucleic acid is an siRNA.

12. The composition of claim 1, wherein said microparticles in said composition are monodispersed.

13. The composition of claim 2 wherein said microparticles comprise less than 6 weight % of one or more non-polymeric cation and greater than 60 weight % of the one or more nucleic acids.

* * * * *

UNITED STATES PATENT AND TRADEMARK OFFICE
CERTIFICATE OF CORRECTION

PATENT NO. : 8,808,747 B2
APPLICATION NO. : 12/105213
DATED : August 19, 2014
INVENTOR(S) : Brown et al.

Page 1 of 1

It is certified that error appears in the above-identified patent and that said Letters Patent is hereby corrected as shown below:

In the Claims:

At Column 56, line 45, "Nucleic" should be -- A nucleic --.

At Column 56, line 53, "comprising" should be -- comprising: --.

Signed and Sealed this
Eighteenth Day of August, 2015

Michelle K. Lee
*Director of the United States Patent and Trademark Office*